United States Patent
Kalish et al.

(10) Patent No.: US 10,730,828 B2
(45) Date of Patent: Aug. 4, 2020

(54) N-HYDROXYLSULFONAMIDE DERIVATIVES AS NITROXYL DONORS

(71) Applicants: Cardioxyl Pharmaceuticals, Inc., Chapel Hill, NC (US); The Johns Hopkins University, Baltimore, MD (US)

(72) Inventors: Vincent Jacob Kalish, Annapolis, MD (US); Lisa Marie Frost, Abingdon (GB); Frederick Arthur Brookfield, Abingdon (GB); Stephen Martin Courtney, Abingdon (GB); John P. Toscano, Glen Arm, MD (US)

(73) Assignees: Cardioxyl Pharmaceuticals, Inc., Chapel Hill, NC (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/769,171

(22) PCT Filed: Oct. 18, 2016

(86) PCT No.: PCT/US2016/057478
§ 371 (c)(1),
(2) Date: Apr. 18, 2018

(87) PCT Pub. No.: WO2017/070084
PCT Pub. Date: Apr. 27, 2017

(65) Prior Publication Data
US 2018/0305304 A1    Oct. 25, 2018

Related U.S. Application Data

(60) Provisional application No. 62/243,267, filed on Oct. 19, 2015.

(51) Int. Cl.
*C07C 311/48* (2006.01)
*C07D 213/71* (2006.01)
(Continued)

(52) U.S. Cl.
CPC .............. *C07C 311/48* (2013.01); *A61P 9/00* (2018.01); *C07C 317/14* (2013.01);
(Continued)

(58) Field of Classification Search
CPC .. C07D 295/26; C07D 333/34; C07D 405/12; C07D 413/12
See application file for complete search history.

(56) References Cited

U.S. PATENT DOCUMENTS

| | | | |
|---|---|---|---|
| 6,936,639 B2 | 8/2005 | Wink et al. | |
| 7,696,373 B2 | 4/2010 | King | |

(Continued)

FOREIGN PATENT DOCUMENTS

| | | |
|---|---|---|
| EP | 1174028 | 12/2004 |
| GB | 1108950 | 4/1968 |

(Continued)

OTHER PUBLICATIONS

Goldfarb, R.A., "N 1-Alkoxysulfanilamide Derivatives", in the Journal of the American Chemical Society, vol. 67, No. 10, Oct. 1, 1945, pp. 1852-1853.

(Continued)

*Primary Examiner* — Valerie Rodriguez-Garcia
(74) *Attorney, Agent, or Firm* — Byrne Poh LLP; Nina R. Horan

(57) ABSTRACT

The disclosed subject matter provides N-hydroxylsulfonamide derivative compounds of formulae (I), (II) or (III) as drawn below, pharmaceutical compositions comprising such compounds, kits comprising such compounds, and methods of using such compounds or pharmaceutical compositions. In particular, the disclosed subject matter provides methods of using such compounds or pharmaceutical compositions for treating heart failure.

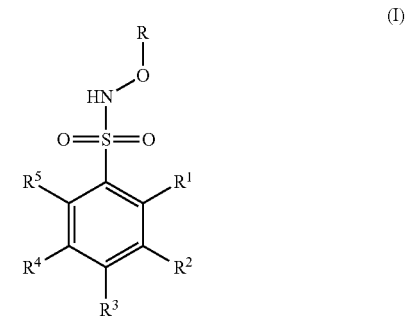

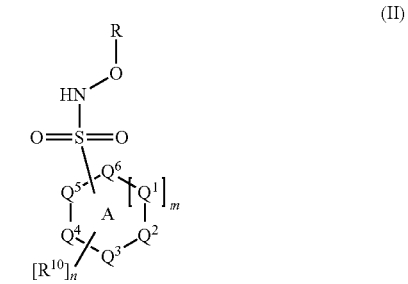

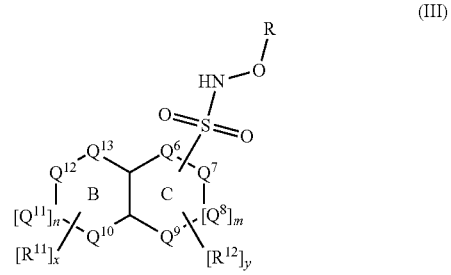

4 Claims, No Drawings

(51) Int. Cl.
  *C07D 309/10* (2006.01)
  *C07D 317/40* (2006.01)
  *C07D 317/54* (2006.01)
  *C07D 231/12* (2006.01)
  *C07D 333/34* (2006.01)
  *C07C 317/14* (2006.01)
  *C07D 405/12* (2006.01)
  *C07D 413/12* (2006.01)
  *C07D 241/24* (2006.01)
  *C07D 261/08* (2006.01)
  *C07D 271/12* (2006.01)
  *C07D 213/30* (2006.01)
  *C07D 307/52* (2006.01)
  *C07D 307/82* (2006.01)
  *A61P 9/00* (2006.01)

(52) U.S. Cl.
  CPC ......... *C07D 213/30* (2013.01); *C07D 213/71* (2013.01); *C07D 231/12* (2013.01); *C07D 241/24* (2013.01); *C07D 261/08* (2013.01); *C07D 271/12* (2013.01); *C07D 307/52* (2013.01); *C07D 307/82* (2013.01); *C07D 309/10* (2013.01); *C07D 317/40* (2013.01); *C07D 317/54* (2013.01); *C07D 333/34* (2013.01); *C07D 405/12* (2013.01); *C07D 413/12* (2013.01); *C07C 2601/08* (2017.05)

(56) References Cited

U.S. PATENT DOCUMENTS

| | | | |
|---|---|---|---|
| 7,863,262 B2 | 1/2011 | Wink et al. | |
| 7,989,652 B2 | 8/2011 | King | |
| 8,227,639 B2 | 7/2012 | Toscano et al. | |
| 8,268,890 B2 | 9/2012 | Wink et al. | |
| 8,269,034 B2 | 9/2012 | King | |
| 8,569,536 B2 | 10/2013 | King | |
| 8,674,132 B2 * | 3/2014 | Toscano | C07C 311/48 564/90 |
| RE45,314 E | 12/2014 | Toscano et al. | |
| 8,987,326 B2 | 3/2015 | Kalish et al. | |
| 9,115,064 B2 | 8/2015 | Toscano et al. | |
| 9,156,804 B2 | 10/2015 | Kalish et al. | |
| 9,221,780 B2 | 12/2015 | Toscano et al. | |
| 9,487,498 B2 | 11/2016 | Toscano et al. | |
| 9,586,896 B2 | 3/2017 | Kalish et al. | |
| 9,617,208 B2 | 4/2017 | Toscano et al. | |
| 9,725,410 B2 | 8/2017 | Toscano et al. | |
| 9,968,584 B2 | 5/2018 | Kalish et al. | |
| 9,969,684 B2 | 5/2018 | Toscano et al. | |
| 2012/0201907 A1 | 8/2012 | Wink et al. | |
| 2014/0235636 A1 | 8/2014 | Toscano et al. | |
| 2015/0004259 A1 | 1/2015 | Wink et al. | |
| 2015/0366977 A1 | 12/2015 | Kalish et al. | |
| 2016/0046570 A1 | 2/2016 | Toscano et al. | |
| 2016/0228460 A1 | 8/2016 | Wink et al. | |
| 2018/0050985 A1 | 2/2018 | Toscano et al. | |

FOREIGN PATENT DOCUMENTS

| | | | |
|---|---|---|---|
| WO | WO 1996/04242 | | 2/1996 |
| WO | WO 2005/074598 | | 8/2005 |
| WO | WO 2007/002444 | | 1/2007 |
| WO | WO 2007/109175 | | 9/2007 |
| WO | WO 2009/042970 | * | 4/2009 |
| WO | WO 2009/137717 | | 11/2009 |
| WO | WO 2011/063400 | | 5/2011 |
| WO | WO 2011/071947 | | 6/2011 |
| WO | WO 2011/071951 | | 6/2011 |
| WO | WO 2013/059194 | | 4/2013 |
| WO | WO 2014/070919 | | 5/2014 |
| WO | WO 2014/113696 | | 7/2014 |
| WO | WO 2014/113700 | | 7/2014 |
| WO | WO 2015/109210 | | 7/2015 |
| WO | WO 2015/183838 | | 12/2015 |
| WO | WO 2015/183839 | | 12/2015 |
| WO | WO 2016/210392 | | 12/2016 |
| WO | WO 2017/070081 | | 4/2017 |

OTHER PUBLICATIONS

International Preliminary Report on Patentability dated Apr. 24, 2018 in International Patent Application No. PCT/US2016/057478.
International Search Report and Written Opinion dated Feb. 9, 2017 in International Patent Application No. PCT/US2016/057478.

* cited by examiner

N-HYDROXYLSULFONAMIDE DERIVATIVES AS NITROXYL DONORS

1. BACKGROUND

Nitroxyl (HNO) has been shown to have positive cardiovascular effects in in vitro and in vivo models of failing hearts. However, at physiological pH, nitroxyl dimerizes to hyponitrous acid, which subsequently dehydrates to nitrous oxide. Owing to this metastability, nitroxyl for therapeutic use is typically generated in situ from donor compounds. A variety of compounds capable of donating nitroxyl have been described and proposed for use in treating disorders known or suspected to be responsive to nitroxyl. See, e.g., U.S. Pat. Nos. 6,936,639, 7,696,373, 8,030,356, 8,268,890, 8,227,639, and 8,318,705, U.S. pre-grant publication nos. 2009/0281067, 2009/0298795, 2011/0136827, and 2011/0144067, PCT international publication no. WO 2013/059194, and Paolocci et al., *Pharmacol. Therapeutics* 113: 442-458 (2007). Although compounds in these references are disclosed to be capable of donating nitroxyl, they differ in various physicochemical properties and there remains a need to identify nitroxyl donors that have physicochemical properties best suited for treating specific clinical conditions via specific routes of administration.

Accordingly, there is a need to provide nitroxyl donating compounds and compositions that are useful for the treatment of heart failure.

Citation of any reference in Section 1 of this application is not to be construed as an admission that such reference is prior art to the present application.

2. SUMMARY OF THE DISCLOSURE

The present disclosure relates to N-hydroxylsulfonamide derivative compounds, pharmaceutical compositions comprising such compounds, kits comprising such compounds, and methods of using such compounds or pharmaceutical compositions.

In a particular embodiment, an N-hydroxylsulfonamide derivative compound of the disclosure is compound of formula (I):

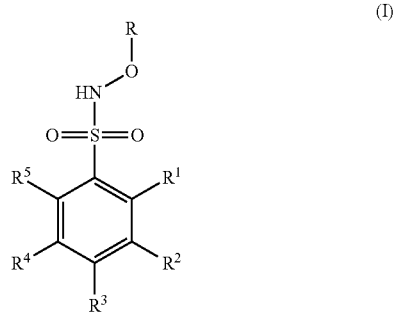

(I)

or a pharmaceutically acceptable salt thereof, wherein:
$R^1$ is H, halo, $(C_1-C_6)$alkyl, $(C_1-C_6)$alkylsulfanyl, $(C_1-C_6)$alkylsulfinyl or $(C_1-C_6)$alkylsulfonyl;
$R^2$ is H, $(C_1-C_6)$alkylsulfanyl, $(C_1-C_6)$alkylsulfinyl, $(C_1-C_6)$alkylsulfonyl, $(C_1-C_6)$haloalkyl or $(C_1-C_6)$perhaloalkyl;
$R^3$ is H, $(C_1-C_6)$alkylsulfanyl, $(C_1-C_6)$alkylsulfinyl, $(C_1-C_6)$alkylsulfonyl or $NR^6R^7$, wherein
$R^6$ and $R^7$ are independently selected from H and $(C_1-C_6)$alkyl, wherein said alkyl is unsubstituted or substituted with (5- or 6-membered)heteroaryl;
$R^4$ is H, COOH, or $CONR^8OR^9$, wherein
$R^8$ and $R^9$ are independently selected from H and $(C_1-C_6)$alkyl, wherein said alkyl is unsubstituted or substituted with phenyl;
$R^5$ is H; and
R is $(C_1-C_6)$alkyl, (5- or 6-membered)heterocycloalkyl, $(C_5-C_7)$cycloalkyl or C(=O)(5- or 6-membered)heteroaryl, wherein said alkyl is unsubstituted or substituted with a substituent selected from phenyl, (5- or 6-membered)heterocycloalkyl, (5- or 6-membered)heterocycloalkenyl, (5- or 6-membered)heteroaryl, or O(C=O)$(C_1-C_6)$alkyl, wherein said phenyl is unsubstituted or substituted with 1, 2, 3, 4 or 5 substituent(s) independently selected from the group consisting of halo, OH, $(C_1-C_6)$alkyl, $(C_1-C_6)$haloalkyl, $(C_1-C_6)$perhaloalkyl, $(C_1-C_6)$alkoxy, $(C_1-C_6)$haloalkoxy, $(C_1-C_6)$perhaloalkoxy, $(C_1-C_6)$alkylsulfanyl, $(C_1-C_6)$alkylsulfinyl, $(C_1-C_6)$alkylsulfonyl, $SO_2$-(5- or 6-membered)heterocycloalkyl, (5- or 6-membered)heteroaryl, OC(=O)$(C_1-C_6)$alkyl, NHC(=O) $(C_1-C_6)$alkyl, N$(C_1-C_6)$alkyl-(C=O) $(C_1-C_6)$alkyl, C(=O)NH$(C_1-C_6)$alkyl, C(=O)N-di$(C_1-C_6)$alkyl, C(=O)NH$(C_1-C_6)$alkoxy, C(=O)N-di$(C_1-C_6)$alkoxy, N—$(C_1-C_6)$alkylaminosulfonyl, N,N-di$(C_1-C_6)$alkylaminosulfonyl, N—$(C_1-C_6)$alkoxyaminosulfonyl, and N,N-di$(C_1-C_6)$alkoxyaminosulfonyl;

wherein said phenyl is optionally fused to a (5- or 6-membered)heterocycloalkyl or (5- or 6-membered)heteroaryl; and wherein said heterocycloalkyl, heterocycloalkenyl and heteroaryl are unsubstituted or substituted with 1, 2 or 3 substituent(s) independently selected from oxo, $(C_1-C_6)$alkyl, $(C_1-C_6)$haloalkyl, and $(C_1-C_6)$perhaloalkyl, provided that:
(1) at least one of $R^1$, $R^2$, $R^3$, $R^4$ and $R^5$ is other than H;
(2) when $R^1$ is halo and $R^2$, $R^3$, $R^4$ and $R^5$ are each H, then R is not unsubstituted benzyl, ethyl, cyclopentyl, pyrrolidinylethyl, piperidinylethyl, morpholinylethyl, furanpropyl, or tetrahydro-2H-pyranyl;
(3) when $R^1$ is methyl, and $R^2$, $R^3$, $R^4$ and $R^5$ are each H, then R is not isobutyl, cyclopentyl, unsubstituted benzyl, pyrrolidinylethyl, piperidinylethyl, morpholinylethyl, furanpropyl, or pyrrolidinyl;
(4) when $R^1$ is methyl or ethyl, and $R^2$, $R^3$, and $R^5$ are each H, and $R^4$ is COOH, then R is not cyclopentyl, ethyl or isobutyl;
(5) when $R^1$ is halo, $R^2$, $R^3$, and $R^5$ are each H, and $R^4$ is COOH, then R is not ethyl, iso-butyl or cyclopentyl;
(6) when $R^3$ is $SO_2CH_3$ and $R^1$, $R^2$, $R^4$ and $R^5$ are each H, then R is not ethyl, iso-butyl or cyclopentyl;
(7) when $R^2$ is trifluoromethyl, $R^1$ is H or methyl, and $R^3$, $R^4$ and $R^5$ are each H, then R is not ethyl, iso-butyl or cyclopentyl; and
(8) when $R^3$ is $NH_2$, and $R^1$, $R^2$, $R^4$ and $R^5$ are each H, then R is not 2-propyl.

In another particular embodiment, an N-hydroxylsulfonamide derivative compound of the disclosure is compound of formula (II):

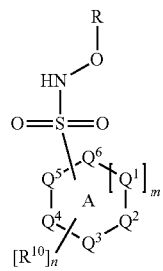

(II)

or a pharmaceutically acceptable salt thereof, wherein:
ring A is a heterocyclic or heteroaromatic ring containing $Q^1$, $Q^2$, $Q^3$, $Q^4$, $Q^5$ and $Q^6$ that are independently selected from C, CH, CH$_2$, N, NH, and S, provided that at least one of $Q^1$, $Q^2$, $Q^3$, $Q^4$, $Q^5$ and $Q^6$ is N, NH or S, wherein said N is optionally oxidized;
$R^{10}$ is $(C_1-C_6)$alkyl, halo, C(=O)-(5- or 6-membered)heterocycloalkyl, C(=O)NH—$(C_1-C_6)$alkyl or C(=O)N-di$(C_1-C_6)$alkyl;
R is $(C_1-C_6)$alkyl, wherein said alkyl is unsubstituted or substituted with phenyl;
n is an integer from 0 to 1; and
m is an integer from 0 to 1;
provided that:
(1) when ring A is 3-pyridinyl, pyrrolidinyl, azepinyl, piperidinyl, morpholinyl or thienyl, then n is not 0;
(2) when ring A is piperazinyl and n is 0, then R is not alkyl;
(3) when ring A is piperidinyl, then $R^{10}$ is not methyl;
(4) when ring A is 2-pyridinyl or 3-pyridinyl, then $R^{10}$ is not halo; and
(5) when ring A is thienyl, then $R^{10}$ is not methyl, ethyl or halo.

In another particular embodiment, an N-hydroxylsulfonamide derivative compound of the disclosure is compound of formula (III):

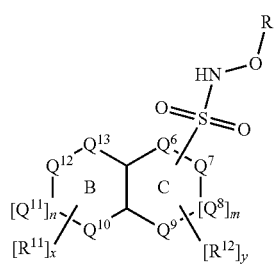

(III)

or a pharmaceutically acceptable salt thereof, wherein:
Ring B is a heteroaromatic or aromatic ring containing $Q^{10}$, $Q^{11}$, $Q^{12}$ and $Q^{13}$, wherein $Q^{10}$, $Q^{11}$, $Q^{12}$ and $Q^{13}$ are independently selected from C, CH, O, N, NH and S;
Ring C is a heteroaromatic ring containing $Q^6$, $Q^7$, $Q^8$ and $Q^9$, wherein $Q^6$, $Q^7$, $Q^8$ and $Q^9$ are independently selected from C, CH, O, N, NH and S, provided that at least one of $Q^6$, $Q^7$, $Q^8$ and $Q^9$ is O, N, NH or S;
$R^{11}$ and $R^{12}$ are independently selected from $(C_1-C_6)$alkoxy and halo;

m and n are independently selected from 0 to 1;
x is an integer selected from 0 to 4;
y is an integer selected from 0 to 3; and
R is $(C_1-C_6)$alkyl or $(C_5-C_7)$cycloalkyl, wherein said alkyl is unsubstituted or substituted with phenyl, (5- or 6-membered)heterocycloalkyl, (5- or 6-membered)heterocycloalkenyl or (5- or 6-membered)heteroaryl;
  wherein said phenyl is unsubstituted or substituted with 1, 2, 3, 4 or 5 substituents independently selected from halo, $(C_1-C_6)$alkyl and $(C_1-C_6)$alkoxy;
  wherein said heterocycloalkyl or heterocycloalkenyl is unsubstituted or substituted with 1, 2 or 3 substituents independently selected from oxo and $(C_1-C_6)$alkyl; and
  wherein said heteroaryl is unsubstituted or substituted with 1, 2 or 3 substituents selected from $(C_1-C_6)$alkyl.

3. DETAILED DESCRIPTION

The invention includes the following:
(1) A compound of formula (I):

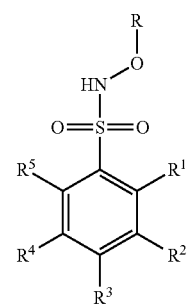

(I)

or a pharmaceutically acceptable salt thereof, wherein:
$R^1$ is H, halo, $(C_1-C_6)$alkyl, $(C_1-C_6)$alkylsulfanyl, $(C_1-C_6)$alkylsulfinyl or $(C_1-C_6)$alkylsulfonyl;
$R^2$ is H, $(C_1-C_6)$alkylsulfanyl, $(C_1-C_6)$alkylsulfinyl, $(C_1-C_6)$alkylsulfonyl, $(C_1-C_6)$haloalkyl or $(C_1-C_6)$perhaloalkyl;
$R^3$ is H, $(C_1-C_6)$alkylsulfanyl, $(C_1-C_6)$alkylsulfinyl, $(C_1-C_6)$alkylsulfonyl or $NR^6R^7$, wherein
  $R^6$ and $R^7$ are independently selected from H and $(C_1-C_6)$alkyl, wherein said alkyl is unsubstituted or substituted with (5- or 6-membered)heteroaryl;
$R^4$ is H, COOH, or $CONR^8OR^9$, wherein
  $R^8$ and $R^9$ are independently selected from H and $(C_1-C_6)$alkyl, wherein said alkyl is unsubstituted or substituted with phenyl;
$R^5$ is H; and
R is $(C_1-C_6)$alkyl, (5- or 6-membered)heterocycloalkyl, $(C_5-C_7)$cycloalkyl or C(=O)(5- or 6-membered)heteroaryl, wherein said alkyl is unsubstituted or substituted with a substituent selected from phenyl, (5- or 6-membered)heterocycloalkyl, (5- or 6-membered)heterocycloalkenyl, (5- or 6-membered)heteroaryl, or O(C=O)$(C_1-C_6)$alkyl
  wherein said phenyl is unsubstituted or substituted with 1, 2, 3, 4 or 5 substituent(s) independently selected from the group consisting of halo, OH, $(C_1-C_6)$alkyl, $(C_1-C_6)$haloalkyl, $(C_1-C_6)$perhaloalkyl, $(C_1-C_6)$alkoxy, $(C_1-C_6)$haloalkoxy, $(C_1-C_6)$perhaloalkoxy, $(C_1-C_6)$alkylsulfanyl, $(C_1-C_6)$alkylsulfinyl, $(C_1-C_6)$alkylsulfonyl, $SO_2$-(5- or 6-membered)heterocycloalkyl, (5- or 6-membered)heteroaryl, OC(=O)

(C₁-C₆)alkyl, NHC(=O) (C₁-C₆)alkyl, N(C₁-C₆)alkyl-(C=O) (C₁-C₆)alkyl, C(=O)NH(C₁-C₆)alkyl, C(=O)N-di(C₁-C₆)alkyl, C(=O)NH(C₁-C₆)alkoxy, C(=O)N-di(C₁-C₆)alkoxy, N—(C₁-C₆)alkylaminosulfonyl, N,N-di(C₁-C₆)alkylaminosulfonyl, N—(C₁-C₆)alkoxyaminosulfonyl, and N,N-di(C₁-C₆)alkoxyaminosulfonyl;

wherein said phenyl is optionally fused to a (5- or 6-membered)heterocycloalkyl or (5- or 6-membered)heteroaryl; and wherein said heterocycloalkyl, heterocycloalkenyl and heteroaryl are unsubstituted or substituted with 1, 2 or 3 substituent(s) independently selected from oxo, (C₁-C₆)alkyl, (C₁-C₆)haloalkyl, and (C₁-C₆)perhaloalkyl, provided that:

(i) at least one of $R^1$, $R^2$, $R^3$, $R^4$ and $R^5$ is other than H;

(ii) when $R^1$ is halo and $R^2$, $R^3$, $R^4$ and $R^5$ are each H, then R is not unsubstituted benzyl, ethyl, cyclopentyl, pyrrolidinylethyl, piperidinylethyl, morpholinylethyl, furanpropyl, or tetrahydro-2H-pyranyl;

(iii) when $R^1$ is methyl, and $R^2$, $R^3$, $R^4$ and $R^5$ are each H, then R is not isobutyl, cyclopentyl, unsubstituted benzyl, pyrrolidinylethyl, piperidinylethyl, morpholinylethyl, furanpropyl, or pyrrolidinyl;

(iv) when $R^1$ is methyl or ethyl, and $R^2$, $R^3$, and $R^5$ are each H, and $R^4$ is COOH, then R is not cyclopentyl, ethyl or isobutyl;

(v) when $R^1$ is halo, $R^2$, $R^3$, and $R^5$ are each H, and $R^4$ is COOH, then R is not ethyl, iso-butyl or cyclopentyl;

(vi) when $R^3$ is $SO_2CH_3$ and $R^1$, $R^2$, $R^4$ and $R^5$ are each H, then R is not ethyl, iso-butyl or cyclopentyl;

(vii) when $R^2$ is trifluoromethyl, $R^1$ is H or methyl, and $R^3$, $R^4$ and $R^5$ are each H, then R is not ethyl, iso-butyl or cyclopentyl; and (viii) when $R^3$ is $NH_2$, and $R^1$, $R^2$, $R^4$ and $R^5$ are each H, then R is not 2-propyl.

(2) The compound of the above (1), wherein $R^1$ is H, halo, (C₁-C₆)alkyl, or (C₁-C₆)alkylsulfonyl.

(3) The compound of the above (2), wherein $R^1$ is H, halo, methyl, or methylsulfonyl.

(4) The compound of the above (1), wherein $R^1$ is H.

(5) The compound of the above (1), wherein $R^1$ is halo.

(6) The compound of the above (5), wherein $R^1$ is F, Cl or Br.

(7) The compound of the above (5), wherein $R^1$ is Cl or Br.

(8) The compound of the above (5), wherein $R^1$ is Cl.

(9) The compound of the above (5), wherein $R^1$ is Br.

(10) The compound of any one of the above (1) to (9), wherein $R^2$ is H, (C₁-C₆)alkylsulfonyl, or (C₁-C₆)perhaloalkyl.

(11) The compound of the above (10), wherein $R^2$ is H, methylsulfonyl, or perhalomethyl.

(12) The compound of the above (10), wherein $R^2$ is H, methylsulfonyl, or perfluoromethyl.

(13) The compound of any one of the above (1) to (12), wherein $R^3$ is H, (C₁-C₆)alkylsulfonyl or $NR^6R^7$.

(14) The compound of the above (13), wherein $R^3$ is H, methylsulfonyl or $NHR^7$, wherein $R^7$ is (C₁-C₆)alkyl, wherein said alkyl is unsubstituted or substituted with a (5- or 6-membered)heteroaryl.

(15) The compound of the above (14), wherein $R^7$ is (C₁-C₆)alkyl substituted with a (5- or 6-membered)heteroaryl.

(16) The compound of the above (15), wherein $R^7$ is $(C_1)$alkyl substituted with a (5- or 6-membered)heteroaryl.

(17) The compound of the above (16), wherein $R^7$ is $(C_1)$alkyl substituted with a (5-membered)heteroaryl.

(18) The compound of the above (17), wherein $R^7$ is $(C_1)$alkyl substituted with furanyl.

(19) The compound of the above (14), wherein $R^3$ is H.

(20) The compound of the above (14), wherein $R^3$ is methylsulfonyl.

(21) The compound of the above (14), wherein $R^3$ is $NHR^7$, wherein $R^7$ is $(C_1)$alkyl substituted with furanyl.

(22) The compound of any one of the above (1) to (21), wherein $R^4$ is H, COOH, or $CONR^8OR^9$, where $R^8$ is H and $R^9$ is (C₁-C₆)alkyl, wherein said alkyl is unsubstituted or substituted with phenyl.

(23) The compound of the above (22), wherein $R^9$ is (C₁-C₆)alkyl substituted with phenyl.

(24) The compound of the above (23), wherein $R^9$ is $(C_1)$alkyl substituted with phenyl.

(25) The compound of the above (22), wherein $R^4$ is H.

(26) The compound of the above (22), wherein $R^4$ is COOH.

(27) The compound of the above (22), wherein $R^4$ is $CONHOR^9$, where $R^9$ is $(C_1)$alkyl substituted with phenyl.

(28) The compound of any one of the above (1) to (27), wherein R is unsubstituted (C₁-C₆)alkyl.

(29) The compound of the above (28), wherein R is methyl, ethyl, propyl or butyl.

(30) The compound of any one of the above (1) to (27), wherein R is (C₁-C₆)alkyl substituted with phenyl.

(31) The compound of the above (30), wherein R is (C₁-C₃)alkyl substituted with phenyl.

(32) The compound of the above (30) or (31), wherein said phenyl is unsubstituted.

(33) The compound of the above (30) or (31), wherein said phenyl is substituted 1, 2, or 3 substituent(s) independently selected from the group consisting of halo, OH, (C₁-C₆)alkyl, (C₁-C₆)haloalkyl, (C₁-C₆)perhaloalkyl, (C₁-C₆)alkoxy, (C₁-C₆)haloalkoxy, (C₁-C₆)perhaloalkoxy, (C₁-C₆)alkylsulfanyl, (C₁-C₆)alkylsulfinyl, (C₁-C₆)alkylsulfonyl, $SO_2$-(5- or 6-membered)heterocycloalkyl, (5- or 6-membered)heteroaryl, OC(=O)(C₁-C₆)alkyl, NHC(=O) (C₁-C₆)alkyl, N(C₁-C₆)alkyl-(C=O) (C₁-C₆)alkyl, C(=O)NH (C₁-C₆)alkyl, C(=O)N-di(C₁-C₆)alkyl, C(=O)NH (C₁-C₆)alkoxy, C(=O)N-di(C₁-C₆)alkoxy, N—(C₁-C₆)alkylaminosulfonyl, N,N-di(C₁-C₆)alkylaminosulfonyl, N—(C₁-C₆)alkoxyaminosulfonyl, and N,N-di(C₁-C₆)alkoxyaminosulfonyl; and wherein said phenyl is optionally fused to a (5- or 6-membered)heterocycloalkyl or (5- or 6-membered)heteroaryl.

(34) The compound of the above (33), wherein said phenyl is substituted 1, 2, or 3 substituent(s) independently selected from the group consisting of OC(=O)$CH_3$, OH, $CF_3$, F, Cl, Br, methyl, propyl, butyl, methoxy, $SO_2$-morpholine, perfluoromethoxy, methylsulfonyl, $CON(CH_2CH_2OCH_3)_2$, 1H-pyrazol-1-yl, $NHCOCH_3$, $SO_2N(CH_2CH_2OCH_3)_2$.

(35) The compound of any one of the above (1) to (27), wherein R is (C₁-C₆)alkyl substituted with (5- or 6-membered)heterocycloalkyl or (5- or 6-membered)heterocycloalkenyl.

(36) The compound of the above (35), wherein R is ($C_1$)alkyl substituted with a (5- or 6-membered)heterocycloalkyl or a (5- or 6-membered)heterocycloalkenyl.

(37) The compound of the above (36), wherein R is ($C_1$)alkyl substituted with a (5-membered)heterocycloalkyl or a (5-membered)heterocycloalkyl.

(38) The compound of the above (36), wherein R is ($C_1$)alkyl substituted with a (6-membered)heterocycloalkyl or a (6-membered)heterocycloalkenyl.

(39) The compound of the above (35), wherein said heterocycloalkyl or heterocycloalkenyl is unsubstituted.

(40) The compound of the above (35), wherein said heterocycloalkyl or heterocycloalkenyl is substituted with 1, 2 or 3 substituent(s) independently selected from oxo, ($C_1$-$C_6$)alkyl, ($C_1$-$C_6$)haloalkyl, and ($C_1$-$C_6$)perhaloalkyl.

(41) The compound of the above (35) or (40), wherein R is ($C_1$)alkyl substituted with 2-oxo-2H-1,3-dioxol-4-yl.

(42) The compound of the above (41), wherein said heterocycloalkyl or heterocycloalkenyl is substituted with oxo and methyl.

(43) The compound of any one of the above (1) to (27), wherein R is ($C_1$-$C_6$)alkyl substituted with (5- or 6-membered)heteroaryl.

(44) The compound of the above (43), wherein R is ($C_1$)alkyl substituted with (5- or 6-membered)heteroaryl.

(45) The compound of the above (44), wherein said heteroaryl is selected from pyridinyl, oxazolyl and furanyl.

(46) The compound of the above (44) or (45), wherein said heteroaryl is unsubstituted.

(47) The compound of the above (44) or (45), wherein said heteroaryl is substituted with 1, 2 or 3 substituent(s) independently selected from ($C_1$-$C_6$) alkyl, ($C_1$-$C_6$)haloalkyl, and ($C_1$-$C_6$)perhaloalkyl.

(48) The compound of any one of the above (1) to (27), wherein R is ($C_1$-$C_6$)alkyl substituted with O(C=O) ($C_1$-$C_6$)alkyl.

(49) The compound of the above (48), wherein R is ($C_1$-$C_2$)alkyl substituted with O(C=O)($C_1$-$C_6$)alkyl.

(50) The compound of the above (49), wherein R is ($C_1$-$C_2$)alkyl substituted with O(C=O)($C_1$-$C_4$)alkyl.

(51) The compound of any one of the above (1) to (27), wherein R is (5- or 6-membered)heterocycloalkyl or (5- or 6-membered)heterocycloalkenyl.

(52) The compound of any one of the above (1) to (27), wherein R is ($C_5$-$C_7$)cycloalkyl.

(53) The compound of any one of the above (1) to (27), wherein R is C(=O)(5- or 6-membered)heteroaryl.

(54) The compound of any one of the above (1) to (27), wherein R is C(=O)(5-membered)heteroaryl.

(55) The compound of any one of the above (1) to (27), wherein R is C(=O)(6-membered)heteroaryl.

(56) The compound of any one of the above (1) to (27), wherein said (6-membered)heteroaryl is pyridinyl, pyridazinyl, pyrimidinyl or pyrazinyl.

(57) The compound of any one of the above (1) to (27), wherein said (6-membered)heteroaryl is pyrazinyl.

(58) A compound of formula (II):

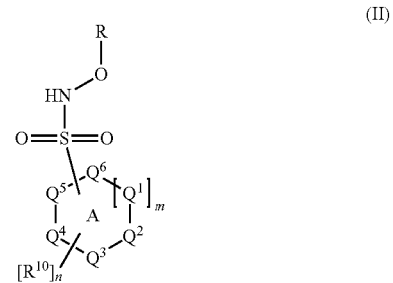

or a pharmaceutically acceptable salt thereof, wherein:
ring A is a heterocyclic or heteroaromatic ring containing $Q^1$, $Q^2$, $Q^3$, $Q^4$, $Q^5$ and $Q^6$ that are independently selected from C, CH, $CH_2$, N, NH, and S, provided that at least one of $Q^1$, $Q^2$, $Q^3$, $Q^4$, $Q^5$ and $Q^6$ is N, NH or S, wherein said N is optionally oxidized;
$R^{10}$ is ($C_1$-$C_6$)alkyl, halo, C(=O)-(5- or 6-membered) heterocycloalkyl, C(=O)NH—($C_1$-$C_6$)alkyl or C(=O)N-di($C_1$-$C_6$)alkyl;
R is ($C_1$-$C_6$)alkyl, wherein said alkyl is unsubstituted or substituted with phenyl;
n is an integer from 0 to 1; and
m is an integer from 0 to 1;
provided that:
(i) when ring A is 3-pyridinyl, pyrrolidinyl, azepinyl, piperidinyl, morpholinyl or thienyl, then n is not 0;
(ii) when ring A is piperazinyl and n is 0, then R is not alkyl;
(iii) when ring A is piperidinyl, then $R^{10}$ is not methyl;
(iv) when ring A is 2-pyridinyl or 3-pyridinyl, then $R^{10}$ is not halo; and
(v) when ring A is thienyl, then $R^{10}$ is not methyl, ethyl or halo.

(59) The compound of the above (58), wherein m is 0.
(60) The compound of the above (58), wherein m is 1.
(61) The compound of the above (58), wherein ring A is piperazinyl, thienyl, piperidinyl or pyridinium.
(62) The compound of any one of the above (58) to (61), wherein n is 0.
(63) The compound of any one of the above (58) to (61), wherein n is 1.
(64) The compound of the above (61), wherein $R^{10}$ is ($C_1$-$C_6$)alkyl.
(65) The compound of the above (64), wherein $R^{10}$ is methyl or ethyl.
(66) The compound of the above (64), wherein $R^{10}$ is methyl.
(67) The compound of the above (61), wherein $R^{10}$ is halo.
(68) The compound of the above (67), wherein $R^{10}$ is fluoro or chloro.
(69) The compound of the above (67), wherein $R^{10}$ is chloro.
(70) The compound of the above (61), wherein $R^{10}$ is C(=O)-(5- or 6-membered)heterocycloalkyl.
(71) The compound of the above (70), wherein $R^{10}$ is C(=O)-(6-membered)heterocycloalkyl.
(72) The compound of the above (71), wherein said heterocycloalkyl is morpholinyl.
(73) The compound of the above (61), wherein $R^{10}$ is C(=O)NH—($C_1$-$C_6$)alkyl.
(74) The compound of the above (73), wherein $R^{10}$ is C(=O)NH—($C_1$-$C_3$)alkyl.

(75) The compound of the above (74), wherein said alkyl is propyl.
(76) The compound of the above (58), wherein n is 1 and ring A is piperazinyl or thienyl.
(77) The compound of the above (76), wherein ring A is piperazinyl.
(78) The compound of the above (76), wherein ring A is thienyl.
(79) The compound of any one of the above (76) to (78), wherein $R^{10}$ is $(C_1\text{-}C_6)$alkyl, $C(=O)\text{-}(5\text{-}$ or 6-membered)heterocycloalkyl or $C(=O)NH\text{—}(C_1\text{-}C_6)$alkyl.
(80) The compound of the above (79), wherein $R^{10}$ is $(C_1\text{-}C_6)$alkyl.
(81) The compound of the above (80), wherein $R^{10}$ is methyl.
(82) The compound of the above (74), wherein $R^{10}$ is $C(=O)\text{-}(5\text{-}$ or 6-membered)heterocycloalkyl or $C(=O)NH\text{—}(C_1\text{-}C_6)$alkyl.
(83) The compound of the above (79), wherein $R^{10}$ is $C(=O)\text{-}(6\text{-membered})$heterocycloalkyl or $C(=O)NH\text{—}(C_1\text{-}C_6)$alkyl.
(84) The compound of the above (83), wherein $R^{10}$ is $C(=O)\text{-}(6\text{-membered})$heterocycloalkyl.
(85) The compound of the above (84), wherein $R^{10}$ is $C(=O)$-morpholinyl.
(86) The compound of the above (83), wherein $R^{10}$ is $C(=O)NH\text{—}(C_1\text{-}C_6)$alkyl.
(87) The compound of the above (86), wherein $R^{10}$ is $C(=O)NH\text{—}(C_3)$alkyl.
(88) The compound of any one of the above (77), (79), (80) or (81), wherein R is benzyl.
(89) The compound of any one of the above (78), (79), or (82) to (85), wherein R is benzyl.
(90) The compound of any one of the above (78), (79), or (82) to (85), wherein R is methyl.
(91) The compound of any one of the above (78), (79), (83), (86) or (87), wherein R is methyl.
(92) The compound of any one of the above (78), (79), (83), (86) or (87), wherein R is benzyl.
(93) The compound of the above (58), wherein n is 0 and ring A is pyridinyl or pyridinium.
(94) The compound of the above (93), wherein R is benzyl or methyl.
(95) The compound of the above (93), wherein R is benzyl.
(96) The compound of the above (93), wherein R is methyl.
(97) A compound of formula (III):

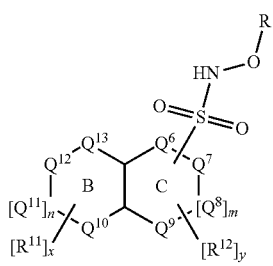

(III)

or a pharmaceutically acceptable salt thereof, wherein:
Ring B is a heteroaromatic or aromatic ring containing $Q^{10}$, $Q^1$, $Q^{12}$ and $Q^{13}$, wherein $Q^{10}$, Q, $Q^{12}$ and $Q^{13}$ are independently selected from C, CH, O, N, NH and S;
Ring C is a heteroaromatic ring containing $Q^6$, $Q^7$, $Q^8$ and $Q^9$, wherein $Q^6$, $Q^7$, $Q^8$ and $Q^9$ are independently selected from C, CH, O, N, NH and S, provided that at least one of $Q^6$, $Q^7$, $Q^8$ and $Q^9$ is O, N, NH or S;
$R^{11}$ and $R^{12}$ are independently selected from $(C_1\text{-}C_6)$alkoxy and halo;
m and n are independently selected from 0 to 1;
x is an integer selected from 0 to 4;
y is an integer selected from 0 to 3; and
R is $(C_1\text{-}C_6)$alkyl or $(C_5\text{-}C_7)$cycloalkyl, wherein said alkyl is unsubstituted or substituted with phenyl, (5- or 6-membered)heterocycloalkyl, (5- or 6-membered)heterocycloalkenyl or (5- or 6-membered)heteroaryl;
wherein said phenyl is unsubstituted or substituted with 1, 2, 3, 4 or 5 substituents independently selected from halo, $(C_1\text{-}C_6)$alkyl and $(C_1\text{-}C_6)$alkoxy;
wherein said heterocycloalkyl and heterocycloalkenyl are unsubstituted or substituted with 1, 2 or 3 substituents independently selected from oxo and $(C_1\text{-}C_6)$alkyl; and
wherein said heteroaryl is unsubstituted or substituted with 1, 2 or 3 substituents selected from $(C_1\text{-}C_6)$alkyl.
(98) The compound of the above (97), wherein ring B is an aromatic ring.
(99) The compound of the above (98), wherein x is 0 or 1.
(100) The compound of the above (99), wherein x is 0.
(101) The compound of any one of the above (97) to (100), wherein ring C is a heteroaromatic ring in which one of $Q^6$, $Q^7$, $Q^8$ and $Q^9$ is O, NH or S.
(102) The compound of the above (101), wherein one of $Q^6$, $Q^7$, $Q^8$ and $Q^9$ is O.
(103) The compound of any one of the above (97) to (102), wherein y is 0 or 1.
(104) The compound of the above (103), wherein y is 0.
(105) The compound of any one of the above (97) to (104), wherein R is $(C_1\text{-}C_6)$alkyl, wherein said alkyl is unsubstituted or substituted with phenyl, (5- or 6-membered)heterocycloalkyl, (5- or 6-membered)heterocycloalkenyl or (5- or 6-membered)heteroaryl.
(106) The compound of any one of the above (97) to (104), wherein R is unsubstituted $(C_1\text{-}C_6)$alkyl.
(107) The compound of the above (106), wherein R is unsubstituted $(C_1\text{-}C_4)$alkyl.
(108) The compound of the above (107), wherein R is methyl or ethyl.
(109) The compound of the above (107), wherein R is methyl.
(110) The compound of any one of the above (97) to (104), wherein R is $(C_1\text{-}C_6)$alkyl, wherein said alkyl is substituted with phenyl, (5- or 6-membered)heterocycloalkyl, (5- or 6-membered)heterocycloalkenyl or (5- or 6-membered)heteroaryl.
(111) The compound of any one of the above (97) to (104), wherein R is $(C_1\text{-}C_6)$alkyl substituted with phenyl.
(112) The compound of the above (111), wherein R is $(C_1\text{-}C_4)$alkyl.
(113) The compound of the above (112), wherein R is methyl.
(114) The compound of any one of the above (97) to (104), wherein R is $(C_1\text{-}C_6)$alkyl substituted with (5- or 6-membered)heterocycloalkyl or (5- or 6-membered) heterocycloalkenyl.
(115) The compound of the above (114), wherein R is $(C_1\text{-}C_4)$alkyl.
(116) The compound of the above (114), wherein R is methyl.

(117) The compound of any one of the above (114) to (116), wherein said heterocycloalkenyl is a 5-membered heterocycloalkenyl.
(118) The compound of any one of the above (114) to (116), wherein said heterocycloalkenyl is a 6-membered heterocycloalkenyl.
(119) The compound of the above (117), wherein the 5-membered heterocycloalkenyl is 1,3-dioxolyl.
(120) The compound of any one of the above (97) to (104), wherein R is $(C_1-C_6)$alkyl substituted with (5- or 6-membered)heteroaryl.
(121) The compound of the above (120), wherein R is $(C_1-C_4)$alkyl.
(122) The compound of the above (120), wherein R is methyl.
(123) The compound of any one of the above (120) to (122), wherein said heteroaryl is a 5-membered heteroaryl.
(124) The compound of the above (123), wherein the 5-membered heteroaryl is oxazolyl.
(125) The compound of any one of the above (120) to (122), wherein said heteroaryl is a 6-membered heteroaryl.
(126) The compound of the above (125), wherein the 6-membered heteroaryl is pyridinyl.
(127) The compound of any one of the above (97) to (104), wherein R is $(C_5-C_7)$cycloalkyl.
(128) The compound of the above (127), wherein R is cyclopentyl.
(129) The compound of any one of the above (111) to (113), wherein said phenyl is unsubstituted.
(130) The compound of any one of the above (111) to (113), wherein said phenyl is substituted with 1, 2 or 3 substituent(s) independently selected from halo, $(C_1-C_6)$alkyl and $(C_1-C_6)$alkoxy.
(131) The compound of the above (130), wherein said phenyl is substituted with a substituent selected from F, Cl, methoxy or propanyl.
(132) The compound of any one of the above (114) to (119), wherein said heterocycloalkyl or heterocycloalkenyl is unsubstituted.
(133) The compound of any one of the above (114) to (119), wherein said heterocycloalkyl or heterocycloalkenyl is substituted with 1 or 2 substituent(s) independently selected from oxo and $(C_1-C_6)$alkyl.
(134) The compound of any one of the above (114) to (119), wherein said heterocycloalkyl or heterocycloalkenyl is substituted with 1 or 2 substituent(s) independently selected from oxo and methyl.
(135) The compound of any one of the above (120) to (126), wherein said heteroaryl is unsubstituted.
(136) The compound of any one of the above (120) to (126), wherein said heteroaryl is substituted with 1 or 2 substituent(s) selected from $(C_1-C_6)$alkyl.
(137) The compound of the above (136), wherein said substituent is methyl.
(138) A compound, which is selected from:
N-(Benzyloxy)-2-methanesulfonylbenzene-1-sulfonamide;
2-Methanesulfonyl-N-methoxybenzene-1-sulfonamide;
4-[(2-Methanesulfonylbenzenesulfonamidooxy)methyl] phenyl acetate;
N-[(4-Hydroxyphenyl)methoxy]-2-methanesulfonylbenzene-1-sulfonamide;
2-methanesulfonyl-N-[(5-methyl-2-oxo-2H-1,3-dioxol-4-yl)methoxy]benzene-1-sulfonamide;
2-(2-Methanesulfonylbenzenesulfonamidooxy)ethyl 2,2-dimethylpropanoate;
2-methanesulfonyl-N-{[4-(trifluoromethyl)phenyl] methoxy}benzene-1-sulfonamide;
N-[(4-fluorophenyl)methoxy]-2-methanesulfonylbenzene-1-sulfonamide;
N-[(2-Chlorophenyl)methoxy]-2-methanesulfonylbenzene-1-sulfonamide;
N-[(3-Chlorophenyl)methoxy]-2-methanesulfonylbenzene-1-sulfonamide;
N-[(4-Chlorophenyl)methoxy]-2-methanesulfonylbenzene-1-sulfonamide;
2-Methanesulfonyl-N-[(4-methylphenyl)methoxy]benzene-1-sulfonamide;
2-Methyl-N-[(3-methylphenyl)methoxy]benzene-1-sulfonamide;
2-Methanesulfonyl-N-(pyridin-2-ylmethoxy)benzene-1-sulfonamide;
2-Methanesulfonyl-N-(pyridin-3-ylmethoxy)benzene-1-sulfonamide;
2-Methanesulfonyl-N-[(2-methoxyphenyl)methoxy]benzene-1-sulfonamide;
2-Methanesulfonyl-N-[(3-methoxyphenyl)methoxy]benzene-1-sulfonamide;
2-Methanesulfonyl-N-[(4-methoxyphenyl)methoxy]benzene-1-sulfonamide;
2-methanesulfonyl-N-{[4-(morpholine-4-sulfonyl)phenyl] methoxy}benzene-1-sulfonamide;
2-Methanesulfonyl-N-{[2-(trifluoromethyl)phenyl] methoxy}benzene-1-sulfonamide;
2-Methanesulfonyl-N-{[4-(trifluoromethoxy)phenyl] methoxy}benzene-1-sulfonamide;
2-Methanesulfonyl-N-(2-phenylethoxy)benzene-1-sulfonamide;
2-Methanesulfonyl-N-(1-phenylethoxy)benzene-1-sulfonamide;
N-[(4-Fluorophenyl)methoxy]-3-methanesulfonylbenzene-1-sulfonamide;
3-Methanesulfonyl-N-[(5-methyl-2-oxo-2H-1,3-dioxol-4-yl)methoxy]benzene-1-sulfonamide;
N-(Benzyloxy)-3-methanesulfonylbenzene-1-sulfonamide;
3-Methanesulfonyl-N-methoxybenzene-1-sulfonamide;
2-Methanesulfonyl-N-{[3-(trifluoromethoxy)phenyl] methoxy}benzene-1-sulfonamide;
2-Methanesulfonyl-N-{[3-(trifluoromethyl)phenyl] methoxy}benzene-1-sulfonamide;
N-(2H-1,3-Benzodioxol-5-ylmethoxy)-2-methanesulfonylbenzene-1-sulfonamide;
2-Methanesulfonyl-N-[(4-methanesulfonylphenyl) methoxy]benzene-1-sulfonamide;
2-Methanesulfonyl-N-[(2-methylphenyl)methoxy]benzene-1-sulfonamide;
2-Methanesulfonyl-N-(oxan-2-yloxy)benzene-1-sulfonamide;
N-[(4-Chlorophenyl)methoxy]-3-methanesulfonylbenzene-1-sulfonamide;
3-Methanesulfonyl-N-[(4-methoxyphenyl)methoxy]benzene-1-sulfonamide;
N-[(3-Fluorophenyl)methoxy]-2-methanesulfonylbenzene-1-sulfonamide;
2-Methanesulfonyl-N-{[2-(trifluoromethoxy)phenyl] methoxy}benzene-1-sulfonamide;
2-Methanesulfonyl-N-(propan-2-yloxy)benzene-1-sulfonamide;
N-Ethoxy-2-methanesulfonylbenzene-1-sulfonamide;
N-(tert-Butoxy)-2-methanesulfonylbenzene-1-sulfonamide;
4-[(2-Methanesulfonylbenzenesulfonamidooxy)methyl]-N,N-bis(2-methoxyethyl)benzamide;

N-[(2-Fluorophenyl)methoxy]-2-methanesulfonylbenzene-1-sulfonamide;
N-(Benzyloxy)-4-methanesulfonylbenzene-1-sulfonamide;
2-Methanesulfonyl-N-[(2-phenylpropan-2-yl)oxy]benzene-1-sulfonamide;
N-[(3,5-Dibromo-2-hydroxyphenyl)methoxy]-2-methanesulfonylbenzene-1-sulfonamide;
5-[(Benzyloxy)sulfamoyl]-4-chloro-2-[(furan-2-ylmethyl)amino]benzoic acid;
N-(Benzyloxy)-5-[(benzyloxy)sulfamoyl]-4-chloro-2-[(furan-2-ylmethyl)amino]benzamide;
3-Methanesulfonyl-N-[(2-methoxyphenyl)methoxy]benzene-1-sulfonamide;
3-Methanesulfonyl-N-{[4-(1H-pyrazol-1-yl)phenyl]methoxy}benzene-1-sulfonamide;
3-Methanesulfonyl-N-(pyridin-2-ylmethoxy)benzene-1-sulfonamide;
3-Methanesulfonyl-N-{[4-(propan-2-yl)phenyl]methoxy}benzene-1-sulfonamide;
3-Methanesulfonyl-N-[(3-methoxyphenyl)methoxy]benzene-1-sulfonamide;
3-Methanesulfonyl-N-{[5-(trifluoromethyl)furan-2-yl]methoxy}benzene-1-sulfonamide;
N-(Cyclopentyloxy)-2-methanesulfonylbenzene-1-sulfonamide;
N-(Cyclopentyloxy)-3-methanesulfonylbenzene-1-sulfonamide;
N-[(4-tert-Butylphenyl)methoxy]-3-methanesulfonylbenzene-1-sulfonamide;
N-(Benzyloxy)-3-(trifluoromethyl)benzene-1-sulfonamide;
N-[(Dimethyl-1,2-oxazol-4-yl)methoxy]-3-methanesulfonylbenzene-1-sulfonamide;
N-{4-[(3-Methanesulfonylbenzenesulfonamidooxy)methyl]phenyl}acetamide;
N-(2,1,3-Benzoxadiazol-5-ylmethoxy)-3-methanesulfonylbenzene-1-sulfonamide;
N-[(2-Chlorophenyl)methoxy]-3-methanesulfonylbenzene-1-sulfonamide;
3-Methanesulfonyl-N-(pyridin-3-ylmethoxy)benzene-1-sulfonamide;
4-[(3-Methanesulfonylbenzenesulfonamidooxy)methyl]-N,N-bis(2-methoxyethyl)benzene-1-sulfonamide; and
2-Methanesulfonylbenzenesulfonamido pyrazine-2-carboxylate;
or a pharmaceutically acceptable salt thereof.
(139) A compound, which is:
2-methanesulfonyl-N-[(5-methyl-2-oxo-2H-1,3-dioxol-4-yl)methoxy]benzene-1-sulfonamide; or
pharmaceutically acceptable salt thereof.
(140) A compound, which is:
3-Methanesulfonyl-N-[(5-methyl-2-oxo-2H-1,3-dioxol-4-yl)methoxy]benzene-1-sulfonamide; or
pharmaceutically acceptable salt thereof.
(141) A compound, which is selected from:
N-(Benzyloxy)-4-methylpiperazine-1-sulfonamide;
N-(Benzyloxy)-5-(morpholine-4-carbonyl)thiophene-2-sulfonamide;
N-Methoxy-5-(morpholine-4-carbonyl)thiophene-2-sulfonamide;
N-(Benzyloxy)-3-chlorothiophene-2-sulfonamide;
3-Chloro-N-methoxythiophene-2-sulfonamide;
N-(Benzyloxy)pyridine-2-sulfonamide;
4-(Methoxysulfamoyl)-N-(propan-2-yl)thiophene-2-carboxamide;
4-[(Benzyloxy)sulfamoyl]-N-(propan-2-yl)thiophene-2-carboxamide;
2-[(Benzyloxy)sulfamoyl]pyridin-1-ium-1-olate;
5-(Methoxysulfamoyl)-N-(propan-2-yl)thiophene-2-carboxamide;
5-[(Benzyloxy)sulfamoyl]-N-(propan-2-yl)thiophene-2-carboxamide;
3-[(Benzyloxy)sulfamoyl]pyridin-1-ium-1-olate; and
3-(Methoxysulfamoyl)pyridin-1-ium-1-olate;
or a pharmaceutically acceptable salt thereof.
(142) A compound, which is
N-(Benzyloxy)-4-methylpiperazine-1-sulfonamide;
N-(Benzyloxy)-5-(morpholine-4-carbonyl)thiophene-2-sulfonamide;
N-Methoxy-5-(morpholine-4-carbonyl)thiophene-2-sulfonamide;
N-(Benzyloxy)-3-chlorothiophene-2-sulfonamide;
N-(Benzyloxy)pyridine-2-sulfonamide;
4-(Methoxysulfamoyl)-N-(propan-2-yl)thiophene-2-carboxamide;
4-[(Benzyloxy)sulfamoyl]-N-(propan-2-yl)thiophene-2-carboxamide;
2-[(Benzyloxy)sulfamoyl]pyridin-1-ium-1-olate;
5-(Methoxysulfamoyl)-N-(propan-2-yl)thiophene-2-carboxamide; and
5-[(Benzyloxy)sulfamoyl]-N-(propan-2-yl)thiophene-2-carboxamide;
or a pharmaceutically acceptable salt thereof.
(143) A compound, which is selected from:
N-[(4-Fluorophenyl)methoxy]-1-benzofuran-2-sulfonamide;
N-[(5-Methyl-2-oxo-2H-1,3-dioxol-4-yl)methoxy]-1-benzofuran-2-sulfonamide;
N-[(4-Chlorophenyl)methoxy]-1-benzofuran-2-sulfonamide;
N-[(4-Methoxyphenyl)methoxy]-1-benzofuran-2-sulfonamide;
N-[(2-Chlorophenyl)methoxy]-1-benzofuran-2-sulfonamide;
N-(Pyridin-2-ylmethoxy)-1-benzofuran-2-sulfonamide;
N-[(2-Methoxyphenyl)methoxy]-1-benzofuran-2-sulfonamide;
N-{[4-(Propan-2-yl)phenyl]methoxy}-1-benzofuran-2-sulfonamide;
N-(Cyclopentyloxy)-1-benzofuran-2-sulfonamide;
N-[(3-Methoxyphenyl)methoxy]-1-benzofuran-2-sulfonamide;
N-[(Dimethyl-1,2-oxazol-4-yl)methoxy]-1-benzofuran-2-sulfonamide;
N-[(5-Methyl-1,2-oxazol-3-yl)methoxy]-1-benzofuran-2-sulfonamide;
N,6-Dimethoxy-1-benzofuran-2-sulfonamide;
N-(Benzyloxy)-6-methoxy-1-benzofuran-2-sulfonamide;
N-(Benzyloxy)-6-chloro-1-benzofuran-2-sulfonamide;
6-Chloro-N-methoxy-1-benzofuran-2-sulfonamide;
N-(Pyridin-3-ylmethoxy)-1-benzofuran-2-sulfonamide;
or a pharmaceutically acceptable salt thereof.
(144) A compound, which is:
N-[(5-Methyl-2-oxo-2H-1,3-dioxol-4-yl)methoxy]-1-benzofuran-2-sulfonamide; or a
pharmaceutically acceptable salt thereof.
(145) A pharmaceutical composition comprising the compound of any one of the above (1) to
(144), and at least one pharmaceutically acceptable excipient.

(146) A method of treating a cardiovascular disease, comprising administering an effective amount of the compound of any one of the above (1) to (144) to a patient in need thereof.
(147) The method of the above (146), wherein the cardiovascular disease is heart failure.
(148) The method of the above (146), wherein the cardiovascular disease is acute decompensated heart failure.
(149) Use of the compound of any one of the above (1) to (144) or the pharmaceutical composition of the above (145) for the manufacture of a medicament useful for treating a cardiovascular disease.
(150) Use of the compound of any one of the above (1) to (144) or the pharmaceutical composition of the above (145) for the manufacture of a medicament useful for treating heart failure.
(151) Use of the compound of any one of the above (1) to (144) or the pharmaceutical composition of the above (145) for the manufacture of a medicament useful for treating acute decompensated heart failure.
(152) The use of any one of the above (149) to (151), wherein the compound or the pharmaceutical composition is administered orally.
(153) The compound of any one of the above (1) to (144) or the pharmaceutical composition of any one of the above (145) for use in the treatment of a cardiovascular disease.
(154) The compound of any one of the above (1) to (144) or the pharmaceutical composition of any one of the above (145) for use in the treatment of heart failure.
(155) The compound of any one of the above (1) to (144) or the pharmaceutical composition of any one of the above (145) for use in the treatment of acute decompensated heart failure.
(156) A kit for treating and/or preventing a disease or condition responsive to nitroxyl therapy comprising a compound of any one of the above (1) to (144), or a pharmaceutical composition of the above (145); and instructions for use of the kit.
(157) The kit of the above (156), wherein the disease or condition is selected from cardiovascular diseases, ischemia/reperfusion injury, cancerous disease, and pulmonary hypertension.
(158) The kit of the above (157), wherein the cardiovascular disease is heart failure.

3.1 Definitions

Unless clearly indicated otherwise, the following terms as used herein have the meanings indicated below.

A "pharmaceutically acceptable salt" refers to a salt of any therapeutic agent disclosed herein, which salt can include any of a variety of organic and inorganic counter ions known in the art and which salt is pharmaceutically acceptable. When the therapeutic agent contains an acidic functionality, various exemplary embodiments of counter ions are sodium, potassium, calcium, magnesium, ammonium, tetraalkylammonium, and the like. When the therapeutic agent contains a basic functionality, a pharmaceutically acceptable salt can include as a counter ion, by way of example, an organic or inorganic acid, such as hydrochloride, hydrobromide, tartrate, mesylate, acetate, maleate, oxalate, and the like. Illustrative salts include, but are not limited to, sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt can be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower-alkyl amines), such as mono-, bis-, or tris-(2-hydroxyethyl)amine, 2-hydroxy-tert-butylamine, or tris-(hydroxymethyl)methylamine, N,N-di-lower-alkyl-N-(hydroxy-lower-alkyl)-amines, such as N,N-dimethyl-N-(2-hydroxyethyl) amine, or tri-(2-hydroxyethyl)amine; N-methyl-D-glucamine; and amino acids such as arginine, lysine, and the like. A salt can also be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

"Pharmaceutically acceptable excipient" refers to any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Gennaro, Ed., *Remington: The Science and Practice of Pharmacy*, $20^{th}$ Ed. (Lippincott Williams & Wilkins, Baltimore, Md., 2000) and *Handbook of Pharmaceutical Excipients*, American Pharmaceutical Association, Washington, D.C., (e.g., $1^{st}$, $2^{nd}$ and $3^{rd}$ Eds., 1986, 1994 and 2000, respectively). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose, (2) starches, such as corn starch and potato starch, (3) cellulose and its derivatives, such as sodium carboxymethyl cellulose, ethyl cellulose, cellulose acetate, hydroxypropylmethylcellulose, hydroxypropylcellulose, microcrystalline cellulose, and croscarmellose, such as or croscarmellose sodium, (4) powdered tragacanth, (5) malt, (6) gelatin, (7) talc, (8) excipients, such as cocoa butter and suppository waxes, (9) oils, such as peanut oil, cottonseed oil, safflower oil, sesame oil, olive oil, corn oil and soybean oil, (10) glycols, such as propylene glycol, (11) polyols, such as glycerin, sorbitol, mannitol and polyethylene glycol, (12) esters, such as ethyl oleate and ethyl laurate, (13) agar, (14) buffering agents, such as magnesium hydroxide and aluminum hydroxide, (15) alginic acid, (16) pyrogen-free water, (17) isotonic saline, (18) Ringer's solution, (19) ethyl alcohol, (20) pH buffered solutions, (21) polyesters, polycarbonates and/or polyanhydrides, and (22) other non-toxic compatible substances employed in pharmaceutical formulations.

"Unit dosage form" refers to a physically discrete unit suitable as a unitary dosage for a human or an animal. Each unit dosage form can contain a predetermined amount of a therapeutic agent calculated to produce a desired effect.

Unless clearly indicated otherwise, a "patient" refers to an animal, such as a mammal, including but not limited to a human. Hence, the methods disclosed herein can be useful in human therapy and veterinary applications. In particular embodiments, the patient is a mammal. In certain embodiments, the patient is a human.

"Effective amount" refers to such amount of a therapeutic agent or a pharmaceutically acceptable salt thereof, which in combination with its parameters of efficacy and potential for toxicity, as well as based on the knowledge of the practicing specialist, should be effective in a given therapeutic form. As is understood in the art, an effective amount can be administered in one or more doses.

"Treatment", "treating" and the like is an approach for obtaining a beneficial or desired result, including clinical results. For purposes of this disclosure, beneficial or desired results include but are not limited to inhibiting and/or suppressing the onset and/or development of a condition or reducing the severity of such condition, such as reducing the number and/or severity of symptoms associated with the condition, increasing the quality of life of those suffering from the condition, decreasing the dose of other medications required to treat the condition, enhancing the effect of another medication a patient is taking for the condition, and/or prolonging survival of patients having the condition.

"Prevent", "preventing" and the like refers to reducing the probability of developing a condition in a patient who does not have, but is at risk of developing a condition. A patient "at risk" may or may not have a detectable condition, and may or may not have displayed a detectable condition prior to the treatment methods disclosed herein. "At risk" denotes that a patient has one or more so-called risk factors, which are measurable parameters that correlate with development of a condition and are known in the art. A patient having one or more of these risk factors has a higher probability of developing the condition than a patient without such risk factor(s).

"Positive inotrope" refers to an agent that causes an increase in myocardial contractile function. Exemplary positive inotropes are a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds are also included within positive inotropes. For example, U.S. Pat. No. 4,663,351 discloses a dobutamine prodrug that can be administered orally.

A condition that is "responsive to nitroxyl therapy" includes any condition in which administration of a compound that donates an effective amount of nitroxyl under physiological conditions treats and/or prevents the condition, as those terms are defined herein. A condition whose symptoms are suppressed or diminished upon administration of nitroxyl donor is a condition responsive to nitroxyl therapy.

"Pulmonary hypertension" or "PH" refers to a condition in which the pulmonary arterial pressure is elevated. The current hemodynamic definition of PH is a mean pulmonary arterial pressure ("MPAP") at rest of greater than or equal to 25 mmHg. Badesch et al., *J. Amer. Coll. Cardiol.* 54 (Suppl.):S55-S66 (2009).

"N/A" means not assessed.

"$(C_1-C_6)$alkyl" refers to saturated linear and branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_6)$alkyl groups include methyl, ethyl, n-propyl, iso-propyl, n-butyl, tert-butyl, n-hexyl, and the like.

"$(C_1-C_4)$alkyl" refers to saturated linear and branched hydrocarbon structures having 1, 2, 3, or 4 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_4)$alkyl groups include methyl, ethyl, n-propyl, iso-propyl, n-butyl, tert-butyl, and the like.

"$(C_3-C_6)$cycloalkyl" refers to a saturated cyclic hydrocarbon containing 3, 4, 5, or 6 ring carbon atoms. Examples of $(C_3-C_6)$cycloalkyl groups include cyclopropyl, cyclobutyl, cyclopentyl, cyclohexyl, and the like.

"$(C_1-C_4)$perhaloalkyl" refers to a $(C_1-C_4)$alkyl group wherein every hydrogen atom is replaced by halo, each halo being independently selected. Examples of $(C_1-C_4)$perhaloalkyl groups include —$CF_3$, —$CCl_3$, —$CF_2CF_3$, —$CCl_2CF_3$, —$CClFCClF_2$, —$CF(CF_3)_2$, —$CBr(CF_3)(CFCl_2)$, and the like.

"$(C_1-C_4)$haloalkyl" refers to a $(C_1-C_4)$alkyl group wherein at least one hydrogen atom is replaced by halo but wherein the $(C_1-C_4)$haloalkyl contains few halos than a $(C_1-C_4)$perhaloalkyl having the same number of carbon atoms as the $(C_1-C_4)$haloalkyl. Each halo of a $(C_1-C_4)$ haloalkyl is independently selected. Examples of $(C_1-C_4)$ haloalkyl groups include —$CHF_2$, —$CH_2F$, —$CHFCl$, —$CH_2CF_3$, —$CHClCHF_2$, —$CHFCHClF$, —$CH(CF_3)_2$, —$CH(CF_3)(CH_3)$, —$CBr(CHF_2)(CHCl_2)$, and the like.

"$(C_1-C_6)$alkoxy" refers to —O—$(C_1-C_6)$alkyl. Examples of $(C_1-C_6)$alkoxy groups include methoxy, ethoxy, propoxy, n-propoxy, iso-propoxy, butoxy, n-butoxy, sec-butoxy, tert-butoxy, pentoxy, hexyloxy, and the like.

"$(C_1-C_4)$alkoxy" refers to —O—$(C_1-C_4)$alkyl. Examples of $(C_1-C_4)$alkoxy groups include methoxy, ethoxy, propoxy, n-propoxy, iso-propoxy, butoxy, n-butoxy, sec-butoxy, tert-butoxy, and the like.

"$(C_1-C_4)$haloalkoxy" refers to —O—$(C_1-C_4)$haloalkyl. Examples of $(C_1-C_4)$haloalkoxy groups include —$OCHF_2$, —$OCH_2F$, —$OCHFCl$, —$OCH_2CF_3$, —$OCHClCHF_2$, —$OCHFCHClF$, —$OCH(CF_3)_2$, —$OCH(CF_3)(CH_3)$, —$OCBr(CHF_2)(CHCl_2)$, and the like.

"$(C_1-C_4)$perhaloalkoxy" refers to —O—$(C_1-C_4)$perhaloalkyl. Examples of $(C_1-C_4)$perhaloalkoxy groups include —$OCF_3$, —$OCCl_3$, —$OCF_2CF_3$, —$OCCl_2CF_3$, —$OClFCClF_2$, —$OCF(CF_3)_2$, —$OCBr(CF_3)(CFCl_2)$, and the like.

"$(C_1-C_6)$alkylsulfanyl" refers to —S—$(C_1-C_6)$alkyl. Examples of $(C_1-C_6)$alkylsulfanyl groups include methylsulfanyl, ethylsulfanyl, propylsulfanyl, n-propylsulfanyl, iso-propylsulfanyl, butylsulfanyl, n-butylsulfanyl, sec-butylsulfanyl, tert-butylsulfanyl, pentylsulfanyl, hexylsulfanyl, and the like.

"$(C_1-C_4)$haloalkylsulfanyl" refers to —S—$(C_1-C_4)$haloalkyl. Examples of $(C_1-C_4)$haloalkylsulfanyl groups include —SCHF$_2$, —SCH$_2$F, —SCHFCl, —SCH$_2$CF$_3$, —SCHClCHF$_2$, —SCHFCHClF, —SCH(CF$_3$)$_2$, —SCH(CF$_3$)(CH$_3$), —SCBr(CHF$_2$)(CHCl$_2$), and the like.

"$(C_1-C_4)$perhaloalkylsulfanyl" refers to —S—$(C_1-C_4)$perhaloalkyl. Examples of $(C_1-C_4)$perhaloalkylsulfanyl groups include —SCF$_3$, —SCCl$_3$, —SCF$_2$CF$_3$, —SCCl$_2$CF$_3$, —SCClFCClF$_2$, —SCF(CF$_3$)$_2$, —SCBr(CF$_3$)(CFCl$_2$), and the like.

"$(C_1-C_6)$alkylsulfinyl" refers to —S(O)—$(C_1-C_6)$alkyl. Examples of $(C_1-C_6)$alkylsulfinyl groups include methylsulfinyl, ethylsulfinyl, propylsulfinyl, n-propylsulfinyl, iso-propylsulfinyl, butylsulfinyl, n-butylsulfinyl, sec-butylsulfinyl, tert-butylsulfinyl, pentylsulfinyl, hexylsulfinyl, and the like.

"$(C_1-C_6)$alkylsulfonyl" refers to —S(O)$_2$—$(C_1-C_6)$alkyl. Examples of $(C_1-C_6)$alkylsulfonyl groups include methylsulfonyl, ethylsulfonyl, propylsulfonyl, n-propylsulfonyl, iso-propylsulfonyl, butylsulfonyl, n-butylsulfonyl, sec-butylsulfonyl, tert-butylsulfonyl, pentylsulfonyl, hexylsulfonyl, and the like.

"$(C_3-C_6)$cycloalkylsulfonyl" refers to —S(O)$_2$—$(C_3-C_6)$cycloalkyl. Examples of $(C_3-C_6)$cycloalkylsulfonyl groups include —S(O)$_2$-cyclopropyl, —S(O)$_2$-cyclobutyl, —S(O)$_2$-cyclopentyl, —S(O)$_2$-cyclohexyl, and the like.

"$(C_1-C_4)$perhaloalkylsulfinyl" refers to —S(O)—$(C_1-C_4)$perhaloalkyl. Examples of $(C_1-C_4)$perhaloalkylsulfinyl groups include —S(O)—CF$_3$, —S(O)—CCl$_3$, —S(O)—CF$_2$CF$_3$, —S(O)—CCl$_2$CF$_3$, —S(O)—CClFCClF$_2$, —S(O)—CClFCClF$_2$, —S(O)—CClFCClF$_2$, —S(O)—CF(CF$_3$)$_2$, —S(O)—CBr(CF$_3$)(CFCl$_2$), and the like.

"$(C_1-C_4)$perhaloalkylsulfonyl" refers to —S(O)$_2$—$(C_1-C_4)$perhaloalkyl. Examples of $(C_1-C_4)$perhaloalkylsulfonyl groups include —S(O)$_2$—CF$_3$, —S(O)$_2$—CCl$_3$, —S(O)$_2$—CF$_2$CF$_3$, —S(O)$_2$—CCl$_2$CF$_3$, —S(O)$_2$—CClFCClF$_2$, —S(O)$_2$—CClFCClF$_2$, —S(O)$_2$—CClFCClF$_2$, —S(O)$_2$—CF(CF$_3$)$_2$, —S(O)$_2$—CBr(CF$_3$)(CFCl$_2$), and the like.

"$(C_1-C_4)$haloalkylsulfinyl" refers to —S(O)—$(C_1-C_4)$haloalkyl. Examples of $(C_1-C_4)$haloalkylsulfinyl groups include —S(O)—CHF$_2$, —S(O)—CH$_2$F, —S(O)—CHFCl, —S(O)—CH$_2$CF$_3$, —S(O)—CHClCHF$_2$, —S(O)—CHFCHClF, —S(O)—CH(CF$_3$)$_2$, —S(O)—CH(CF$_3$)(CH$_3$), —S(O)—CBr(CHF$_2$)(CHCl$_2$), and the like.

"$(C_1-C_4)$haloalkylsulfonyl" refers to —S(O)$_2$—$(C_1-C_4)$haloalkyl. Examples of $(C_1-C_4)$haloalkylsulfonyl groups include —S(O)$_2$—CHF$_2$, —S(O)$_2$—CH$_2$F, —S(O)$_2$—CHFCl, —S(O)$_2$—CH$_2$CF$_3$, —S(O)$_2$—CHClCHF$_2$, —S(O)$_2$—CHFCHClF, —S(O)$_2$—CH(CF$_3$)$_2$, —S(O)$_2$—CH(CF$_3$)(CH$_3$), —S(O)$_2$—CBr(CHF$_2$)(CHCl$_2$), and the like.

"N—$(C_1-C_6)$alkylaminosulfonyl" refers to —S(O)$_2$—NH—$(C_1-C_6)$alkyl. Examples of N—$(C_1-C_6)$alkylaminosulfonyl groups include —S(O)$_2$—NH-methyl, —S(O)$_2$—NH-ethyl, —S(O)$_2$—NH-n-propyl, —S(O)$_2$—NH-iso-propyl, —S(O)$_2$—NH-n-butyl, —S(O)$_2$—NH-sec-butyl, —S(O)$_2$—NH-iso-butyl, —S(O)$_2$—NH-tert-butyl, —S(O)$_2$—NH-n-hexyl, and the like.

"N,N-di$(C_1-C_6)$alkylaminosulfonyl" refers to —S(O)$_2$—N—$((C_1-C_6)$alkyl$)_2$ wherein each $(C_1-C_6)$alkyl is independently selected. Examples of N,N-di$(C_1-C_6)$alkylaminosulfonyl groups include —S(O)$_2$—N(methyl)$_2$, —S(O)$_2$—N(methyl)(ethyl), —S(O)$_2$—N(ethyl)$_2$, —S(O)$_2$—N(methyl)(n-propyl), —S(O)$_2$—N(ethyl)(iso-propyl), —S(O)$_2$—N(methyl)(n-butyl), —S(O)$_2$—N(ethyl)(sec-butyl), —S(O)$_2$—N(iso-propyl)(iso-butyl), —S(O)$_2$—N(tert-butyl)$_2$, —S(O)$_2$—N(methyl)(n-hexyl), and the like.

"(5- or 6-membered)heterocycloalkyl" refers to a 5- or 6-membered, saturated, monocyclic-heterocycle containing 1, 2, 3, or 4 ring heteroatoms each independently selected from nitrogen, oxygen, and sulfur, wherein said nitrogen and sulfur heteroatoms may optionally be oxidized and the nitrogen heteroatom may optionally be quaternized. A heterocycloalkyl group can be attached to the parent structure through a carbon or a heteroatom. Examples of (5- or 6-membered)heterocycloalkyl groups include pyrrolidinyl, piperidinyl, piperazinyl, tetrahydro-oxazinyl, tetrahydrofuranyl, thiolanyl, dithiolanyl, pyrazolidinyl, imidazolidinyl, tetrahydrofuranone, γ-butyrolactone, dioxolanyl, tetrahydropyranyl, dioxanyl, dihydrothiophenyl, morpholinyl, thiomorpholinyl, tetrahydro-oxazinyl, 1,2,3-triazinanyl, and the like.

"(5- or 6-membered)heterocycloalkenyl" refers to a 5- or 6-membered, partially unsaturated, monocyclic-heterocycle containing 1, 2, 3, or 4 ring heteroatoms each independently selected from nitrogen, oxygen, and sulfur, wherein said nitrogen and sulfur heteroatoms may optionally be oxidized and the nitrogen heteroatom may optionally be quaternized. A heterocycloalkenyl group can be attached to the parent structure through a carbon or a heteroatom. Examples of (5- or 6-membered)heterocycloalkenyl groups include pyrrolinyl, pyrazolinyl, imidazolinyl, 2H-pyranyl, 4H-pyranyl, 2H-thiopyranyl, 4H-thiopyranyl, 2,3-dihydrothiophenyl, 2,3-dihydrofuranyl, oxazinyl, 2,3-dihydro-1,4-dioxinyl, 1,3-dioxolyl, 1,3-dioxol-2-one and the like "(5- or 6-membered)heteroaryl" refers to a monocyclic aromatic heterocycle ring of 5 or 6 members, i.e., a monocyclic aromatic ring comprising at least one ring heteroatom, e.g., 1, 2, 3, or 4 ring heteroatoms, each independently selected from nitrogen, oxygen, and sulfur. When the (5- or 6-membered)heteroaryl comprises a nitrogen or sulfur atom(s), the nitrogen atom or sulfur atom(s) are optionally oxidized to form the N-oxide or S-oxide(s). A (5- or 6-membered)heteroaryl group can be attached to the parent structure through a carbon or heteroatom. Examples of (5- or 6-membered)heteroaryls include pyridyl, pyrrolyl, pyrazolyl, furyl, imidazolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, thienyl, and the like.

"$(C_6-C_{10})$aryl" refers to a monovalent aromatic hydrocarbon group which may be monocyclic, bicyclic or tricyclic, wherein at least one ring in the system is aromatic and wherein each ring in the system contains 3, 4, 5, 6 or 7 ring members. Examples of $(C_6-C_{10})$aryl groups include without limitation phenyl, naphthyl, indanyl, indenyl and tetralinyl. In some embodiments, the aryl is phenyl.

Unless clearly indicated otherwise, each substituent of a "substituted phenyl", "phenyl substituted with 1, 2, or 3 independently selected substituent(s)", "monosubstituted phenyl", "disubstituted phenyl", "trisubstituted phenyl", and the like is independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, C(=O)OH, C(=O)O$(C_1-C_6)$alkyl, C(=O)NR$^4$R$^5$, C(=O)—$(C_5-C_7)$heterocycloalkyl, $(C_5-C_7)$heterocycloalkyl, $(C_1-C_6)$alkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$NH$_2$, S(O)$_2$—NR$^6$R$^7$, S(O)$_2$-phenyl, S(O)$_2$—$(C_5-C_7)$heterocycloalkyl, S(=O)(=NR)$(C_1-C_6)$alkyl, NR$^4$R$^5$, N—(C$_1$-C$_6$)alkylaminosulfonyl, and N,N-di(C$_1$-C$_6$)alkylaminosulfonyl, wherein said (C$_5$-C$_7$)heterocycloalkyl is unsubstituted or substituted with 1 or 2 substituent(s) independently selected from halo or (C$_1$-C$_6$)alkyl.

"Halo" or "halogen" refers to fluoro (—F), chloro (—Cl), bromo (—Br) and iodo (—I).

A compound of the disclosure can contain one, two, or more asymmetric centers and thus can give rise to enantiomers, diastereomers, and other stereoisomeric forms. The disclosure encompasses compounds with all such possible forms, as well as their racemic and resolved forms or any mixture thereof, unless specifically otherwise indicated. When a compound of the disclosure contains an olefinic double bond, a C=N double bond, or any other center of geometric asymmetry, it is intended to include all "geometric isomers", e.g., both Z and E geometric isomers, unless specifically otherwise indicated. All "tautomers", e.g., amine-imine, enamine-enimine, enamine-imine, urea-isourea, ketone-enol, amide-imidic acid, lactam-lactim, are intended to be encompassed by the disclosure as well unless specifically otherwise indicated.

Unless otherwise stated, structures depicted herein are also meant to include compounds that differ only in the presence of one or more isotopically enriched or isotopically-labeled atoms. Examples of isotopes present in the compounds of the disclosure include isotopes of hydrogen (e.g., $^2$H and $^3$H), carbon (e.g., $^{13}$C and $^{14}$C), nitrogen (e.g., $^{15}$N) and oxygen (e.g., $^{17}$O and $^{18}$O).

3.2 Compounds of the Disclosure

One aspect of the disclosure provides a compound of formula (I):

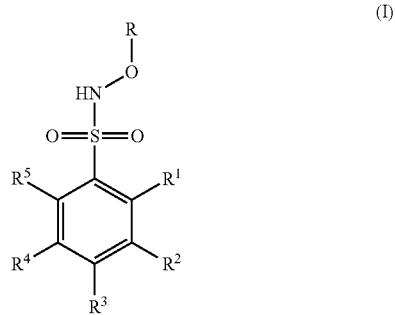

or a pharmaceutically acceptable salt thereof, wherein:
R$^1$ is H, halo, (C$_1$-C$_6$)alkyl, (C$_1$-C$_6$)alkylsulfanyl, (C$_1$-C$_6$)alkylsulfinyl or (C$_1$-C$_6$)alkylsulfonyl;
R$^2$ is H, (C$_1$-C$_6$)alkylsulfanyl, (C$_1$-C$_6$)alkylsulfinyl, (C$_1$-C$_6$)alkylsulfonyl, (C$_1$-C$_6$)haloalkyl or (C$_1$-C$_6$)perhaloalkyl;
R$^3$ is H, (C$_1$-C$_6$)alkylsulfanyl, (C$_1$-C$_6$)alkylsulfinyl, (C$_1$-C$_6$)alkylsulfonyl or NR$^6$R$^7$, wherein
  R$^6$ and R$^7$ are independently selected from H and (C$_1$-C$_6$)alkyl, wherein said alkyl is unsubstituted or substituted with (5- or 6-membered)heteroaryl;
R$^4$ is H, COOH, or CONR$^8$OR$^9$, wherein
  R$^8$ and R$^9$ are independently selected from H and (C$_1$-C$_6$)alkyl, wherein said alkyl is unsubstituted or substituted with phenyl;
R$^5$ is H; and
R is (C$_1$-C$_6$)alkyl, (5- or 6-membered)heterocycloalkyl, (C$_5$-C$_7$)cycloalkyl or C(=O)(5- or 6-membered) heteroaryl, wherein said alkyl is unsubstituted or substituted with a substituent selected from phenyl, (5- or 6-membered)heterocycloalkyl, (5- or 6-membered)heterocycloalkenyl, (5- or 6-membered)heteroaryl, or O(C(=O)(C$_1$-C$_6$)alkyl,
  wherein said phenyl is unsubstituted or substituted with 1, 2, 3, 4 or 5 substituent(s) independently selected from the group consisting of halo, OH, (C$_1$-C$_6$)alkyl, (C$_1$-C$_6$)haloalkyl, (C$_1$-C$_6$)perhaloalkyl, (C$_1$-C$_6$)alkoxy, (C$_1$-C$_6$)haloalkoxy, (C$_1$-C$_6$)perhaloalkoxy, (C$_1$-C$_6$)alkylsulfanyl, (C$_1$-C$_6$)alkylsulfinyl, (C$_1$-C$_6$)alkylsulfonyl, SO$_2$-(5- or 6-membered)heterocycloalkyl, (5- or 6-membered)heteroaryl, OC(=O)(C$_1$-C$_6$)alkyl, NHC(=O) (C$_1$-C$_6$)alkyl, N(C$_1$-C$_6$)alkyl-(C=O) (C$_1$-C$_6$)alkyl, C(=O)NH(C$_1$-C$_6$)alkyl, C(=O)N-di(C$_1$-C$_6$)alkyl, C(=O)NH(C$_1$-C$_6$)alkoxy, C(=O)N-di(C$_1$-C$_6$)alkoxy, N—(C$_1$-C$_6$)alkylaminosulfonyl, N,N-di(C$_1$-C$_6$)alkylaminosulfonyl, N—(C$_1$-C$_6$)alkoxyaminosulfonyl, and N,N-di(C$_1$-C$_6$)alkoxyaminosulfonyl;
  wherein said phenyl is optionally fused to a (5- or 6-membered)heterocycloalkyl or (5- or 6-membered)heteroaryl; and
  wherein said heterocycloalkyl, heterocycloalkenyl and heteroaryl are unsubstituted or substituted with 1, 2 or 3 substituent(s) independently selected from oxo, (C$_1$-C$_6$)alkyl, (C$_1$-C$_6$)haloalkyl, and (C$_1$-C$_6$)perhaloalkyl, provided that:
(1) at least one of R$^1$, R$^2$, R$^3$, R$^4$ and R$^5$ is other than H;
(2) when R$^1$ is halo and R$^2$, R$^3$, R$^4$ and R$^5$ are each H, then R is not unsubstituted benzyl, ethyl, cyclopentyl, pyrrolidinylethyl, piperidinylethyl, morpholinylethyl, furanpropyl, or tetrahydro-2H-pyranyl;
(3) when R$^1$ is methyl, and R$^2$, R$^3$, R$^4$ and R$^5$ are each H, then R is not isobutyl, cyclopentyl, unsubstituted benzyl, pyrrolidinylethyl, piperidinylethyl, morpholinylethyl, furanpropyl, or pyrrolidinyl;
(4) when R$^1$ is methyl or ethyl, and R$^2$, R$^3$, and R$^5$ are each H, and R$^4$ is COOH, then R is not cyclopentyl, ethyl or isobutyl;
(5) when R$^1$ is halo, R$^2$, R$^3$, and R$^5$ are each H, and R$^4$ is COOH, then R is not ethyl, iso-butyl or cyclopentyl;
(6) when R$^3$ is SO$_2$CH$_3$ and R$^1$, R$^2$, R$^4$ and R$^5$ are each H, then R is not ethyl, iso-butyl or cyclopentyl;
(7) when R$^2$ is trifluoromethyl, R$^1$ is H or methyl, and R$^3$, R$^4$ and R$^5$ are each H, then R is not ethyl, iso-butyl or cyclopentyl; and
(8) when R$^3$ is NH$_2$, and R$^1$, R$^2$, R$^4$ and R$^5$ are each H, then R is not 2-propyl.

In one embodiment, R$^1$ is H, halo, or (C$_1$-C$_6$)alkyl. In another embodiment, R$^1$ is H, halo, or (C$_1$-C$_6$)alkylsulfanyl. In another embodiment, R$^1$ is H, halo, or (C$_1$-C$_6$)alkylsulfinyl. In another embodiment, R$^1$ is H, halo, or (C$_1$-C$_6$)alkylsulfonyl. In another embodiment, R$^1$ is halo, (C$_1$-C$_6$)alkyl or (C$_1$-C$_6$)alkylsulfanyl. In another embodiment, R$^1$ is halo, (C$_1$-C$_6$)alkyl or (C$_1$-C$_6$)alkylsulfinyl. In another embodiment, R$^1$ is halo, (C$_1$-C$_6$)alkyl or (C$_1$-C$_6$)alkylsulfonyl. In another embodiment, R$^1$ is (C$_1$-C$_6$)alkyl, (C$_1$-C$_6$)alkylsulfanyl or (C$_1$-C$_6$)alkylsulfinyl. In another embodiment, R$^1$ is (C$_1$-C$_6$)alkyl, (C$_1$-C$_6$)alkylsulfanyl or (C$_1$-C$_6$)alkylsulfonyl. In another embodiment, R$^1$ is (C$_1$-C$_6$)alkylsulfanyl, (C$_1$-C$_6$)alkylsulfinyl or (C$_1$-C$_6$)alkylsulfonyl.

In one embodiment, the present disclosure relates to a compound of formula (I) and the attendant definitions, wherein R$^1$ is H. In one embodiment, R$^1$ is halo. In another embodiment, $R^1$ is chloro. In another embodiment, $R^1$ is bromo. In another embodiment, $R^1$ is fluoro.

In another embodiment, the present disclosure relates to a compound of formula (I) and the attendant definitions, wherein $R^1$ is $(C_1-C_6)$alkyl. In another embodiment, $R^1$ is $(C_1-C_4)$alkyl. In another embodiment, $R^1$ is methyl, ethyl, propyl, or butyl. In another embodiment, $R^1$ is methyl, ethyl, or propyl. In another embodiment, $R^1$ is methyl, ethyl, or butyl. In another embodiment, $R^1$ is methyl, propyl, or butyl. In another embodiment, $R^1$ is ethyl, propyl, or butyl. In another embodiment, $R^1$ is methyl or ethyl. In another embodiment, $R^1$ is methyl or propyl. In another embodiment, $R^1$ is methyl or butyl. In another embodiment, $R^1$ is ethyl or propyl. In another embodiment, $R^1$ is ethyl or butyl. In another embodiment, $R^1$ is propyl or butyl. In another embodiment, $R^1$ is methyl. In another embodiment, $R^1$ is ethyl. In another embodiment, $R^1$ is propyl. In another embodiment, $R^1$ is iso-propyl. In another embodiment, $R^1$ is butyl. In another embodiment, $R^1$ is tert-butyl.

In another embodiment, the present disclosure relates to a compound of formula (I) and the attendant definitions, wherein $R^1$ is $(C_1-C_6)$alkylsulfanyl. In another embodiment, $R^1$ is methylsulfanyl. In another embodiment, $R^1$ is $(C_1-C_6)$alkylsulfinyl. In another embodiment, $R^1$ is methylsulfinyl. In another embodiment, $R^1$ is $(C_1-C_6)$alkylsulfonyl. In another embodiment, $R^1$ is methylsulfonyl.

In one embodiment, the present disclosure relates to a compound of formula (I) and the attendant definitions, wherein $R^2$ is H, $(C_1-C_6)$alkylsulfanyl or $(C_1-C_6)$alkylsulfinyl. In another embodiment, $R^2$ is H, $(C_1-C_6)$alkylsulfanyl or $(C_1-C_6)$alkylsulfonyl. In another embodiment, $R^2$ is H, $(C_1-C_6)$alkylsulfanyl or $(C_1-C_6)$haloalkyl. In another embodiment, $R^2$ is H, $(C_1-C_6)$alkylsulfanyl or $(C_1-C_6)$perhaloalkyl. In another embodiment, $R^2$ is $(C_1-C_6)$alkylsulfanyl, $(C_1-C_6)$alkylsulfinyl or $(C_1-C_6)$alkylsulfonyl. In another embodiment, $R^2$ is $(C_1-C_6)$alkylsulfanyl, $(C_1-C_6)$alkylsulfinyl or $(C_1-C_6)$haloalkyl. In another embodiment, $R^2$ is $(C_1-C_6)$alkylsulfanyl, $(C_1-C_6)$alkylsulfinyl or $(C_1-C_6)$perhaloalkyl. In another embodiment, $R^2$ is $(C_1-C_6)$alkylsulfinyl, $(C_1-C_6)$alkylsulfanyl or $(C_1-C_6)$alkylsulfonyl. In another embodiment, $R^2$ is $(C_1-C_6)$alkylsulfinyl, $(C_1-C_6)$alkylsulfanyl or $(C_1-C_6)$haloalkyl. In another embodiment, $R^2$ is $(C_1-C_6)$alkylsulfinyl, $(C_1-C_6)$alkylsulfanyl or $(C_1-C_6)$perhaloalkyl. In another embodiment, $R^2$ is $(C_1-C_6)$alkylsulfonyl, $(C_1-C_6)$haloalkyl, or $(C_1-C_6)$perhaloalkyl.

In another embodiment, the present disclosure relates to a compound of formula (I) and the attendant definitions, wherein, $R^2$ is H. In another embodiment, $R^2$ is $(C_1-C_6)$alkylsulfanyl. In another embodiment, $R^2$ is methylsulfanyl. In another embodiment, $R^2$ is $(C_1-C_6)$alkylsulfinyl. In another embodiment, $R^2$ is methylsulfinyl. In another embodiment, $R^2$ is $(C_1-C_6)$alkylsulfonyl. In another embodiment, $R^2$ is methylsulfonyl. In another embodiment, $R^2$ is $(C_1-C_6)$haloalkyl. In another embodiment, $R^2$ is $(C_1-C_4)$haloalkyl. In another embodiment, $R^2$ is $(C_1-C_4)$fluoroalkyl. In another embodiment, $R^2$ is $(C_1-C_4)$chloroalkyl. In another embodiment, $R^2$ is $(C_1-C_4)$bromoalkyl. In another embodiment, $R^2$ is halomethyl. In another embodiment, $R^2$ is haloethyl. In another embodiment, $R^2$ is fluoromethyl. In another embodiment, $R^2$ is chloromethyl. In another embodiment, $R^2$ is bromomethyl. In another embodiment, $R^2$ is fluoroethyl. In another embodiment, $R^2$ is chloroethyl. In another embodiment, $R^2$ is bromoethyl. In another embodiment, $R^2$ is $(C_1-C_6)$perhaloalkyl. In one embodiment, $R^2$ is $(C_1-C_4)$perhaloalkyl. In another embodiment, $R^2$ is $(C_1-C_4)$perfluoroalkyl. In another embodiment, $R^2$ is $(C_1-C_4)$perchloroalkyl. In another embodiment, $R^2$ is $(C_1-C_4)$perbromoalkyl. In another embodiment, $R^2$ is perhalomethyl. In another embodiment, $R^2$ is perfluoromethyl. In another embodiment, $R^2$ is perchloromethyl. In another embodiment, $R^2$ is perbromomethyl.

In one embodiment, the present disclosure relates to a compound of formula (I) and the attendant definitions, wherein, $R^3$ is H, $(C_1-C_6)$alkylsulfanyl or $(C_1-C_6)$alkylsulfinyl. In another embodiment, $R^3$ is H, $(C_1-C_6)$alkylsulfanyl or $(C_1-C_6)$alkylsulfonyl. In another embodiment, $R^3$ is H, $(C_1-C_6)$alkylsulfanyl or $NR^6R^7$. In another embodiment, $R^3$ is $(C_1-C_6)$alkylsulfanyl, $(C_1-C_6)$alkylsulfinyl or $(C_1-C_6)$alkylsulfonyl. In another embodiment, $R^3$ is $(C_1-C_6)$alkylsulfanyl, $(C_1-C_6)$alkylsulfinyl or $NR^6R^7$. In another embodiment, $R^3$ is $(C_1-C_6)$alkylsulfinyl, $(C_1-C_6)$alkylsulfonyl or $NR^6R^7$. In various embodiments in which $R^3$ is $NR^6R^7$, said $NR^6R^7$ is $NH_2$ in one embodiment, $NH(C_1-C_6)$alkyl in another embodiment, and N-di$(C_1-C_6)$alkyl in an additional embodiment, wherein each alkyl is unsubstituted in one embodiment and substituted with (5- or 6-membered)heteroaryl in another embodiment. In another embodiment, $R^3$ is H, methylsulfanyl, methylsulfinyl, methylsulfonyl or furanylmethylamino. In another embodiment, $R^3$ is H. In another embodiment, $R^3$ is methylsulfanyl. In another embodiment, $R^3$ is methylsulfinyl. In another embodiment, $R^3$ is methylsulfonyl. In another embodiment, $R^3$ is furanylmethylamino.

In one embodiment, the present disclosure relates to a compound of formula (I) and the attendant definitions, wherein $R^4$ is H or COOH. In another embodiment, $R^4$ is H or $CONR^8OR^9$. In one embodiment, $R^4$ is COOH or $CONR^8OR^9$. In various embodiments in which $R^4$ is $CONR^8OR^9$, said $CONR^8OR^9$ is CONHOH in one embodiment, $CONHO(C_1-C_6)$alkyl in another embodiment, and $CON(C_1-C_6)$alkyl$O(C_1-C_6)$alkyl in an additional embodiment, wherein each alkyl is unsubstituted in one embodiment and substituted with phenyl in another embodiment. In one embodiment, $R^4$ is H, COOH or CONHObenzyl. In another embodiment, $R^4$ is H. In another embodiment, $R^4$ is COOH. In another embodiment, $R^4$ is CONHObenzyl.

In one embodiment, the present disclosure relates to a compound of formula (I) and the attendant definitions, wherein R is $(C_1-C_6)$alkyl. In another embodiment, R is $(C_1-C_4)$alkyl. In another embodiment, R is methyl, ethyl, propyl, or butyl. In another embodiment, R is methyl, ethyl, or propyl. In another embodiment, R is methyl, ethyl, or butyl. In another embodiment, R is methyl, propyl, or butyl. In another embodiment, R is ethyl, propyl, or butyl. In another embodiment, R is methyl or ethyl. In another embodiment, R is methyl or propyl. In another embodiment, R is methyl or butyl. In another embodiment, R is ethyl or propyl. In another embodiment, R is ethyl or butyl. In another embodiment, R is propyl or butyl. In another embodiment, R is methyl. In another embodiment, R is ethyl. In another embodiment, R is propyl. In another embodiment, R is iso-propyl. In another embodiment, R is butyl. In another embodiment, R is tert-butyl.

In various embodiments in which R is $(C_1-C_6)$alkyl, said alkyl is unsubstituted in a first embodiment, substituted with phenyl is a second embodiment, substituted with (5- or 6-membered)heterocycloalkyl in a third embodiment, substituted with (5- or 6-membered)heterocycloalkenyl in a fourth embodiment, substituted with (5- or 6-membered) heteroaryl in a fifth embodiment or substituted with $O(C=O)(C_1-C_6)$alkyl in a sixth embodiment.

In one embodiment, R is $(C_1-C_4)$alkyl, said alkyl is unsubstituted in a first embodiment, substituted with phenyl is a second embodiment, substituted with (5- or 6-membered)heterocycloalkyl in a third embodiment, substituted with (5- or 6-membered)heterocycloalkenyl in a fourth embodiment, substituted with (5- or 6-membered)heteroaryl in a fifth embodiment or substituted with O(C=O)($C_1$-$C_6$) alkyl in a sixth embodiment. In another embodiment, R is ($C_1$-$C_2$)alkyl, said alkyl is unsubstituted in a first embodiment, substituted with phenyl is a second embodiment, substituted with (5- or 6-membered)heterocycloalkyl in a third embodiment, substituted with (5- or 6-membered)heterocycloalkenyl in a fourth embodiment, substituted with (5- or 6-membered)heteroaryl in a fifth embodiment or substituted with O(C=O)($C_1$-$C_6$)alkyl in a sixth embodiment.

In one embodiment, R is ($C_1$-$C_3$)alkyl substituted with phenyl. In another embodiment, R is ($C_1$)alkyl substituted with phenyl. In another embodiment, R is ($C_2$)alkyl substituted with phenyl. In another embodiment, R is ($C_3$)alkyl substituted with phenyl. In various embodiments, said phenyl is (a) fused to a (5- or 6-membered)heterocycloalkyl, (b) fused to a (5- or 6-membered)heteroaryl, (c) unsubstituted or (d) substituted with 1, 2 or 3 substituent(s) selected from among those disclosed above for phenyl in connection with formula (I). In another embodiment, said phenyl is fused to 5-membered heterocycloalkyl. In another embodiment, said phenyl is fused to 6-membered heterocycloalkyl. In another embodiment, said phenyl is fused to 5-membered heteroaryl. In another embodiment, said phenyl is fused to 6-membered heteroaryl. In another embodiment, said fused phenyl is benzodioxylyl. In another embodiment, said fused phenyl is benzoxadiazolyl. In another embodiment, said phenyl is substituted with 1, 2 or 3 substituent(s) independently selected from halo, OH, ($C_1$-$C_6$)alkyl, ($C_1$-$C_6$)perhaloalkyl, ($C_1$-$C_6$)alkoxy, ($C_1$-$C_6$)perhaloalkoxy, ($C_1$-$C_6$)alkylsulfonyl, $SO_2$-(5- or 6-membered)heterocycloalkyl, (5- or 6-membered)heteroaryl, OC(=O)($C_1$-$C_6$)alkyl, NHC(=O)($C_1$-$C_6$)alkyl, C(=O)N-di($C_1$-$C_6$)alkoxy and N,N-di($C_1$-$C_6$)alkoxyaminosulfonyl. In another embodiment, said phenyl is substituted with 1, 2 or 3 substituent(s) independently selected from OC(=O)$CH_3$, OH, OH, $CF_3$, F, Cl, Br, $CH_3$, propan-2-yl, tert-butyl, $OCH_3$, $SO_2$-morpholinyl, $OCF_3$, $SO_2CH_3$, CON($CH_2CH_2OCH_3$)$_2$, 1H-pyrazol-1-yl, NHCOCH$_3$ and $SO_2N(CH_2CH_2OCH_3)_2$.

In one embodiment, R is ($C_1$)alkyl substituted with (5- or 6-membered)heterocycloalkyl. In another embodiment, R is ($C_1$)alkyl substituted with (5-membered)heterocycloalkyl. In another embodiment, R is ($C_1$)alkyl substituted with (6-membered)heterocycloalkyl. In one embodiment, R is ($C_1$)alkyl substituted with dioxolanyl. In various embodiments, said heterocycloalkyl is unsubstituted or substituted with 1, 2 or 3 substituent(s) selected from among those disclosed above for heterocycloalkyl in connection with formula (I). In another embodiment, the substituent(s) are selected from oxo or ($C_1$-$C_6$)alkyl. In another embodiment, the substituent(s) are selected from oxo and methyl.

In one embodiment, R is ($C_1$)alkyl substituted with (5- or 6-membered)heterocycloalkenyl. In another embodiment, R is ($C_1$)alkyl substituted with (5-membered)heterocycloalkenyl. In another embodiment, R is ($C_1$)alkyl substituted with (6-membered)heterocycloalkenyl. In one embodiment, R is ($C_1$)alkyl substituted with dioxolyl. In various embodiments, said heterocycloalkenyl is unsubstituted or substituted with 1, 2 or 3 substituent(s) selected from among those disclosed above for heterocycloalkenyl in connection with formula (I). In another embodiment, the substituent(s) are selected from oxo or ($C_1$-$C_6$)alkyl. In another embodiment, the substituent(s) are selected from oxo and methyl.

In one embodiment, R is ($C_1$)alkyl substituted with (5- or 6-membered) heteroaryl. In another embodiment, R is ($C_1$) alkyl substituted with (5-membered) heteroaryl. In another embodiment, R is ($C_1$)alkyl substituted with (6-membered) heteroaryl. In one embodiment, R is ($C_1$)alkyl substituted with pyridinyl, furan or oxazolyl. In various embodiments, said heteroaryl is unsubstituted or substituted with 1, 2 or 3 substituent(s) selected from among those disclosed above for heteroaryl in connection with formula (I). In another embodiment, the substituent(s) are selected from ($C_1$-$C_6$)alkyl, ($C_1$-$C_6$)haloalkyl and ($C_1$-$C_6$)perhaloalkyl. In another embodiment, the substituent(s) are selected from perfluoromethyl and methyl.

In one embodiment, R is ($C_1$-$C_3$)alkyl substituted with O(C=O)($C_1$-$C_6$)alkyl. In another embodiment, R is ($C_1$) alkyl substituted with O(C=O)($C_1$-$C_6$)alkyl. In another embodiment, R is ($C_2$)alkyl substituted with O(C=O)($C_1$-$C_6$)alkyl. In another embodiment, R is ($C_3$)alkyl substituted with O(C=O)($C_1$-$C_6$)alkyl. In another embodiment, R is ($C_1$-$C_3$)alkyl substituted with O(C=O)($C_1$-$C_4$)alkyl. In another embodiment, R is ($C_1$)alkyl substituted with O(C=O)($C_1$-$C_4$)alkyl. In another embodiment, R is ($C_2$)alkyl substituted with O(C=O)($C_1$-$C_4$)alkyl. In another embodiment, R is ($C_3$)alkyl substituted with O(C=O)($C_1$-$C_4$)alkyl. In another embodiment, R is ($C_1$-$C_3$)alkyl substituted with O(C=O)methyl. In another embodiment, R is ($C_1$-$C_3$)alkyl substituted with O(C=O)ethyl. In another embodiment, R is ($C_1$-$C_3$)alkyl substituted with O(C=O)propyl. In another embodiment, R is ($C_1$-$C_3$)alkyl substituted with O(C=O)butyl. In another embodiment, R is ($C_1$)alkyl substituted with O(C=O)methyl. In another embodiment, R is ($C_1$)alkyl substituted with O(C=O)ethyl. In another embodiment, R is ($C_1$)alkyl substituted with O(C=O)propyl. In another embodiment, R is ($C_1$)alkyl substituted with O(C=O)butyl. In another embodiment, R is ($C_2$)alkyl substituted with O(C=O)methyl. In another embodiment, R is ($C_2$)alkyl substituted with O(C=O)ethyl. In another embodiment, R is ($C_2$)alkyl substituted with O(C=O)propyl. In another embodiment, R is ($C_2$)alkyl substituted with O(C=O)butyl. In another embodiment, R is ($C_3$)alkyl substituted with O(C=O)methyl. In another embodiment, R is ($C_3$)alkyl substituted with O(C=O)ethyl. In another embodiment, R is ($C_3$)alkyl substituted with O(C=O)propyl. In another embodiment, R is ($C_3$)alkyl substituted with O(C=O)butyl.

In another embodiment, the present disclosure relates to a compound of formula (I) and the attendant definitions, wherein R is (5- or 6-membered)heterocycloalkyl. In another embodiment, R is a (5-membered)heterocycloalkyl. In another embodiment, R is a (6-membered)heterocycloalkyl. In another embodiment, R is oxanyl.

In another embodiment, the present disclosure relates to a compound of formula (I) and the attendant definitions, wherein R is ($C_5$-$C_7$)cycloalkyl. In another embodiment, R is cyclopentyl or cyclohexyl. In another embodiment, R is cyclopentyl or cycloheptyl. In another embodiment, R is cyclohexyl or cycloheptyl. In another embodiment, R is cyclopentyl. In another embodiment, R is cyclohexyl. In another embodiment, R is cycloheptyl.

In another embodiment, the present disclosure relates to a compound of formula (I) and the attendant definitions, wherein R is C(=O)(5- or 6-membered)heteroaryl. In another embodiment, R is C(=O)(5-membered)heteroaryl. In another embodiment, R is C(=O)(6-membered) heteroaryl. In another embodiment, R is pyridinyl, pyridazinyl, pyrimidinyl or pyrazinyl. In another embodiment, R is pyrazinyl.

Another aspect of the disclosure provides a compound of formula (II):

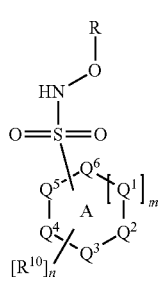

(II)

or a pharmaceutically acceptable salt thereof, wherein:
ring A is a heterocyclic or heteroaromatic ring containing $Q^1$, $Q^2$, $Q^3$, $Q^4$, $Q^5$ and $Q^6$ that are independently selected from C, CH, $CH_2$, N, NH, and S, provided that at least one of $Q^1$, $Q^2$, $Q^3$, $Q^4$, $Q^5$ and $Q^6$ is N, NH or S, wherein said N is optionally oxidized;
$R^{10}$ is $(C_1-C_6)$alkyl, halo, C(=O)-(5- or 6-membered)heterocycloalkyl, C(=O)NH—$(C_1-C_6)$alkyl or C(=O)N-di$(C_1-C_6)$alkyl;
R is $(C_1-C_6)$alkyl, wherein said alkyl is unsubstituted or substituted with phenyl;
n is an integer from 0 to 1; and
m is an integer from 0 to 1;
provided that:
(1) when ring A is 3-pyridinyl, pyrrolidinyl, azepinyl, piperidinyl, morpholinyl or thienyl, then n is not 0;
(2) when ring A is piperazinyl and n is 0, then R is not alkyl;
(3) when ring A is piperidinyl, then $R^{10}$ is not methyl;
(4) when ring A is 2-pyridinyl or 3-pyridinyl, then $R^{10}$ is not halo; and
(5) when ring A is thienyl, then $R^{10}$ is not methyl, ethyl or halo.

In one embodiment, the present disclosure relates to a compound of formula (II) and the attendant definitions, wherein ring A is a heterocyclic ring containing $Q^1$, $Q^2$, $Q^3$, $Q^4$, $Q^5$ and $Q^6$ that are independently selected from C, CH, $CH_2$, N, NH, and S, provided that at least one of $Q^1$, $Q^2$, $Q^3$, $Q^4$, $Q^5$ and $Q^6$ is N, NH or S, wherein said N is optionally oxidized. In another embodiment, ring A is a heteroaromatic ring containing $Q^1$, $Q^2$, $Q^3$, $Q^4$, $Q^5$ and $Q^6$ that are independently selected from C, CH, $CH_2$, N, NH, and S, provided that at least one of $Q^1$, $Q^2$, $Q^3$, $Q^4$, $Q^5$ and $Q^6$ is N, NH or S, wherein said N is optionally oxidized. In another embodiment, ring A is piperazinyl, thienyl, pyridinyl, pyridinium, piperidinyl, morpholinyl, furanyl, pyrrolyl, isoxazolyl, pyrazolyl, imidazolyl, thiazolyl, triazolyl, thiadiazolly, pyrimidinyl or pyrazinyl. In another embodiment, ring A is piperazinyl, thienyl, pyridinyl, or pyridinium. In another embodiment, ring A is piperazinyl. In another embodiment, ring A is thienyl. In another embodiment, ring A is pyridinyl. In another embodiment, ring A is pyridinium.

In one embodiment, the present disclosure relates to a compound of formula (II) and the attendant definitions, wherein $R^{10}$ is $(C_1-C_6)$alkyl, halo, or C(=O)-(5- or 6-membered)heterocycloalkyl. In another embodiment, $R^{10}$ is $(C_1-C_6)$alkyl, halo, or C(=O)NH—$(C_1-C_6)$alkyl. In another embodiment, $R^{10}$ is $(C_1-C_6)$alkyl, halo, or C(=O)N-di$(C_1-C_6)$alkyl. In another embodiment, $R^{10}$ is halo, C(=O)-(5- or 6-membered)heterocycloalkyl or C(=O)NH—$(C_1-C_6)$ alkyl. In another embodiment, $R^{10}$ is halo, C(=O)-(5- or 6-membered)heterocycloalkyl or C(=O)N-di$(C_1-C_6)$alkyl. In another embodiment, $R^{10}$ is C(=O)-(5- or 6-membered) heterocycloalkyl, C(=O)NH—$(C_1-C_6)$alkyl or C(=O)N-di $(C_1-C_6)$alkyl. In another embodiment, $R^{10}$ is methyl, C(=O)-morpholinyl, chloro or C(=O)NH-propan-2-yl.

In another embodiment, the present disclosure relates to a compound of formula (II) and the attendant definitions, wherein $R^{10}$ is $(C_1-C_4)$alkyl. In another embodiment, $R^{10}$ is methyl, ethyl, propyl, or butyl. In another embodiment, $R^{10}$ is methyl, ethyl, or propyl. In another embodiment, $R^{10}$ is methyl, ethyl, or butyl. In another embodiment, $R^{10}$ is methyl, propyl, or butyl. In another embodiment, $R^{10}$ is ethyl, propyl, or butyl. In another embodiment, $R^{10}$ is methyl or ethyl. In another embodiment, $R^{10}$ is methyl or propyl. In another embodiment, $R^{10}$ is methyl or butyl. In another embodiment, $R^{10}$ is ethyl or propyl. In another embodiment, $R^{10}$ is ethyl or butyl. In another embodiment, $R^{10}$ is propyl or butyl. In another embodiment, $R^{10}$ is methyl. In another embodiment, $R^{10}$ is ethyl. In another embodiment, $R^{10}$ is propyl. In another embodiment, $R^{10}$ is iso-propyl. In another embodiment, $R^{10}$ is butyl. In another embodiment, $R^{10}$ is tert-butyl.

In another embodiment, the present disclosure relates to a compound of formula (II) and the attendant definitions, wherein $R^{10}$ is halo. In another embodiment, $R^{10}$ is fluoro, chloro or bromo. In another embodiment, $R^{10}$ is fluoro or chloro. In another embodiment, $R^{10}$ is fluoro or bromo. In another embodiment, $R^{10}$ is chloro or bromo. In another embodiment, $R^{10}$ is fluoro. In another embodiment, $R^{10}$ is chloro. In another embodiment, $R^{10}$ is bromo.

In another embodiment, the present disclosure relates to a compound of formula (II) and the attendant definitions, wherein $R^{10}$ is C(=O)-(5- or 6-membered)heterocycloalkyl. In another embodiment, $R^{10}$ is C(=O)-(5-membered)heterocycloalkyl. In another embodiment, $R^{10}$ is C(=O)-(6-membered)heterocycloalkyl. In another embodiment, $R^{10}$ is C(=O)-morpholinyl.

In another embodiment, the present disclosure relates to a compound of formula (II) and the attendant definitions, wherein $R^{10}$ is C(=O)N-di$(C_1-C_6)$alkyl. In another embodiment, $R^{10}$ is C(=O)N-di$(C_1-C_4)$alkyl. In another embodiment, $R^{10}$ is C(=O)N-di$(C_1-C_3)$alkyl. In another embodiment, $R^{10}$ is C(=O)N-dialkyl, in which each alkyl is independently selected from methyl, ethyl, propyl, or butyl. In another embodiment, $R^{10}$ is C(=O)N-dialkyl, in which each alkyl is independently selected from methyl, ethyl, or propyl. In another embodiment, $R^{10}$ is C(=O)N-dialkyl, in which each alkyl is independently selected from methyl, ethyl, or butyl. In another embodiment, $R^{10}$ is C(=O)N-dialkyl, in which each alkyl is independently selected from methyl, propyl, or butyl. In another embodiment, $R^{10}$ is C(=O)N-dialkyl, in which each alkyl is independently selected from ethyl, propyl, or butyl. In another embodiment, $R^{10}$ is C(=O)N-dialkyl, in which each alkyl is independently selected from methyl or ethyl. In another embodiment, $R^{10}$ is C(=O)N-dialkyl, in which each alkyl is independently selected from methyl or propyl. In another embodiment, $R^{10}$ is C(=O)N-dialkyl, in which each alkyl is independently selected from methyl or butyl. In another embodiment, $R^{10}$ is C(=O)N-dialkyl, in which each alkyl is independently selected from ethyl or propyl. In another embodiment, $R^{10}$ is C(=O)N-dialkyl, in which each alkyl is independently selected from ethyl or butyl. In another embodiment, $R^{10}$ is C(=O)N-dialkyl, in which each alkyl is independently selected from propyl or butyl. In another embodiment, $R^{10}$ is C(=O)N-dialkyl, in which at least one alkyl is methyl. In another embodiment, $R^{10}$ is C(=O)N-dialkyl, in which both alkyl are methyl. In another embodiment, $R^{10}$ is C(=O)N-dialkyl, in which at least one alkyl is ethyl. In another embodiment, $R^{10}$ is C(=O)N-dialkyl, in which both alkyl are ethyl. In another embodiment, $R^{10}$ is C(=O)N-dialkyl, in which at least one alkyl is propyl. In another embodiment, $R^{10}$ is C(=O)N-dialkyl, in which both alkyl are propyl. In another embodiment, $R^{10}$ is C(=O)N-dialkyl, in which at least one alkyl is iso-propyl. In another embodiment, $R^{10}$ is C(=O)N-dialkyl, in which both alkyl are iso-propyl. In another embodiment, $R^{10}$ is C(=O)N-dialkyl, in which at least one alkyl is butyl. In another embodiment, $R^{10}$ is C(=O)N-dialkyl, in which both alkyl are butyl. In another embodiment, $R^{10}$ is C(=O)N-dialkyl, in which at least one alkyl is tert-butyl. In another embodiment, $R^{10}$ is C(=O)N-dialkyl, in which both alkyl are tert-butyl.

In another embodiment, the present disclosure relates to a compound of formula (II) and the attendant definitions, wherein $R^{10}$ is C(=O)NH($C_1$-$C_6$)alkyl. In another embodiment, $R^{10}$ is C(=O)NH($C_1$-$C_4$)alkyl. In another embodiment, $R^{10}$ is C(=O)NH($C_1$-$C_3$)alkyl. In another embodiment, $R^{10}$ is C(=O)NH($C_1$-$C_4$)alkyl, in which said alkyl is methyl, ethyl, propyl, or butyl. In another embodiment, $R^{10}$ is C(=O)NH($C_1$-$C_4$)alkyl, in which said alkyl is methyl, ethyl, or propyl. In another embodiment, $R^{10}$ is C(=O)NH($C_1$-$C_4$)alkyl, in which said alkyl is methyl, ethyl, or butyl. In another embodiment, $R^{10}$ is C(=O)NH($C_1$-$C_4$)alkyl, in which said alkyl is methyl, propyl, or butyl. In another embodiment, $R^{10}$ is C(=O)NH($C_1$-$C_4$)alkyl, in which said alkyl is ethyl, propyl, or butyl. In another embodiment, $R^{10}$ is C(=O)NH($C_1$-$C_4$)alkyl, in which said alkyl is methyl or ethyl. In another embodiment, $R^{10}$ is C(=O)NH($C_1$-$C_4$)alkyl, in which said alkyl is methyl or propyl. In another embodiment, $R^{10}$ is C(=O)NH($C_1$-$C_4$)alkyl, in which said alkyl is methyl or butyl. In another embodiment, $R^{10}$ is C(=O)NH($C_1$-$C_4$)alkyl, in which said alkyl is ethyl or propyl. In another embodiment, $R^{10}$ is C(=O)NH($C_1$-$C_4$)alkyl, in which said alkyl is ethyl or butyl. In another embodiment, $R^{10}$ is C(=O)NH($C_1$-$C_4$)alkyl, in which said alkyl is propyl or butyl. In another embodiment, $R^{10}$ is C(=O)NH($C_1$-$C_4$)alkyl, in which said alkyl is methyl. In another embodiment, $R^{10}$ is C(=O)NH($C_1$-$C_4$)alkyl, in which said alkyl is ethyl. In another embodiment, $R^{10}$ is C(=O)NH($C_1$-$C_4$)alkyl, in which said alkyl is propyl. In another embodiment, $R^{10}$ is C(=O)NH($C_1$-$C_4$)alkyl, in which said alkyl is iso-propyl. In another embodiment, $R^{10}$ is C(=O)NH($C_1$-$C_4$)alkyl in which said alkyl is butyl. In another embodiment, $R^{10}$ is C(=O)NH($C_1$-$C_4$)alkyl, in which said alkyl is tert-butyl.

In one embodiment, the present disclosure relates to a compound of formula (II) and the attendant definitions, wherein R is ($C_1$-$C_6$)alkyl. In another embodiment, R is ($C_1$-$C_4$)alkyl. In another embodiment, R is methyl, ethyl, propyl, or butyl. In another embodiment, R is methyl, ethyl, or propyl. In another embodiment, R is methyl, ethyl, or butyl. In another embodiment, R is methyl, propyl, or butyl. In another embodiment, R is ethyl, propyl, or butyl. In another embodiment, R is methyl or ethyl. In another embodiment, R is methyl or propyl. In another embodiment, R is methyl or butyl. In another embodiment, R is ethyl or propyl. In another embodiment, R is ethyl or butyl. In another embodiment, R is propyl or butyl. In another embodiment, R is methyl. In another embodiment, R is ethyl. In another embodiment, R is propyl. In another embodiment, R is iso-propyl. In another embodiment, R is butyl. In another embodiment, R is tert-butyl.

In various embodiments in which R is ($C_1$-$C_6$)alkyl, said alkyl is unsubstituted in one embodiment and substituted with phenyl is another embodiment. In one embodiment, R is ($C_1$-$C_4$)alkyl, said alkyl being unsubstituted in one embodiment and substituted with phenyl is another embodiment. In another embodiment, R is ($C_1$-$C_3$)alkyl, said alkyl being unsubstituted in one embodiment and substituted with phenyl is another embodiment. In another embodiment, R is ($C_1$-$C_2$)alkyl, said alkyl being unsubstituted in one embodiment and substituted with phenyl is another embodiment.

In one embodiment, R is ($C_1$-$C_3$)alkyl substituted with phenyl. In another embodiment, R is ($C_1$)alkyl substituted with phenyl. In another embodiment, R is ($C_2$)alkyl substituted with phenyl. In another embodiment, R is ($C_3$)alkyl substituted with phenyl.

Another aspect of the disclosure provides a compound of formula (III):

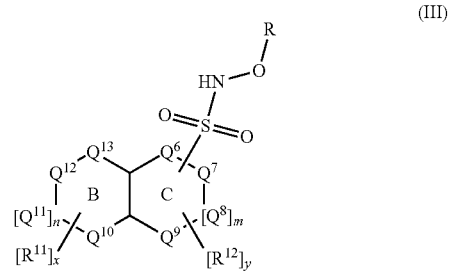

or a pharmaceutically acceptable salt thereof, wherein:
Ring B is a heteroaromatic or aromatic ring containing $Q^{10}$, $Q^{11}$, $Q^{12}$ and $Q^{13}$, wherein $Q^{10}$, $Q^{11}$, $Q^{12}$ and $Q^{13}$ are independently selected from C, CH, O, N, NH and S;
Ring C is a heteroaromatic ring containing $Q^6$, $Q^7$, $Q^8$ and $Q^9$, wherein $Q^6$, $Q^7$, $Q^8$ and $Q^9$ are independently selected from C, CH, O, N, NH and S, provided that at least one of $Q^6$, $Q^7$, $Q^8$ and $Q^9$ is O, N, NH or S;
$R^{11}$ and $R^{12}$ are independently selected from ($C_1$-$C_6$)alkoxy and halo;
m and n are independently selected from 0 to 1;
x is an integer selected from 0 to 4;
y is an integer selected from 0 to 3; and
R is ($C_1$-$C_6$)alkyl or ($C_5$-$C_7$)cycloalkyl, wherein said alkyl is unsubstituted or substituted with phenyl, (5- or 6-membered)heterocycloalkyl, (5- or 6-membered)heterocycloalkenyl or (5- or 6-membered)heteroaryl;
wherein said phenyl is unsubstituted or substituted with 1, 2, 3, 4 or 5 substituents independently selected from halo, ($C_1$-$C_6$)alkyl and ($C_1$-$C_6$)alkoxy;
wherein said heterocycloalkyl or heterocycloalkenyl is unsubstituted or substituted with 1, 2 or 3 substituents independently selected from oxo and ($C_1$-$C_6$)alkyl; and
wherein said heteroaryl is unsubstituted or substituted with 1, 2 or 3 substituents selected from ($C_1$-$C_6$)alkyl.

In one embodiment, the present disclosure relates to a compound of formula (III) and the attendant definitions, wherein ring B is a heteroaromatic containing $Q^{10}$, $Q^{11}$, $Q^{12}$ and $Q^{13}$, wherein $Q^{10}$, $Q^{11}$, $Q^{12}$ and $Q^{13}$ are independently selected from C, CH, O, N, NH and S. In another embodiment, ring B is an aromatic ring. In another embodiment, ring B is an aromatic ring and ring C is a heteroaromatic ring containing $Q^6$, $Q^7$, $Q^8$ and $Q^9$, provided that at least one of $Q^6$, $Q^7$, $Q^8$ and $Q^9$ is O. In another embodiment, ring B is an aromatic ring and ring C is a heteroaromatic ring containing $Q^6$, $Q^7$, $Q^8$ and $Q^9$, provided that at least one of $Q^6$, $Q^7$, $Q^8$ and $Q^9$ is N. In another embodiment, ring B is an aromatic ring and ring C is a heteroaromatic ring containing $Q^6$, $Q^7$, $Q^8$ and $Q^9$, provided that at least one of $Q^6$, $Q^7$, $Q^8$ and $Q^9$ is NH. In another embodiment, ring B is an aromatic ring and ring C is a heteroaromatic ring containing $Q^6$, $Q^7$, $Q^8$ and $Q^9$, provided that at least one of $Q^6$, $Q^7$, $Q^8$ and $Q^9$ is S. In another embodiment, rings B and C form benzofuranyl, benzothiophenyl, benzoimidazolyl, benzothiazolyl, benzoxazolyl or quinolinyl. In another embodiment, rings B and C form benzofuranyl.

In one embodiment, the present disclosure relates to a compound of formula (III) and the attendant definitions, wherein $R^{11}$ is $(C_1-C_6)$alkoxy. In another embodiment, $R^{11}$ is $(C_1-C_4)$alkoxy. In another embodiment, $R^{11}$ is methoxy, ethoxy, propoxy, or butoxy. In another embodiment, $R^{11}$ is methoxy, ethoxy, or propoxy. In another embodiment, $R^{11}$ is methoxy, ethoxy, or butoxy. In another embodiment, $R^{11}$ is methoxy, propoxy, or butoxy. In another embodiment, $R^{11}$ is ethoxy, propoxy, or butoxy. In another embodiment, $R^{11}$ is methoxy or ethoxy. In another embodiment, $R^{11}$ is methoxy or propoxy. In another embodiment, $R^{11}$ is methoxy or butoxy. In another embodiment, $R^{11}$ is ethoxy or propoxy. In another embodiment, $R^{11}$ is ethoxy or butoxy. In another embodiment, $R^{11}$ is propoxy or butoxy. In another embodiment, $R^{11}$ is methoxy. In another embodiment, $R^{11}$ is ethoxy. In another embodiment, $R^{11}$ is propoxy. In another embodiment, $R^{11}$ is iso-propoxy. In another embodiment, $R^{11}$ is butoxy. In another embodiment, $R^{11}$ is tert-butoxy.

In another embodiment, the present disclosure relates to a compound of formula (III) and the attendant definitions, wherein $R^{11}$ is halo. In another embodiment, $R^{11}$ is fluoro, chloro or bromo. In another embodiment, $R^{11}$ is fluoro or chloro. In another embodiment, $R^{11}$ is fluoro or bromo. In another embodiment, $R^{11}$ is chloro or bromo. In another embodiment, $R^{11}$ is fluoro. In another embodiment, $R^{11}$ is chloro. In another embodiment, $R^{11}$ is bromo.

In one embodiment, the present disclosure relates to a compound of formula (III) and the attendant definitions, wherein $R^{12}$ is $(C_1-C_6)$alkoxy. In another embodiment, $R^{12}$ is $(C_1-C_4)$alkoxy. In another embodiment, $R^{12}$ is methoxy, ethoxy, propoxy, or butoxy. In another embodiment, $R^{12}$ is methoxy, ethoxy, or propoxy. In another embodiment, $R^{12}$ is methoxy, ethoxy, or butoxy. In another embodiment, $R^{12}$ is methoxy, propoxy, or butoxy. In another embodiment, $R^{12}$ is ethoxy, propoxy, or butoxy. In another embodiment, $R^{12}$ is methoxy or ethoxy. In another embodiment, $R^{12}$ is methoxy or propoxy. In another embodiment, $R^{12}$ is methoxy or butoxy. In another embodiment, $R^{12}$ is ethoxy or propoxy. In another embodiment, $R^{12}$ is ethoxy or butoxy. In another embodiment, $R^2$ is propoxy or butoxy. In another embodiment, $R^{12}$ is methoxy. In another embodiment, $R^{12}$ is ethoxy. In another embodiment, $R^{12}$ is propoxy. In another embodiment, $R^{12}$ is iso-propoxy. In another embodiment, $R^{12}$ is butoxy. In another embodiment, $R^{12}$ is tert-butoxy.

In another embodiment, the present disclosure relates to a compound of formula (III) and the attendant definitions, wherein $R^{12}$ is halo. In another embodiment, $R^{12}$ is fluoro, chloro or bromo. In another embodiment, $R^{12}$ is fluoro or chloro. In another embodiment, $R^{12}$ is fluoro or bromo. In another embodiment, $R^{12}$ is chloro or bromo. In another embodiment, $R^{12}$ is fluoro. In another embodiment, $R^{12}$ is chloro. In another embodiment, $R^{12}$ is bromo.

In one embodiment, the present disclosure relates to a compound of formula (III) and the attendant definitions, wherein R is $(C_1-C_6)$alkyl. In another embodiment, R is $(C_1-C_4)$alkyl. In another embodiment, R is methyl, ethyl, propyl, or butyl. In another embodiment, R is methyl, ethyl, or propyl. In another embodiment, R is methyl, ethyl, or butyl. In another embodiment, R is methyl, propyl, or butyl. In another embodiment, R is ethyl, propyl, or butyl. In another embodiment, R is methyl or ethyl. In another embodiment, R is methyl or propyl. In another embodiment, R is methyl or butyl. In another embodiment, R is ethyl or propyl. In another embodiment, R is ethyl or butyl. In another embodiment, R is propyl or butyl. In another embodiment, R is methyl. In another embodiment, R is ethyl. In another embodiment, R is propyl. In another embodiment, R is iso-propyl. In another embodiment, R is butyl. In another embodiment, R is tert-butyl.

In various embodiments in which R is $(C_1-C_6)$alkyl, said alkyl is unsubstituted in a first embodiment, substituted with phenyl is a second embodiment, substituted with (5- or 6-membered)heterocycloalkyl in a third embodiment, substituted with (5- or 6-membered)heterocycloalkenyl in a fourth embodiment, and substituted with (5- or 6-membered)heteroaryl in a fifth embodiment.

In one embodiment, R is $(C_1-C_4)$alkyl, said alkyl is unsubstituted in a first embodiment, substituted with phenyl is a second embodiment, substituted with (5- or 6-membered)heterocycloalkyl in a third embodiment, substituted with (5- or 6-membered)heterocycloalkenyl in a fourth embodiment, and substituted with (5- or 6-membered)heteroaryl in a fifth embodiment. In another embodiment, R is $(C_1-C_2)$alkyl, said alkyl is unsubstituted in a first embodiment, substituted with phenyl is a second embodiment, substituted with (5- or 6-membered)heterocycloalkyl in a third embodiment, substituted with (5- or 6-membered) heterocycloalkenyl in a fourth embodiment, and substituted with (5- or 6-membered)heteroaryl in a fifth embodiment.

In one embodiment, R is $(C_1-C_3)$alkyl substituted with phenyl. In another embodiment, R is $(C_1)$alkyl substituted with phenyl. In another embodiment, R is $(C_2)$alkyl substituted with phenyl. In another embodiment, R is $(C_3)$alkyl substituted with phenyl. In various embodiments of this paragraph, said phenyl is unsubstituted or substituted with 1, 2 or 3 substituent(s) independently selected from among those disclosed above for phenyl in connection with formula (III). In another embodiment, the substituent(s) are independently selected from F, Cl, methyl, propan-2-yl, and methoxy.

In one embodiment, R is $(C_1)$alkyl substituted with (5- or 6-membered)heterocycloalkyl. In another embodiment, R is $(C_1)$alkyl substituted with (5-membered)heterocycloalkyl. In another embodiment, R is $(C_1)$alkyl substituted with (6-membered)heterocycloalkyl. In one embodiment, R is $(C_1)$alkyl substituted with dioxolanyl. In various embodiments of this paragraph, said heterocycloalkyl is unsubstituted or substituted with 1, 2 or 3 substituent(s) independently selected from among those disclosed above for heterocycloalkyl in connection with formula (III). In another embodiment, the substituent(s) are independently selected from oxo and methyl.

In one embodiment, R is (C$_1$)alkyl substituted with (5- or 6-membered)heterocycloalkenyl. In another embodiment, R is (C$_1$)alkyl substituted with (5-membered)heterocycloalkenyl. In another embodiment, R is (C$_1$)alkyl substituted with (6-membered)heterocycloalkenyl. In one embodiment, R is (C$_1$)alkyl substituted with dioxolyl. In various embodiments of this paragraph, said heterocycloalkenyl is unsubstituted or substituted with 1, 2 or 3 substituent(s) independently selected from among those disclosed above for heterocycloalkenyl in connection with formula (III). In another embodiment, the substituent(s) are independently selected from oxo and methyl.

In one embodiment, R is (C$_1$)alkyl substituted with (5- or 6-membered) heteroaryl. In another embodiment, R is (C$_1$) alkyl substituted with (5-membered) heteroaryl. In another embodiment, R is (C$_1$)alkyl substituted with (6-membered) heteroaryl. In one embodiment, R is (C$_1$)alkyl substituted with pyridinyl, furan or oxazolyl. In various embodiments of this paragraph, said heteroaryl is unsubstituted or substituted with 1, 2 or 3 substituent(s) independently selected from among those disclosed above for heteroaryl in connection with formula (III). In another embodiment, the substituent(s) are independently selected from (C$_1$-C$_6$)alkyl, (C$_1$-C$_6$)haloalkyl and (C$_1$-C$_6$)perhaloalkyl. In another embodiment, the substituent(s) are independently selected from perfluoromethyl and methyl.

In another embodiment, the present disclosure relates to a compound of formula (III) and the attendant definitions, wherein R is (C$_5$-C$_7$)cycloalkyl. In another embodiment, R is cyclopentyl or cyclohexyl. In another embodiment, R is cyclopentyl or cycloheptyl. In another embodiment, R is cyclohexyl or cycloheptyl. In another embodiment, R is cyclopentyl. In another embodiment, R is cyclohexyl. In another embodiment, R is cycloheptyl.

Table 1 provides representative compounds of the disclosure.

TABLE 1

| No | Structure | Name |
|---|---|---|
| 1 | 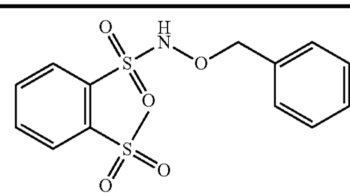 | N-(Benzyloxy)-2-methanesulfonylbenzene-1-sulfonamide |
| 2 | 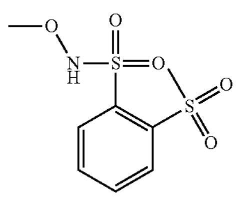 [SMILES: CONS(=O)(=O)c1ccccc1S(C)(=O)=O] | 2-Methanesulfonyl-N-methoxybenzene-1-sulfonamide |
| 3 | 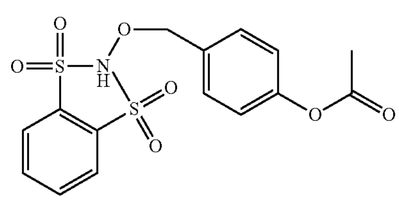 [SMILES: CC(=O)Oc1ccc(CONS(=O)(=O)c2ccccc2S(C)(=O)=O)cc1] | 4-[(2-Methanesulfonylbenzenesulfonamido-oxy)methyl]phenyl acetate |
| 4 | 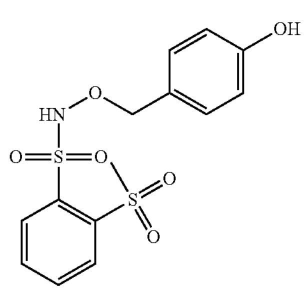 [SMILES: CS(=O)(=O)c1ccccc1S(=O)(=O)NOCc1ccc(O)cc1] | N-[(4-Hydroxyphenyl)methoxy]-2-methanesulfonylbenzene-1-sulfonamide |
| 5 | 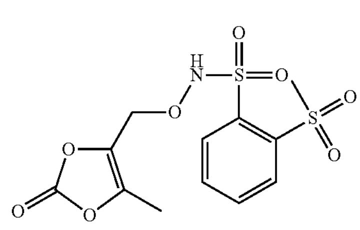 [SMILES: Cc1oc(=O)oc1CONS(=O)(=O)c1ccccc1S(C)(=O)=O] | 2-methanesulfonyl-N-[(5-methyl-2-oxo-2H-1,3-dioxol-4-yl)methoxy]benzene-1-sulfonamide |

TABLE 1-continued

| No | Structure | Name |
|---|---|---|
| 6 | 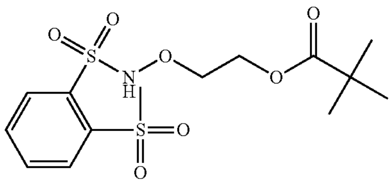 [SMILES: CC(C)(C)C(=O)OCCONS(=O)(=O)c1ccccc1S(C)(=O)=O] | 2-(2-Methanesulfonylbenzenesulfonamido-oxy)ethyl 2,2-dimethylpropanoate |
| 7 | 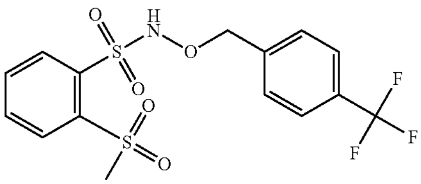 [SMILES: CS(=O)(=O)c1ccccc1S(=O)(=O)NOCc1ccc(C(F)(F)F)cc1] | 2-methanesulfonyl-N-{[4-(trifluoromethyl)phenyl]methoxy}benzene-1-sulfonamide |
| 8 | 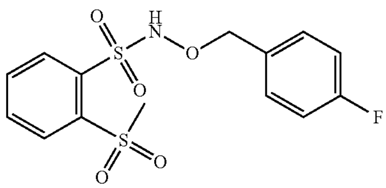 [SMILES: CS(=O)(=O)c1ccccc1S(=O)(=O)NOCc1ccc(F)cc1] | N-[(4-fluoropheyl)methoxy]-2-methanesulfonylbenzene-1-sulfonamide |
| 9 | 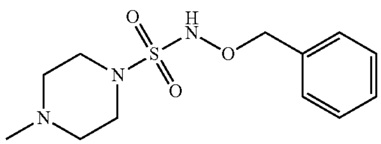 [SMILES: CN1CCN(S(=O)(=O)NOCc2ccccc2)CC1] | N-(Benzyloxy)-4-methylpiperazine-1-sulfonamide |
| 10 | 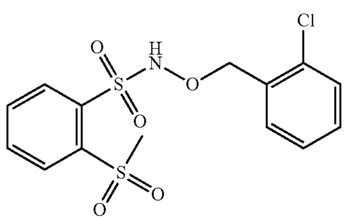 [SMILES: CS(=O)(=O)c1ccccc1S(=O)(=O)NOCc1ccccc1Cl] | N-[(2-Chlorophenyl)methoxy]-2-methanesulfonylbenzene-1-sulfonamide |
| 11 | 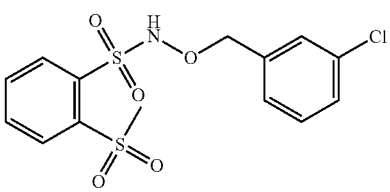 [SMILES: CS(=O)(=O)c1ccccc1S(=O)(=O)NOCc1cccc(Cl)c1] | N-[(3-Chlorophenyl)methoxy]-2-methanesulfonylbenzene-1-sulfonamide |
| 12 | 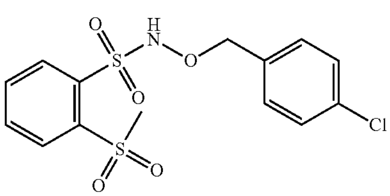 [SMILES: CS(=O)(=O)c1ccccc1S(=O)(=O)NOCc1ccc(Cl)cc1] | N-[(4-Chlorophenyl)methoxy]-2-methanesulfonylbenzene-1-sulfonamide |
| 13 | 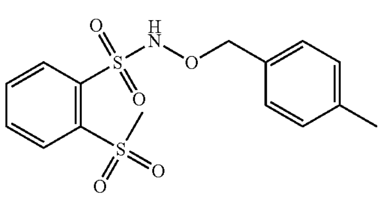 [SMILES: Cc1ccc(CONS(=O)(=O)c2ccccc2S(C)(=O)=O)cc1] | 2-Methanesulfonyl-N-[(4-methylphenyl)methoxy]benzene-1-sulfonamide |

TABLE 1-continued

| No | Structure | Name |
|---|---|---|
| 14 | 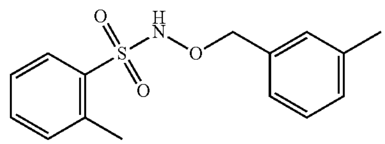 [SMILES: Cc1cccc(CONS(=O)(=O)c2ccccc2C)c1] | 2-Methyl-N-[(3-methylphenyl)methoxy]benzene-1-sulfonamide |
| 15 | 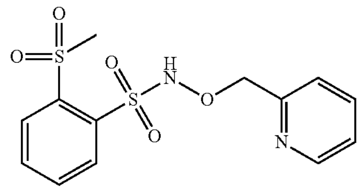 [SMILES: CS(=O)(=O)c1ccccc1S(=O)(=O)NOCc1ccccn1] | 2-Methanesulfonyl-N-(pyridin-2-ylmethoxy)benzene-1-sulfonamide |
| 16 | 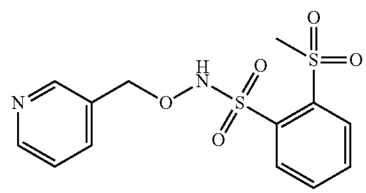 [SMILES: CS(=O)(=O)c1ccccc1S(=O)(=O)NOCc1cccnc1] | 2-Methanesulfonyl-N-(pyridin-3-ylmethoxy)benzene-1-sulfonamide |
| 17 | 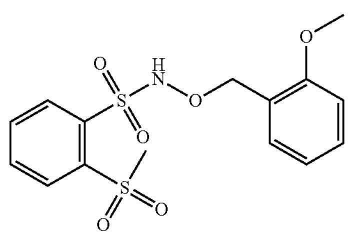 [SMILES: COc1ccccc1CONS(=O)(=O)c1ccccc1S(C)(=O)=O] | 2-Methanesulfonyl-N-[(2-methoxyphenyl)methoxy]benzene-1-sulfonamide |
| 18 | 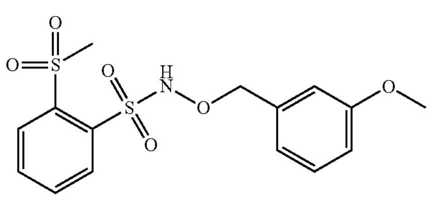 [SMILES: COc1cccc(CONS(=O)(=O)c2ccccc2S(C)(=O)=O)c1] | 2-Methanesulfonyl-N-[(3-methoxyphenyl)methoxy]benzene-1-sulfonamide |
| 19 | 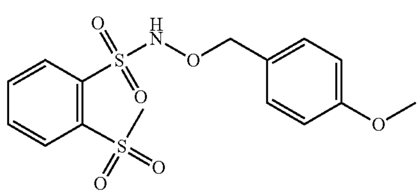 [SMILES: COc1ccc(CONS(=O)(=O)c2ccccc2S(C)(=O)=O)cc1] | 2-Methanesulfonyl-N-[(4-methoxyphenyl)methoxy]benzene-1-sulfonamide |
| 20 | 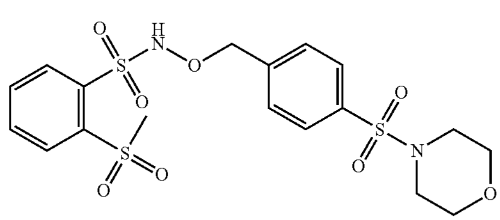 [SMILES: CS(=O)(=O)c1ccccc1S(=O)(=O)NOCc1ccc(S(=O)(=O)N2CCOCC2)cc1] | 2-methanesulfonyl-N-{[4-(morpholine-4-sulfonyl)phenyl]methoxy}benzene-1-sulfonamide |

TABLE 1-continued

| No | Structure | Name |
|---|---|---|
| 21 | 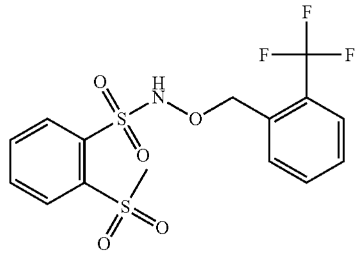 [SMILES: CS(=O)(=O)c1ccccc1S(=O)(=O)NOCc1ccccc1C(F)(F)F] | 2-Methanesulfonyl-N-{[2-(trifluoromethyl)phenyl]methoxy}benzene-1-sulfonamide |
| 22 | 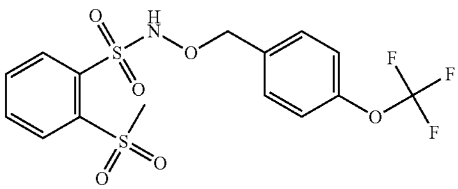 [SMILES: CS(=O)(=O)c1ccccc1S(=O)(=O)NOCc1ccc(OC(F)(F)F)cc1] | 2-Methanesulfonyl-N-{[4-(trifluoromethoxy)phenyl]methoxy}benzene-1-sulfonamide |
| 23 | 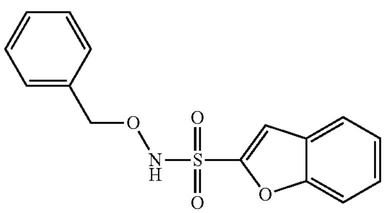 [SMILES: O=S(=O)(NOCc1ccccc1)c1cc2ccccc2o1] | N-(Benzyloxy)-1-benzofuran-2-sulfonamide |
| 24 | 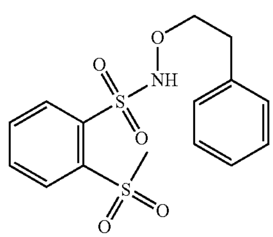 [SMILES: CS(=O)(=O)c1ccccc1S(=O)(=O)NOCCc1ccccc1] | 2-Methanesulfonyl-N-(2-phenylethoxy)benzene-1-sulfonamide |
| 25 | 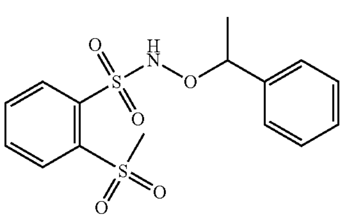 [SMILES: CC(ONS(=O)(=O)c1ccccc1S(C)(=O)=O)c1ccccc1] | 2-Methanesulfonyl-N-(1-phenylethoxy)benzene-1-sulfonamide |
| 26 | 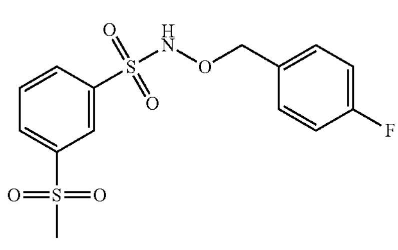 [SMILES: CS(=O)(=O)c1cccc(S(=O)(=O)NOCc2ccc(F)cc2)c1] | N-[(4-Fluorophenyl)methoxy]-3-methanesulfonylbenzene-1-sulfonamide |
| 27 | 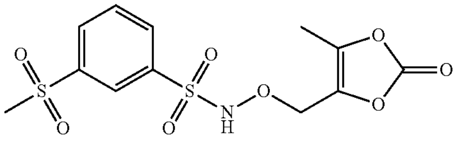 [SMILES: Cc1oc(=O)oc1CONS(=O)(=O)c1cccc(S(C)(=O)=O)c1] | 3-Methanesulfonyl-N-[(5-methyl-2-oxo-2H-1,3-dioxol-4-yl)methoxy]benzene-1-sulfonamide |

TABLE 1-continued

| No | Structure | Name |
|----|-----------|------|
| 28 | 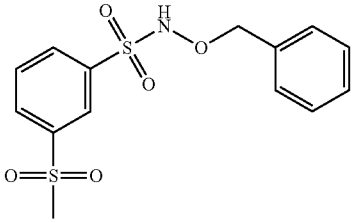 [SMILES: CS(=O)(=O)c1cccc(S(=O)(=O)NOCc2ccccc2)c1] | N-(Benzyloxy)-3-methanesulfonylbenzene-1-sulfonamide |
| 29 | 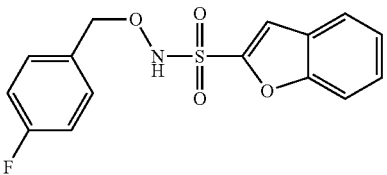 [SMILES: O=S(=O)(NOCc1ccc(F)cc1)c1cc2ccccc2o1] | N-[(4-Fluorophenyl)methoxy]-1-benzofuran-2-sulfonamide |
| 30 | 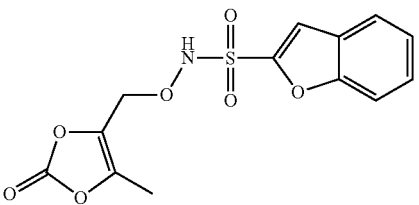 [SMILES: Cc1oc(=O)oc1CONS(=O)(=O)c1cc2ccccc2o1] | N-[(5-Methyl-2-oxo-2H-1,3-dioxol-4-yl)methoxy]-1-benzofuran-2-sulfonamide |
| 31 | 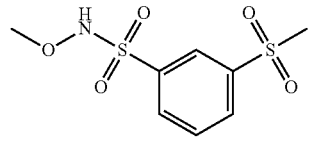 | 3-Methanesulfonyl-N-methoxybenzene-1-sulfonamide |
| 32 | 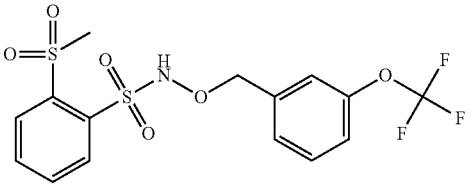 [SMILES: CS(=O)(=O)c1ccccc1S(=O)(=O)NOCc1cccc(OC(F)(F)F)c1] | 2-Methanesulfonyl-N-{[3-(trifluoromethoxy)phenyl]methoxy}benzene-1-sulfonamide |
| 33 | 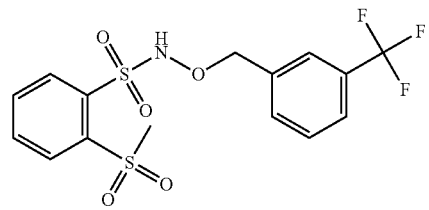 [SMILES: CS(=O)(=O)c1ccccc1S(=O)(=O)NOCc1cccc(C(F)(F)F)c1] | 2-Methanesulfonyl-N-{[3-(trifluoromethyl)phenyl]methoxy}benzene-1-sulfonamide |
| 34 | 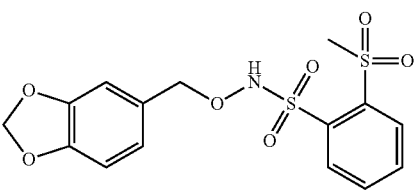 [SMILES: CS(=O)(=O)c1ccccc1S(=O)(=O)NOCc1ccc2c(c1)OCO2] | N-(2H-1,3-Benzodioxol-5-ylmethoxy)-2-methanesulfonylbenzene-1-sulfonamide |
| 35 | 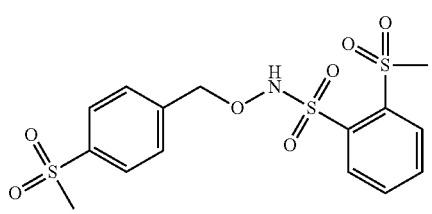 [SMILES: CS(=O)(=O)c1ccc(CONS(=O)(=O)c2ccccc2S(C)(=O)=O)cc1] | 2-Methanesulfonyl-N-[(4-methanesulfonylphenyl)methoxy]benzene-1-sulfonamide |

TABLE 1-continued

| No | Structure | Name |
|----|-----------|------|
| 36 | 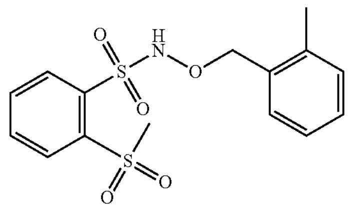 [SMILES: Cc1ccccc1CONS(=O)(=O)c1ccccc1S(C)(=O)=O] | 2-Methanesulfonyl-N-[(2-methylphenyl)methoxy]benzene-1-sulfonamide |
| 37 | 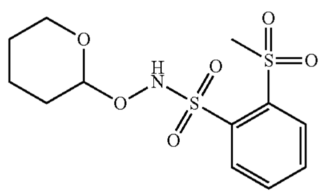 [SMILES: CS(=O)(=O)c1ccccc1S(=O)(=O)NOC1CCCCO1] | 2-Methanesulfonyl-N-(oxan-2-yloxy)benzene-1-sulfonamide |
| 38 | 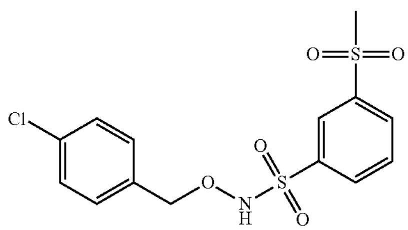 [SMILES: CS(=O)(=O)c1cccc(S(=O)(=O)NOCc2ccc(Cl)cc2)c1] | N-[(4-Chlorophenyl)methoxy]-3-methanesulfonylbenzene-1-sulfonamide |
| 39 | 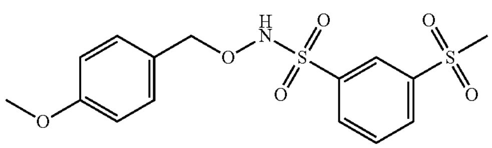 | 3-Methanesulfonyl-N-[(4-methoxyphenyl)methoxy]benzene-1-sulfonamide |
| 40 | 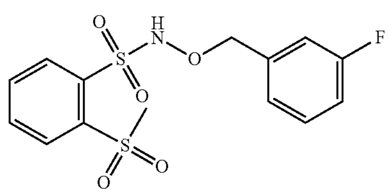 [SMILES: CS(=O)(=O)c1ccccc1S(=O)(=O)NOCc1cccc(F)c1] | N-[(3-Fluorophenyl)methoxy]-2-methanesulfonylbenzene-1-sulfonamide |
| 41 | 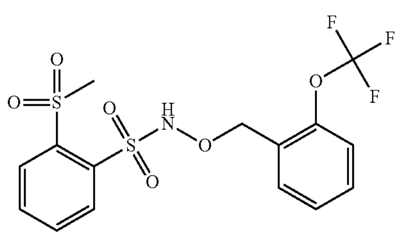 [SMILES: CS(=O)(=O)c1ccccc1S(=O)(=O)NOCc1ccccc1OC(F)(F)F] | 2-Methanesulfonyl-N-{[2-(trifluoromethoxy)phenyl]methoxy}benzene-1-sulfonamide |
| 42 | 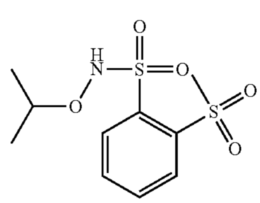 [SMILES: CC(C)ONS(=O)(=O)c1ccccc1S(C)(=O)=O] | 2-Methanesulfonyl-N-(propan-2-yloxy)benzene-1-sulfonamide |

TABLE 1-continued

| No | Structure | Name |
|---|---|---|
| 43 | 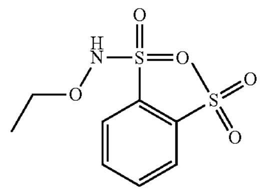 [SMILES: CCONS(=O)(=O)c1ccccc1S(C)(=O)=O] | N-Ethoxy-2-methanesulfonylbenzene-1-sulfonamide |
| 44 | 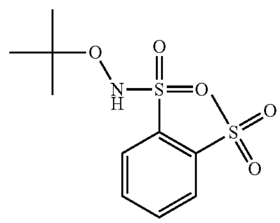 [SMILES: CC(C)(C)ONS(=O)(=O)c1ccccc1S(C)(=O)=O] | N-(tert-Butoxy)-2-methanesulfonylbenzene-1-sulfonamide |
| 45 | 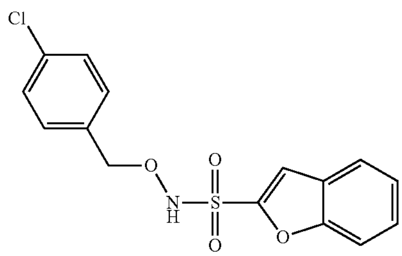 [SMILES: O=S(=O)(NOCc1ccc(Cl)cc1)c1cc2ccccc2o1] | N-[(4-Chlorophenyl)methoxy]-1-benzofuran-2-sulfonamide |
| 46 | 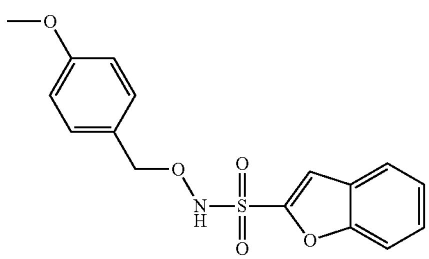 [SMILES: COc1ccc(CONS(=O)(=O)c2cc3ccccc3o2)cc1] | N-[(4-Methoxyphenyl)methoxy]-1-benzofuran-2-sulfonamide |
| 47 | 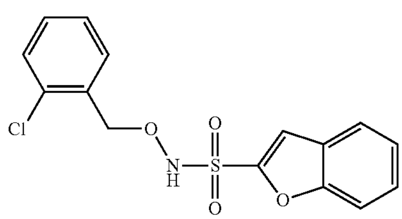 [SMILES: O=S(=O)(NOCc1ccccc1Cl)c1cc2ccccc2o1] | N-[(2-Chlorophenyl)methoxy]-1-benzofuran-2-sulfonamide |
| 48 | 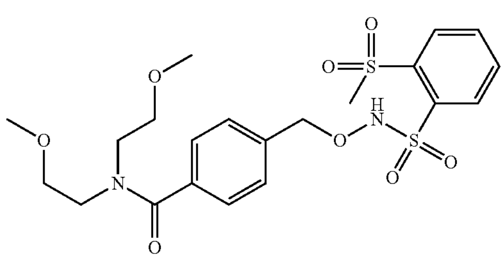 [SMILES: COCCN(CCOC)C(=O)c1ccc(CONS(=O)(=O)c2ccccc2S(C)(=O)=O)cc1] | 4-[(2-Methanesulfonylbenzenesulfonamido-oxy)methyl]-N,N-bis(2-methoxyethyl)benzamide |

TABLE 1-continued

| No | Structure | Name |
|---|---|---|
| 49 | 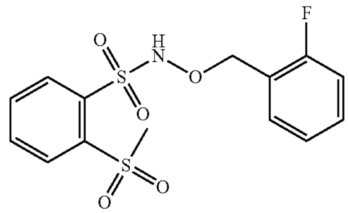 [SMILES: CS(=O)(=O)c1ccccc1S(=O)(=O)NOCc1ccccc1F] | N-[(2-Fluorophenyl)methoxy]-2-methanesulfonylbenzene-1-sulfonamide |
| 50 | 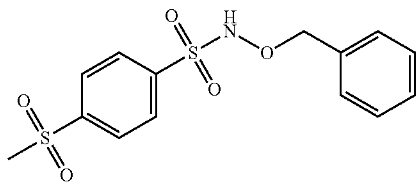 [SMILES: CS(=O)(=O)c1ccc(S(=O)(=O)NOCc2ccccc2)cc1] | N-(Benzyloxy)-4-methanesulfonylbenzene-1-sulfonamide |
| 51 | 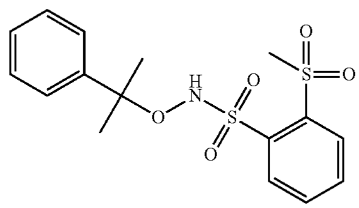 [SMILES: CC(C)(ONS(=O)(=O)c1ccccc1S(C)(=O)=O)c1ccccc1] | 2-Methanesulfonyl-N-[(2-phenylpropan-2-yl)oxy]benzene-1-sulfonamide |
| 52 | 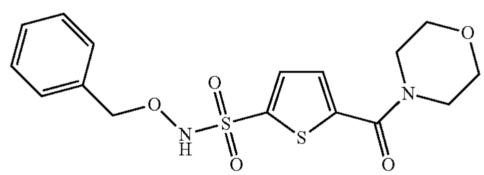 [SMILES: O=C(c1ccc(S(=O)(=O)NOCc2ccccc2)s1)N1CCOCC1] | N-(Benzyloxy)-5-(morpholine-4-carbonyl)thiophene-2-sulfonamide |
| 53 | 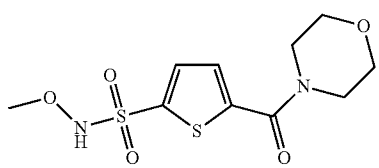 [SMILES: CONS(=O)(=O)c1ccc(C(=O)N2CCOCC2)s1] | N-Methoxy-5-(morpholine-4-carbonyl)thiophene-2-sulfonamide |
| 54 | 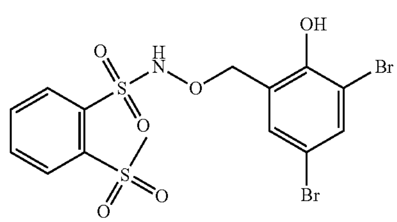 [SMILES: CS(=O)(=O)c1ccccc1S(=O)(=O)NOCc1cc(Br)cc(Br)c1O] | N-[(3,5-Dibromo-2-hydroxyphenyl)methoxy]-2-methanesulfonylbenzene-1-sulfonamide |
| 55 | 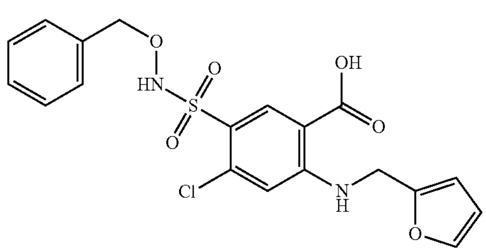 [SMILES: O=C(O)c1cc(S(=O)(=O)NOCc2ccccc2)c(Cl)cc1NCc1ccco1] | 5-[(Benzyloxy)sulfamoyl]-4-chloro-2-[(furan-2-ylmethyl)amino]benzoic acid |

TABLE 1-continued

| No | Structure | Name |
|---|---|---|
| 56 | 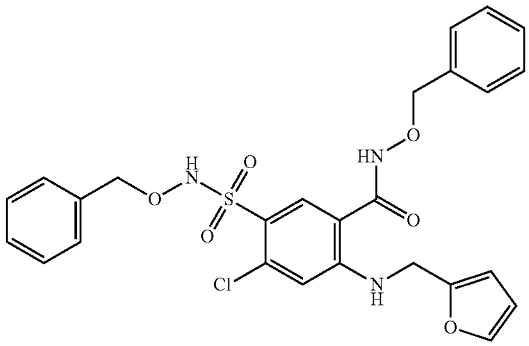 [SMILES: O=C(NOCc1ccccc1)c1cc(S(=O)(=O)NOCc2ccccc2)c(Cl)cc1NCc1ccco1] | N-(Benzyloxy)-5-[(benzyloxy)sulfamoyl]-4-chloro-2-[(furan-2-ylmethyl)amino]benzamide |
| 57 | 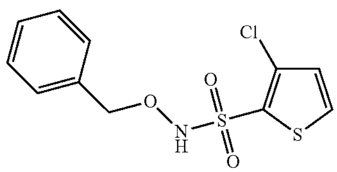 [SMILES: O=S(=O)(NOCc1ccccc1)c1sccc1Cl] | N-(Benzyloxy)-3-chlorothiophene-2-sulfonamide |
| 58 | 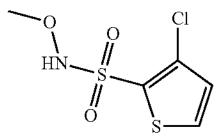 | 3-Chloro-N-methoxythiophene-2-sulfonamide |
| 59 | 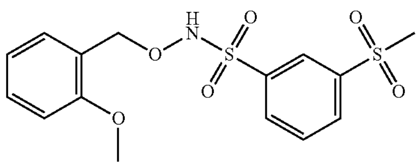 [SMILES: COc1ccccc1CONS(=O)(=O)c1cccc(S(C)(=O)=O)c1] | 3-Methanesulfonyl-N-[(2-methoxyphenyl)methoxy]benzene-1-sulfonamide |
| 60 | 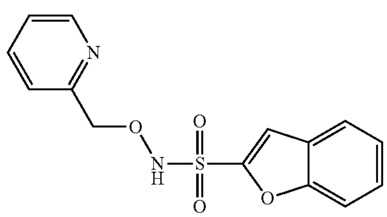 [SMILES: O=S(=O)(NOCc1ccccn1)c1cc2ccccc2o1] | N-(Pyridin-2-ylmethoxy)-1-benzofuran-2-sulfonamide |
| 61 | 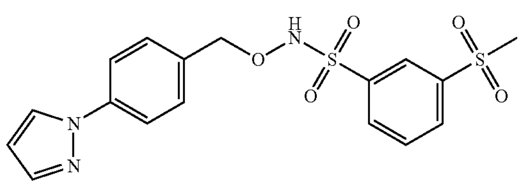 [SMILES: CS(=O)(=O)c1cccc(S(=O)(=O)NOCc2ccc(-n3cccn3)cc2)c1] | 3-Methanesulfonyl-N-{[4-(1H-pyrazol-1-yl)phenyl]methoxy}benzene-1-sulfonamide |
| 62 | 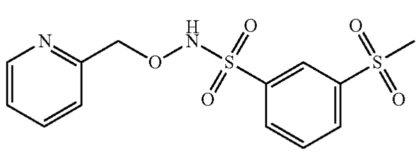 [SMILES: CS(=O)(=O)c1cccc(S(=O)(=O)NOCc2ccccn2)c1] | 3-Methanesulfonyl-N-(pyridin-2-ylmethoxy)benzene-1-sulfonamide |
| 63 | 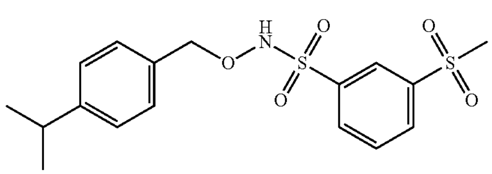 [SMILES: CC(C)c1ccc(CONS(=O)(=O)c2cccc(S(C)(=O)=O)c2)cc1] | 3-Methanesulfonyl-N-{[4-(propan-2-yl)phenyl]methoxy}benzene-1-sulfonamide |

TABLE 1-continued

| No | Structure | Name |
|----|-----------|------|
| 64 | 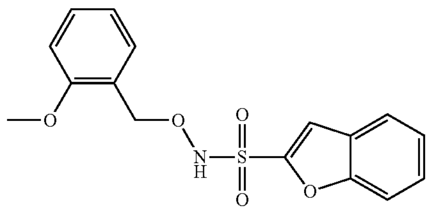 [SMILES: COc1ccccc1CONS(=O)(=O)c1cc2ccccc2o1] | N-[(2-Methoxyphenyl)methoxy]-1-benzofuran-2-sulfonamide |
| 65 | 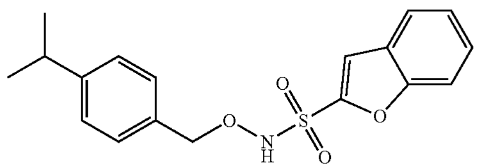 [SMILES: CC(C)c1ccc(CONS(=O)(=O)c2cc3ccccc3o2)cc1] | N-{[4-(Propan-2-yl)phenyl]methoxy}-1-benzofuran-2-sulfonamide |
| 66 | 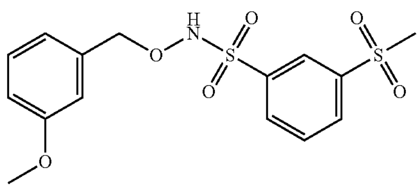 [SMILES: COc1cccc(CONS(=O)(=O)c2cccc(S(C)(=O)=O)c2)c1] | 3-Methanesulfonyl-N-[(3-methoxyphenyl)methoxy]benzene-1-sulfonamide |
| 67 | 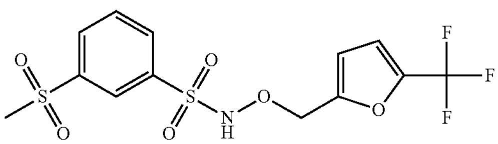 [SMILES: CS(=O)(=O)c1cccc(S(=O)(=O)NOCc2ccc(C(F)(F)F)o2)c1] | 3-Methanesulfonyl-N-{[5-(trifluoromethyl)furan-2-yl]methoxy}benzene-1-sulfonamide |
| 68 | 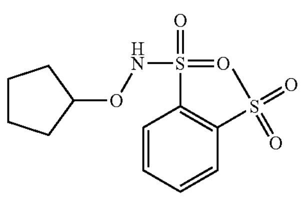 [SMILES: CS(=O)(=O)c1ccccc1S(=O)(=O)NOC1CCCC1] | N-(Cyclopentyloxy)-2-methanesulfonylbenzene-1-sulfonamide |
| 69 | 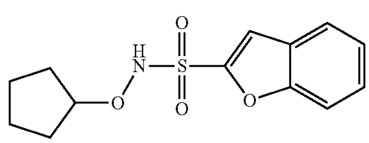 [SMILES: O=S(=O)(NOC1CCCC1)c1cc2ccccc2o1] | N-(Cyclopentyloxy)-1-benzofuran-2-sulfonamide |
| 70 | 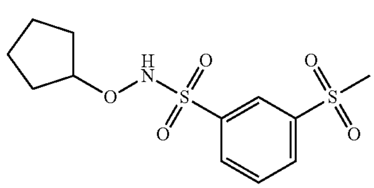 [SMILES: CS(=O)(=O)c1cccc(S(=O)(=O)NOC2CCCC2)c1] | N-(Cyclopentyloxy)-3-methanesulfonylbenzene-1-sulfonamide |
| 71 | 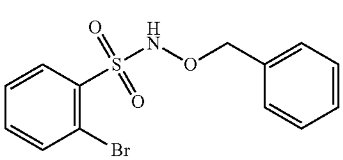 [SMILES: O=S(=O)(NOCc1ccccc1)c1ccccc1Br] | N-(Benzyloxy)-2-bromobenzene-1-sulfonamide |

TABLE 1-continued

| No | Structure | Name |
|---|---|---|
| 72 | 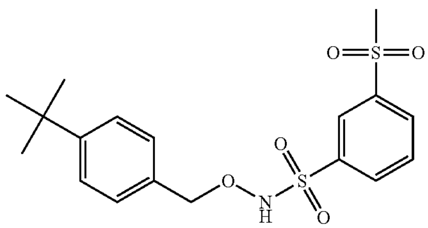 [SMILES: CC(C)(C)c1ccc(CONS(=O)(=O)c2cccc(S(C)(=O)=O)c2)cc1] | N-[(4-tert-Butylphenyl)methoxy]-3-methanesulfonylbenzene-1-sulfonamide |
| 73 | 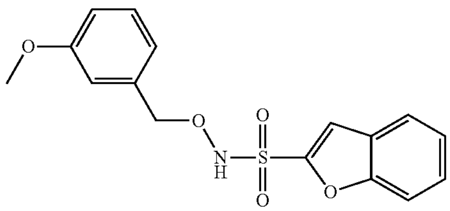 [SMILES: COc1cccc(CONS(=O)(=O)c2cc3ccccc3o2)c1] | N-[(3-Methoxyphenyl)methoxy]-1-benzofuran-2-sulfonamide |
| 74 | 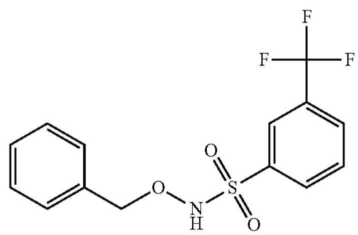 [SMILES: O=S(=O)(NOCc1ccccc1)c1cccc(C(F)(F)F)c1] | N-(Benzyloxy)-3-(trifluoromethyl)benzene-1-sulfonamide |
| 75 | 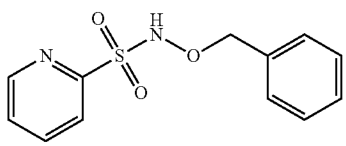 [SMILES: O=S(=O)(NOCc1ccccc1)c1ccccn1] | N-(Benzyloxy)pyridine-2-sulfonamide |
| 76 | 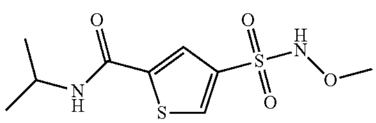 [SMILES: CONS(=O)(=O)c1csc(C(=O)NC(C)C)c1] | 4-(Methoxysulfamoyl)-N-(propan-2-yl)thiophene-2-carboxamide |
| 77 | 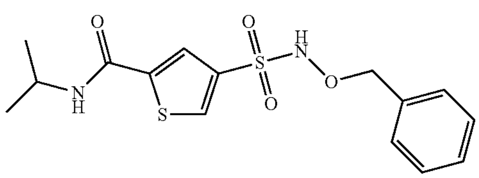 [SMILES: CC(C)NC(=O)c1cc(S(=O)(=O)NOCc2ccccc2)cs1] | 4-[(Benzyloxy)sulfamoyl]-N-(propan-2-yl)thiophene-2-carboxamide |
| 78 | 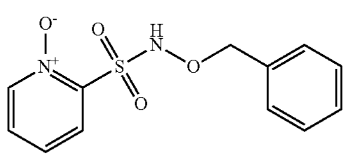 [SMILES: O=S(=O)(NOCc1ccccc1)c1cccc[n+]1[O-]] | 2-[(Benzyloxy)sulfamoyl]pyridin-1-ium-1-olate |
| 79 | 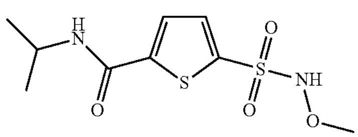 [SMILES: CONS(=O)(=O)c1ccc(C(=O)NC(C)C)s1] | 5-(Methoxysulfamoyl)-N-(propan-2-yl)thiophene-2-carboxamide |
| 80 | 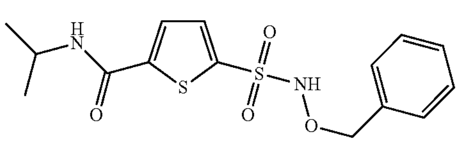 [SMILES: CC(C)NC(=O)c1ccc(S(=O)(=O)NOCc2ccccc2)s1] | 5-[(Benzyloxy)sulfamoyl]-N-(propan-2-yl)thiophene-2-carboxamide |

TABLE 1-continued

| No | Structure | Name |
|---|---|---|
| 81 | 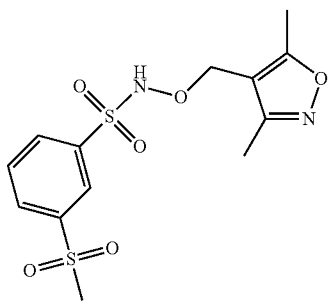 [SMILES: Cc1noc(C)c1CONS(=O)(=O)c1cccc(S(C)(=O)=O)c1] | N-[(Dimethyl-1,2-oxazol-4-yl)methoxy]-3-methanesulfonylbenzene-1-sulfonamide |
| 82 | 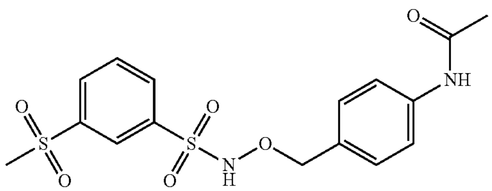 [SMILES: CC(=O)Nc1ccc(CONS(=O)(=O)c2cccc(S(C)(=O)=O)c2)cc1] | N-{4-[(3-Methanesulfonylbenzenesulfonamido-oxy)methyl]phenyl}acetamide |
| 83 | 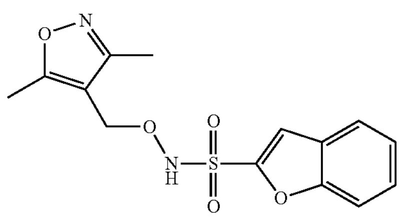 [SMILES: Cc1noc(C)c1CONS(=O)(=O)c1cc2ccccc2o1] | N-[(Dimethyl-1,2-oxazol-4-yl)methoxy]-1-benzofuran-2-sulfonamide |
| 84 | 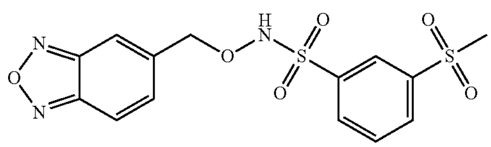 [SMILES: CS(=O)(=O)c1cccc(S(=O)(=O)NOCc2ccc3nonc3c2)c1] | N-(2,1,3-Benzoxadiazol-5-ylmethoxy)-3-methanesulfonylbenzene-1-sulfonamide |
| 85 | 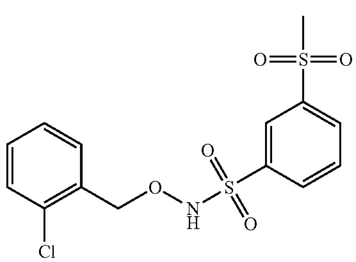 [SMILES: CS(=O)(=O)c1cccc(S(=O)(=O)NOCc2ccccc2Cl)c1] | N-[(2-Chlorophenyl)methoxy]-3-methanesulfonylbenzene-1-sulfonamide |
| 86 | 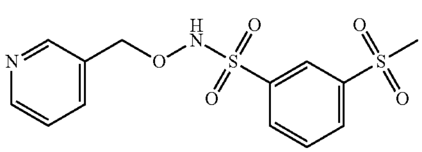 [SMILES: CS(=O)(=O)c1cccc(S(=O)(=O)NOCc2cccnc2)c1] | 3-Methanesulfonyl-N-(pyridin-3-ylmethoxy)benzene-1-sulfonamide |
| 87 | 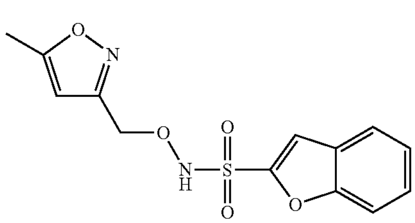 [SMILES: Cc1cc(CONS(=O)(=O)c2cc3ccccc3o2)no1] | N-[(5-Methyl-1,2-oxazol-3-yl)methoxy]-1-benzofuran-2-sulfonamide |

TABLE 1-continued

| No | Structure | Name |
|---|---|---|
| 88 | 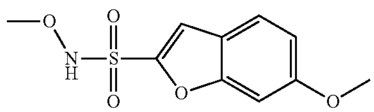 | N,6-Dimethoxy-1-benzofuran-2-sulfonamide |
| 89 | 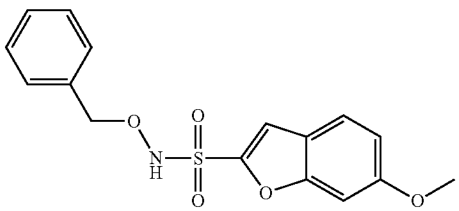 [SMILES: COc1ccc2cc(S(=O)(=O)NOCc3ccccc3)oc2c1] | N-(Benzyloxy)-6-methoxy-1-benzofuran-2-sulfonamide |
| 90 | 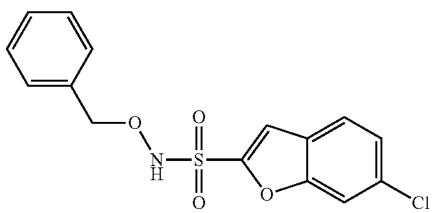 [SMILES: O=S(=O)(NOCc1ccccc1)c1cc2ccc(Cl)cc2o1] | N-(Benzyloxy)-6-chloro-1-benzofuran-2-sulfonamide |
| 91 | 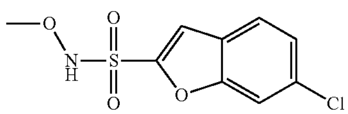 [SMILES: CONS(=O)(=O)c1cc2ccc(Cl)cc2o1] | 6-Chloro-N-methoxy-1-benzofuran-2-sulfonamide |
| 92 | 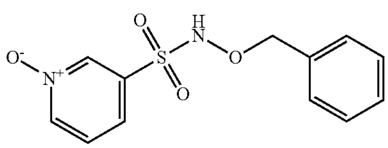 [SMILES: O=S(=O)(NOCc1ccccc1)c1ccc[n+]([O-])c1] | 3-[(Benzyloxy)sulfamoyl]pyridin-1-ium-1-olate |
| 93 | 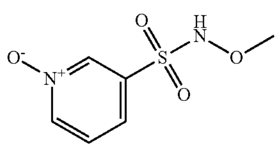 | 3-(Methoxysulfamoyl)pyridin-1-ium-1-olate |
| 94 | 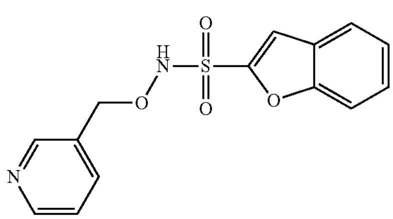 [SMILES: O=S(=O)(NOCc1cccnc1)c1cc2ccccc2o1] | N-(Pyridin-3-ylmethoxy)-1-benzofuran-2-sulfonamide |
| 95 | 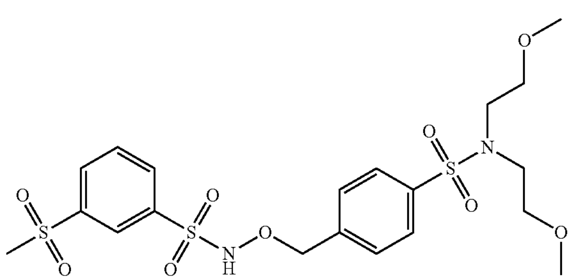 | 4-[(3-Methanesulfonylbenzenesulfonamido-oxy)methyl]-N,N-bis(2-methoxyethyl)benzene-1-sulfonamide |

TABLE 1-continued

| No | Structure | Name |
|---|---|---|
| 96 | 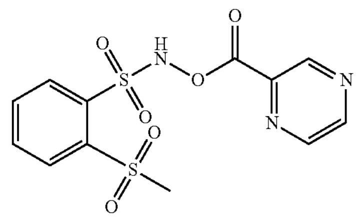 [SMILES: CS(=O)(=O)c1ccccc1S(=O)(=O)NOC(=O)c1cnccn1] | 2-Methanesulfonylbenzenesulfonamido pyrazine-2-carboxylate |

In particular embodiments, a compound from Table 1 is utilized as a pharmaceutically acceptable salt thereof.

3.3 Measuring Nitroxyl Donating Ability

Compounds are easily tested for nitroxyl donation by routine experiments. Although it is typically impractical to directly measure whether nitroxyl is donated, several analytical approaches are accepted as suitable for determining whether a compound donates nitroxyl. For example, the compound of interest can be placed in solution, for example in phosphate buffered saline ("PBS") or in a phosphate buffered solution at a pH of about 7.4, in a sealed container. After sufficient time for disassociation has elapsed, such as from several minutes to several hours, the headspace gas is withdrawn and analyzed to determine its composition, such as by gas chromatography and/or mass spectrometry. If the gas $N_2O$ is formed (which occurs by HNO dimerization), the test is positive for nitroxyl donation and the compound is deemed to be a nitroxyl donor.

Alternatively, the compound of interest can be placed in a solution of tris(4,6-dimethyl-3-sulfanatophenyl)phosphine trisodium salt (TXPTS) in e.g., a phosphate buffered solution at a pH of about 7.4. The amount of nitroxyl released from the compound of interest can be detected by monitoring the formation of TXPTS aza-ylide by $^1$H NMR. See Reisz et al., *Org. Lett.* 11:2719-2721 (2009), Reisz et al., *J. Am. Chem. Soc.* 133:11675-11685 (2011) and Guthrie et al., *J. Org. Chem.* 80:1338-1348 (2015). Accordingly, if TXPTS aza-ylide is formed, the test is positive for nitroxyl donation.

If desired, nitroxyl donation also can be detected by exposing the test compound to metmyoglobin ("$Mb^{3+}$"). See Bazylinski et al., *J. Amer. Chem. Soc.* 107(26):7982-7986 (1985). Nitroxyl reacts with $Mb^{3+}$ to form a $Mb^{2+}$-NO complex, which can be detected by changes in the ultraviolet/visible spectrum or by electron paramagnetic resonance ("EPR"). The $Mb^{2+}$-NO complex has an EPR signal centered around a g-value of about 2. Nitric oxide, on the other hand, reacts with $Mb^{3+}$ to form an $Mb^{3+}$-NO complex that has a negligible, if any, EPR signal. Accordingly, if a compound reacts with $Mb^{3+}$ to form a complex detectable by common methods, such as ultraviolet/visible or EPR, then the test is positive for nitroxyl donation.

The level of nitroxyl donating ability can be expressed as a percentage of a compound's theoretical stoichiometric maximum. A compound that donates a "significant level of nitroxyl" means, in various embodiments, a compound that donates about 40% or more, about 50% or more, about 60% or more, about 70% or more, about 80% or more, about 90% or more, or about 95% or more of its theoretical maximum amount of nitroxyl. In particular embodiments, a compound donates from about 70% to about 90% of its theoretical maximum amount of nitroxyl. In particular embodiments, a compound donates from about 85% to about 95% of its theoretical maximum amount of nitroxyl. In particular embodiments, a compound donates from about 90% to about 95% of its theoretical maximum amount of nitroxyl. Compounds that donate less than about 40%, or less than about 50%, of their theoretical maximum amount of nitroxyl are still nitroxyl donors and can be used in the methods disclosed. A compound that donates less than about 50% of its theoretical amount of nitroxyl can be used in the methods disclosed, but may require higher dosing levels as compared to a compound that donates a higher level of nitroxyl.

Testing for nitroxyl donation can be performed at a physiologically relevant pH. In particular embodiments, a compound of the disclosure is capable of donating nitroxyl at physiological pH (i.e., a pH of about 7.4) and physiological temperature (i.e., a temperature of about 37° C.) (together, "physiological conditions"). In particular embodiments, a compound of the disclosure can donate about 40% or more of its theoretical maximum (i.e., 100%) amount of nitroxyl under physiological conditions. In particular embodiments, a compound of the disclosure can donate about 50% or more of its theoretical maximum amount of nitroxyl under physiological conditions. In particular embodiments, a compound of the disclosure can donate about 60% or more of its theoretical maximum amount of nitroxyl under physiological conditions. In particular embodiments, a compound of the disclosure can donate about 70% or more of its theoretical maximum amount of nitroxyl under physiological conditions. In particular embodiments, a compound of the disclosure can donate about 80% or more of its theoretical maximum amount of nitroxyl under physiological conditions. In particular embodiments, a compound of the disclosure can donate about 90% or more of its theoretical maximum amount of nitroxyl under physiological conditions.

It will be understood that a compound of the disclosure might also donate a limited amount of nitric oxide, so long as the amount of nitroxyl donation exceeds the amount of nitric oxide donation. In certain embodiments, a compound of the disclosure can donate about 25 mole % or less of nitric oxide under physiological conditions. In particular embodiments, a compound of the disclosure can donate about 20 mole % or less of nitric oxide under physiological conditions. In particular embodiments, a compound of the disclosure can donate about 15 mole % or less of nitric oxide under physiological conditions. In particular embodiments, a compound of the disclosure can donate about 10 mole % or less of nitric oxide under physiological conditions. In particular embodiments, a compound of the disclosure can donate about 5 mole % or less of nitric oxide under physiological conditions. In particular embodiments, a compound of the disclosure can donate about 2 mole % or less of nitric oxide under physiological conditions. In particular embodiments, a compound of the disclosure can donate an insignificant amount (e.g., about 1 mole % or less) of nitric oxide under physiological conditions.

3.4 Pharmaceutical Compositions

The disclosure also encompasses pharmaceutical compositions comprising at least one compound of formula (I), (II), or (III) or a compound from Table 1 and at least one pharmaceutically acceptable excipient. Examples of pharmaceutically acceptable excipients include those described above, such as carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and any combination thereof. The selection and use of pharmaceutically acceptable excipients is taught, e.g., in Troy, Ed., *Remington: The Science and Practice of Pharmacy*, 21$^{st}$ Ed. (Lippincott Williams & Wilkins, Baltimore, Md., 2005).

In one embodiment, the at least one pharmaceutically acceptable excipient is selected from lactose, microcrystalline cellulose, croscarmellose, or any mixture thereof. In another embodiment, the at least one pharmaceutically acceptable excipient is selected from lactose, microcrystalline cellulose, croscarmellose sodium, or any mixture thereof. Lactose, the naturally-occurring disaccharide of galactose and glucose, being available in a range of varieties, e.g., granulated, sieved, milled, spray dried, and anhydrous, is a well-accepted excipient for medical and pharmaceutical uses. Reilly, "Pharmaceutical Necessities," pp. 1015-1050 in *Remington: The Science and Practice of Pharmacy* (Gennaro, ed., 20$^{th}$ ed., Lippincott, Williams & Wilkins, Baltimore, Md., 2000). Microcrystalline cellulose is disclosed to be a most resourceful excipient because of the profusion of grades available for different needs and its physical properties that support a variety of functional requirements, e.g., as a bulking agent, disintegrant, binder, lubricant, glidant, and/or stability enhancer. Baboota et al., "Microcrystalline cellulose as a versatile excipient in drug research," *J. Young Pharmacists* 1:6-12 (2009). Croscarmellose is an internally cross-linked carboxymethylcellulose; croscarmellose sodium is the sodium salt of an internally cross-linked, at least partially O-(carboxymethylated) cellulose. Either form of this excipient has reduced water solubility, attributed to the cross-linking, thus providing, inter alia, enhanced dissolution characteristics. Boylan et al., pp. 2623-2624 in *Encyclopedia of Pharmaceut. Technol.* (1$^{st}$ ed., Marcel Dekker, New York, 1988).

The pharmaceutical compositions can be formulated for administration in solid or liquid form, including those adapted for the following: (1) oral administration, for example, as drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; or (2) parenteral administration by, for example, subcutaneous, intramuscular, intravenous or epidural injection as, for example, a sterile solution or suspension. The pharmaceutical compositions can be for immediate, sustained or controlled release.

In one particular embodiment, the pharmaceutical composition is formulated for intravenous administration. In another embodiment, the pharmaceutical composition is formulated for intravenous administration by continuous infusion.

In another embodiment, the pharmaceutical composition is formulated for oral administration. In another embodiment, the pharmaceutical composition is formulated for oral administration as a liquid dosage form. In another embodiment, the pharmaceutical composition is formulated for oral administration in solid dosage form. In particular embodiments where the pharmaceutical composition is formulated as an oral liquid or solid dosage form, polyethylene glycol, such as polyethylene glycol 300 ("PEG300"), polyethylene glycol 400 ("PEG400"), and mixtures thereof, can serve as an excipient.

The pharmaceutical composition can be prepared as any appropriate unit dosage form, such as capsule, sachet, tablet, powder, granule, solution, suspension in an aqueous liquid, suspension in a non-aqueous liquid, oil-in-water liquid emulsion, water-in-oil liquid emulsion, liposomes or bolus. In one embodiment, the pharmaceutical composition is formulated as a tablet. In another embodiment, the pharmaceutical composition is formulated as a capsule.

Tablets can be made by compression or molding, optionally with one or more accessory ingredients. Compressed tablets can be prepared by compressing in a suitable machine the therapeutic agent or agents in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide slow or controlled release of the active ingredient therein. Methods of formulating such slow or controlled release compositions of pharmaceutically active ingredients, such as the therapeutic agents herein and other compounds known in the art, are known in the art and disclosed in issued U.S. patents, some of which include, but are not limited to, U.S. Pat. Nos. 4,369,174, 4,842,866, and the references cited therein. Coatings can be used for delivery of compounds to the intestine (see, e.g., U.S. Pat. Nos. 6,638,534, 5,217,720, 6,569,457, and the references cited therein). An artisan will recognize that in addition to tablets, other dosage forms can be formulated to provide slow or controlled release of the active ingredient. Such dosage forms include, but are not limited to, capsules, granulations and gel-caps.

Pharmaceutical compositions suitable for topical administration include, without limitation, lozenges comprising the ingredients in a flavored basis, such as sucrose, acacia and tragacanth; and pastilles comprising the active ingredient in a flavored basis or in an inert basis, such as gelatin and glycerin.

Various embodiments of pharmaceutical compositions suitable for parenteral administration include, without limitation, either aqueous sterile injection solutions or non-aqueous sterile injection solutions, each containing, for example, anti-oxidants, buffers, bacteriostats and solutes that render the formulation isotonic with the blood of the intended recipient; and aqueous sterile suspensions and non-aqueous sterile suspensions, each containing, for example, suspending agents and thickening agents. The formulations can be presented in unit-dose or multi-dose containers, for example, sealed ampules or vials, and can be stored in a freeze dried (lyophilized) condition requiring only the addition of a sterile liquid carrier, such as water, immediately prior to use.

Pharmaceutical compositions administered parenterally can be administered in an acidic, neutral or basic solution. In one embodiment, pharmaceutical compositions are formulated in an acidic solution having a pH of from about 4 to about 5, for instance, a pH of about 4, about 4.5, about 4.8, or about 5, including values there between. While a pH of about 4 has generally been considered optimal for formulating nitroxyl donating compositions to achieve adequate stability of the compound, it has been discovered that formulating under such acidic conditions can potentially cause or exacerbate venous irritation following parenteral administration. The amount of irritation can be attenuated by formulating the pharmaceutical compositions in less acidic or even neutral solutions. Accordingly, in particular embodiments, a pharmaceutical composition formulated for parenteral use at a pH of from about 5 to about 6.2 (e.g., pH of about 5, about 5.5, about 5.8, about 6, or about 6.2, including values there between).

3.5 Methods of Use

In one aspect, the disclosure provides a method of increasing in vivo nitroxyl levels, comprising administering to a patient in need thereof an effective amount of a compound or a pharmaceutical composition as disclosed herein. In various embodiments, the patient has, is suspected of having, or is at risk of having or developing a condition that is responsive to nitroxyl therapy.

In particular embodiments, the disclosure provides a method of treating, preventing or delaying the onset and/or development of a condition, comprising administering to a patient (including a patient identified as in need of such treatment, prevention or delay) an effective amount of a compound or a pharmaceutical composition as disclosed herein. Identifying a patient in need thereof can be in the judgment of a physician, clinical staff, emergency response personnel or other health care professional and can be subjective (e.g., opinion) or objective (e.g., measurable by a test or diagnostic method).

Particular conditions embraced by the methods disclosed herein include, without limitation, cardiovascular diseases, ischemia/reperfusion injury, and pulmonary hypertension.

3.5.1 Cardiovascular Diseases

In one embodiment, the disclosure provides a method of treating a cardiovascular disease, comprising administering an effective amount of a compound or a pharmaceutical composition as disclosed herein to a patient in need thereof.

Examples of cardiovascular diseases and symptoms that can usefully be treated with the compounds and compositions disclosed herein include cardiovascular diseases that are responsive to nitroxyl therapy, coronary obstructions, coronary artery disease ("CAD"), angina, heart attack, myocardial infarction, high blood pressure, ischemic cardiomyopathy and infarction, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, diastolic heart failure, systolic heart failure, congestive heart failure, acute congestive heart failure, acute decompensated heart failure, and cardiac hypertrophy.

3.5.1.1 Heart Failure

The compounds and compositions of the disclosure can be used to treat patients suffering from heart failure. The heart failure can be of any type or form, including any of the heart failures disclosed herein. Nonlimiting examples of heart failure include early stage heart failure, Class I, II, III and IV heart failure, acute heart failure, congestive heart failure ("CHF") and acute CHF. In one embodiment, the compounds and compositions of the disclosure can be used to treat acute decompensated heart failure.

In embodiments where the compounds and pharmaceutical compositions of the disclosure are used to treat patients suffering from heart failure, another active agent that treats heart failure can also be administered. In one such embodiment, the compound or pharmaceutical composition of the disclosure can be administered in conjunction with a positive inotrope such as a beta-agonist. Examples of beta-agonists include, without limitation, dopamine, dobutamine, isoproterenol, analogs of such compounds and derivatives of such compounds. In another embodiment, the compound or pharmaceutical composition of the disclosure can be administered in conjunction with a beta-adrenergic receptor antagonist (also referred to herein as beta-antagonist or beta-blocker). Examples of beta-antagonists include, without limitation, propranolol, metoprolol, bisoprolol, bucindolol, and carvedilol.

Compounds of the disclosure compounds can be administered as pharmaceutical formulations to patients in need of modulating in vivo nitroxyl levels. For instance, a pharmaceutical formulation comprising a compound of the disclosure can be administered to a patient intravenously.

3.5.1.2 Ischemia/Reperfusion Injury

In another embodiment, the disclosed subject matter provides a method of treating, preventing or delaying the onset and/or development of ischemia/reperfusion injury, comprising administering an effective amount of a compound or pharmaceutical composition as disclosed herein to a subject in need thereof.

In a particular embodiment, the method is for preventing ischemia/reperfusion injury. In a particular embodiment, a compound or pharmaceutical composition of the disclosure is administered prior to the onset of ischemia. In a particular embodiment, a pharmaceutical composition of the disclosure is administered prior to procedures in which myocardial ischemia can occur, for example an angioplasty or surgery, such as a coronary artery bypass graft surgery. In a particular embodiment, a pharmaceutical composition of the disclosure is administered after ischemia but before reperfusion. In a particular embodiment, a pharmaceutical composition of the disclosure is administered after ischemia and reperfusion.

In another embodiment, a pharmaceutical composition of the disclosure can be administered to a patient who is at risk for an ischemic event. In a particular embodiment, a pharmaceutical composition of the disclosure is administered to a patient at risk for a future ischemic event, but who has no present evidence of ischemia. The determination of whether a patient is at risk for an ischemic event can be performed by any method known in the art, such as by examining the patient or the patient's medical history. In a particular embodiment, the patient has had a prior ischemic event. Thus, the patient can be at risk of a first or subsequent ischemic event. Examples of patients at risk for an ischemic event include patients with known hypercholesterolemia, EKG changes associated with ischemia (e.g., peaked or inverted T-waves or ST segment elevations or depression in an appropriate clinical context), abnormal EKG not associated with active ischemia, elevated CKMB, clinical evidence of ischemia (e.g., crushing sub-sternal chest pain or arm pain, shortness of breath and/or diaphoresis), prior history of myocardial infarction ("MI"), elevated serum cholesterol, sedentary lifestyle, angiographic evidence of partial coronary artery obstruction, echocardiographic evidence of myocardial damage, or any other evidence of a risk for a future ischemic event. Examples of ischemic events include, without limitation, MI and neurovascular ischemia, such as a cerebrovascular accident ("CVA").

In another embodiment, the subject of treatment is an organ that is to be transplanted. In a particular embodiment, a pharmaceutical composition of the disclosure can be administered prior to reperfusion of the organ in a transplant recipient. In a particular embodiment, a pharmaceutical composition of the disclosure can be administered prior to removal of the organ from the donor, for example through the perfusion cannulas used in the organ removal process. If the organ donor is a live donor, for example a kidney donor, the compounds or pharmaceutical compositions of the disclosure can be administered to the organ donor. In a particular embodiment, the compounds or pharmaceutical compositions of the disclosure are administered by storing the organ in a solution comprising the compound or pharmaceutical composition. For example, a compound or pharmaceutical composition of the disclosure can be included in the organ preservation solution, such as the University of Wisconsin "UW" solution, which is a solution comprising hydroxyethyl starch substantially free of ethylene glycol, ethylene chlorohydrin and acetone (see U.S. Pat. No. 4,798,824). In a particular embodiment, a pharmaceutical composition of the disclosure that is administered is such that ischemia/reperfusion injury to the tissues of the organ is reduced upon reperfusion in the recipient of transplanted organ. In a particular embodiment, the method reduces tissue necrosis (the size of infarct) in at-risk tissues.

Ischemia/reperfusion injury can damage tissues other than those of the myocardium and the disclosed subject matter embraces methods of treating or preventing such damage. In various embodiments, the ischemia/reperfusion injury is non-myocardial. In particular embodiments, the method reduces injury from ischemia/reperfusion in the tissue of the brain, liver, gut, kidney, bowel, or any part of the body other than the myocardium. In another embodiment, the patient is at risk for such injury. Selecting a person at risk for non-myocardial ischemia could include a determination of the indicators used to assess risk for myocardial ischemia. However, other factors can indicate a risk for ischemia/reperfusion in other tissues. For example, surgery patients often experience surgery related ischemia. Thus, patients scheduled for surgery could be considered at risk for an ischemic event. The following risk factors for stroke (or a subset of these risk factors) could demonstrate a patient's risk for ischemia of brain tissue: hypertension, cigarette smoking, carotid artery stenosis, physical inactivity, diabetes mellitus, hyperlipidemia, transient ischemic attack, atrial fibrillation, CAD, CHF, past MI, left ventricular dysfunction with mural thrombus, and mitral stenosis. Ingall, *Postgrad. Med.* 107(6):34-50 (2000). Further, complications of untreated infectious diarrhea in the elderly can include myocardial, renal, cerebrovascular and intestinal ischemia. Slotwiner-Nie et al., *Gastroenterol. Clin. N. Amer.* 30(3): 625-635 (2001). Alternatively, patients could be selected based on risk factors for ischemic bowel, kidney and/or liver disease. For example, treatment would be initiated in elderly patients at risk of hypotensive episodes (such as surgical blood loss). Thus, patients presenting with such an indication would be considered at risk for an ischemic event. In another embodiment, the patient has any one or more of the conditions listed herein, such as diabetes mellitus and hypertension. Other conditions that can result in ischemia, such as cerebral arteriovenous malformation, could demonstrate a patient's risk for an ischemic event.

3.5.2 Pulmonary Hypertension

In another embodiment, a compounds or pharmaceutical composition of the disclosure can be used to prevent or delay the onset and/or development of pulmonary hypertension. In one such embodiment, a compounds or pharmaceutical composition of the disclosure can be used to prevent or delay the onset and/or development of pulmonary arterial hypertension ("PAH").

In another embodiment, the disclosed subject matter provides a method of reducing mean pulmonary arterial pressure ("MPAP"), comprising administering an effective amount of a compound or a pharmaceutical composition disclosed herein to a patient in need thereof. In another embodiment, the MPAP is reduced by up to about 50%. In another embodiment, the MPAP is reduced by up to about 25%. In another embodiment, the MPAP is reduced by up to about 20%. In another embodiment, the MPAP is reduced by up to about 15%. In another embodiment, the MPAP is reduced by up to 10%. In another embodiment, the MPAP is reduced by up to about 5%. In another embodiment, the MPAP is reduced to be from about 12 mmHg to about 16 mmHg. In another embodiment, the MPAP is reduced to be about 15 mmHg.

3.6 Administration Modes, Regimens and Dose Levels

The compounds and pharmaceutical compositions of the disclosure can be administered via parenteral (e.g., subcutaneous, intramuscular, intravenous or intradermal) administration. In certain embodiments, the compound or pharmaceutical composition is administered by intravenous infusion. In other embodiments, the compounds and pharmaceutical compositions of the disclosure can be administered by oral administration.

When a pharmaceutical composition comprising a compound of the disclosure is administered, dosages are expressed based on the amount of active pharmaceutical ingredient, i.e., the amount of compound(s) of the disclosure present in the pharmaceutical composition.

In a variety of embodiments, including various oral administration embodiments, the compounds or pharmaceutical compositions of the disclosure are administered according to a weight-based daily dosing regimen, either as a single daily dose ("QD") or in multiple divided doses administered, e.g., twice a day ("BID"), 3 times a day ("TID"), or four times a day ("QID").

In certain embodiments, the compound or pharmaceutical composition of the disclosure is administered in a dose of at least about 0.5 mg/kg/d, at least about 0.75 mg/kg/d, at least about 1.0 mg/kg/d, at least about 1.5 mg/kg/d, at least about 2 mg/kg/d, at least about 2.5 mg/kg/d, at least about 3 mg/kg/d, at least about 4 mg/kg/d, at least about 5 mg/kg/d, at least about 7.5 mg/kg/d, at least about 10 mg/kg/d, at least about 12.5 mg/kg/d, at least about 15 mg/kg/d, at least about 17.5 mg/kg/d, at least about 20 mg/kg/d, at least about 25 mg/kg/d, at least about 30 mg/kg/d, at least about 35 mg/kg/d, at least about 40 mg/kg/d, at least about 45 mg/kg/d, at least about 50 mg/kg/d, at least about 60 mg/kg/d, at least about 70 mg/kg/d, at least about 80 mg/kg/d, at least about 90 mg/kg/d, or at least about 100 mg/kg/d.

In certain embodiments, the compound or pharmaceutical composition of the disclosure is administered at a dose of no more than about 100 mg/kg/d, no more than about 100 mg/kg/d, no more than about 90 mg/kg/d, no more than about 80 mg/kg/d, no more than about 80 mg/kg/d, no more than about 75 mg/kg/d, no more than about 70 mg/kg/d, no more than about 60 mg/kg/d, no more than about 50 mg/kg/d, no more than about 45 mg/kg/d, no more than about 40 mg/kg/d, no more than about 35 mg/kg/d, no more than about 30 mg/kg/d.

In a variety of embodiments, the dose is from about 0.001 mg/kg/d to about 10,000 mg/kg/d. In certain embodiments, the dose is from about 0.01 mg/kg/d to about 1,000 mg/kg/d. In certain embodiments, the dose is from about 0.01 mg/kg/d to about 100 mg/kg/d. In certain embodiments, the dose is from about 0.01 mg/kg/d to about 10 mg/kg/d. In certain embodiments, the dose is from about 0.1 mg/kg/d to about 1 mg/kg/d. In certain embodiments, the dose is less than about 1 g/kg/d.

In certain embodiments, a compound or pharmaceutical composition of the disclosure is administered in a dose range in which the low end of the range is any amount from about 0.1 mg/kg/day to about 90 mg/kg/day and the high end of the range is any amount from about 1 mg/kg/day to about 100 mg/kg/day (e.g., from about 0.5 mg/kg/day to about 2 mg/kg/day in one series of embodiments and from about 5 mg/kg/day to about 20 mg/kg/day in another series of embodiment).

In particular embodiments, the compound or pharmaceutical composition of the disclosure is administered in a dose range of about 3 to about 30 mg/kg, administered QD, BID, or TID.

In certain embodiments, compounds or pharmaceutical compositions of the disclosure are administered according to a flat (i.e., non-weight-based) dosing regimen, either QD or in multiple divided doses administered, e.g., BID, TID, or QID.

In various embodiments, the compound or pharmaceutical composition of the disclosure is administered at a dose of at least about 0.01 grams/day (g/d), at least about 0.05 g/d, at least about 0.1 g/d, at least about 0.5 g/d, at least about 1 g/d, at least about 1.5 g/d, at least about 2.0 g/d, at least about 2.5 g/d, at least about 3.0 g/d, or at least about 3.5 g/d.

In various embodiments, the compound or pharmaceutical composition of the disclosure is administered at a dose of no more than about 5 g/d, no more than about 4.5 g/d, no more than about 4 g/d, no more than about 3.5 g/d, no more than about 3 g/d, no more than about 2.5 g/d, or no more than about 2 g/d.

In certain embodiments, the compound or pharmaceutical composition of the disclosure is administered in a dose of about 0.01 grams per day to about 4.0 grams per day. In certain embodiments, a compound or pharmaceutical composition of the disclosure can be administered at a dose in which the low end of the range is any amount from about 0.1 mg/day to about 400 mg/day and the high end of the range is any amount from about 1 mg/day to about 4000 mg/day. In certain embodiments, the compound or pharmaceutical composition is administered in a dose of about 5 mg/day to about 100 mg/day. In various embodiments, the compound or pharmaceutical composition is administered at a dose of from about 150 mg/day to about 500 mg/day.

The dosing interval for parenteral or oral administration can be adjusted according to the needs of the patient. For longer intervals between administrations, extended release or depot formulations can be used.

For intravenous administration, the dose can usefully be expressed per unit time, either as a fixed amount per unit time or as a weight-based amount per unit time.

In various embodiments, a compound or pharmaceutical composition of the disclosure is administered intravenously in an amount of at least about 0.1 µg/kg/min, at least about 0.2 µg/kg/min, at least about 0.3 µg/kg/min, at least about 0.4 µg/kg/min, at least about 0.5 µg/kg/min, at least about 1 µg/kg/min, at least about 2.5 µg/kg/min, at least about 5 µg/kg/min, at least about 7.5 µg/kg/min, at least about 10 µg/kg/min, at least about 11 µg/kg/min, at least about 12 µg/kg/min, at least about 13 µg/kg/min, at least about 14 µg/kg/min, at least about 15 µg/kg/min, at least about 16 µg/kg/min, at least about 17 µg/kg/min, at least about 18 µg/kg/min, at least about 19 µg/kg/min, at least about 20 µg/kg/min, at least about 21 µg/kg/min, at least about 22 µg/kg/min, at least about 23 µg/kg/min, at least about 24 µg/kg/min, at least about 25 µg/kg/min, at least about 26 µg/kg/min, at least about 27 µg/kg/min, at least about 28 µg/kg/min, at least about 29 µg/kg/min, at least about 30 µg/kg/min, at least about 31 µg/kg/min, at least about 32 µg/kg/min, at least about 33 µg/kg/min, at least about 34 µg/kg/min, at least about 35 µg/kg/min, at least about 36 µg/kg/min, at least about 37 µg/kg/min, at least about 38 µg/kg/min, at least about 39 µg/kg/min, or at least about 40 µg/kg/min.

In various embodiments, the compound or pharmaceutical composition of the present disclosure is administered intravenously in an amount of no more than about 100 µg/kg/min, no more than about 90 µg/kg/min, no more than about 80 µg/kg/min, no more than about 70 µg/kg/min, no more than about 60 µg/kg/min, no more than about 50 µg/kg/min, no more than about 49 µg/kg/min, no more than about 48 µg/kg/min, no more than about 47 µg/kg/min, no more than about 46 µg/kg/min, no more than about 45 µg/kg/min, no more than about 44 µg/kg/min, no more than about 43 µg/kg/min, no more than about 42 µg/kg/min, no more than about 41 µg/kg/min, no more than about 40 µg/kg/min, no more than about 39 µg/kg/min, no more than about 38 µg/kg/min, no more than about 37 µg/kg/min, no more than about 36 µg/kg/min, no more than about 35 µg/kg/min, no more than about 34 µg/kg/min, no more than about 33 µg/kg/min, no more than about 32 µg/kg/min, no more than about 31 µg/kg/min, or no more than about 30 µg/kg/min.

In some embodiments, the compound or pharmaceutical composition of the present disclosure is administered intravenously in an amount ranging from about 0.1 µg/kg/min to about 100 µg/kg/min, about 1 µg/kg/min to about 100 µg/kg/min, about 2.5 µg/kg/min to about 100 µg/kg/min, about 5 µg/kg/min to about 100 µg/kg/min, about 10 µg/kg/min to about 100 µg/kg/min, about 1.0 µg/kg/min to about 80 µg/kg/min, from about 10.0 µg/kg/min to about 70 µg/kg/min, from about 20 µg/kg/min to about 60 µg/kg/min, from about 15 µg/kg/min to about 50 µg/kg/min, from about 0.01 µg/kg/min to about 1.0 µg/kg/min, from about 0.01 µg/kg/min to about 10 µg/kg/min, from about 0.1 µg/kg/min to about 1.0 µg/kg/min, from about 0.1 µg/kg/min to about 10 µg/kg/min, from about 1.0 µg/kg/min to about 5 µg/kg/min, from about 70 µg/kg/min to about 100 µg/kg/min, or from about 80 µg/kg/min to about 90 µg/kg/min.

In particular embodiments, the compound or pharmaceutical composition of the present disclosure is administered intravenously in an amount ranging from about 10 µg/kg/min to about 50 µg/kg/min, about 20 µg/kg/min to about 40 µg/kg/min, about 25 µg/kg/min to about 35 µg/kg/min, or about 30 µg/kg/min to about 40 µg/kg/min. In particular embodiments, a compound or pharmaceutical composition of the present disclosure is administered intravenously in an amount of from about 20 µg/kg/min to about 30 µg/kg/min.

A compound or pharmaceutical composition as disclosed herein can be administered prior to, at substantially the same time with, or after administration of an additional therapeutic agent. The administration regimen can include pretreatment and/or co-administration with the additional therapeutic agent. In such case, the compound or pharmaceutical composition and the additional therapeutic agent can be administered simultaneously, separately, or sequentially.

Examples of administration regimens include without limitation: administration of each compound, pharmaceutical composition or therapeutic agent in a sequential manner; and co-administration of each compound, pharmaceutical composition or therapeutic agent in a substantially simultaneous manner (e.g., as in a single unit dosage form) or in multiple, separate unit dosage forms for each compound, pharmaceutical composition or therapeutic agent.

It will be appreciated by those in the art that the "effective amount" or "dose" ("dose level") will depend on various factors such as the particular administration mode, administration regimen, compound, and pharmaceutical composition selected, as well as the particular condition and patient being treated. For example, the appropriate dose level can vary depending upon the activity, rate of excretion and potential for toxicity of the specific compound or pharmaceutical composition employed; the age, body weight, general health, gender and diet of the patient being treated; the frequency of administration; the other therapeutic agent(s) being co-administered; and the type and severity of the condition.

3.7 Kits Comprising the Compounds or Pharmaceutical Compositions

The disclosure provides kits comprising a compound or a pharmaceutical composition disclosed herein. In a particular embodiment, the kit comprises a compound or a pharmaceutical composition disclosed herein, each in dry form, and a pharmaceutically acceptable liquid diluent.

In particular embodiments, either a compound in dry form or a pharmaceutical composition in dry form contains about 2.0% or less water by weight, about 1.5% or less water by weight, about 1.0% or less water by weight, about 0.5% or less water by weight, about 0.3% or less water by weight, about 0.2% or less water by weight, about 0.1% or less water by weight, about 0.05% or less water by weight, about 0.03% or less water by weight, or about 0.01% or less water by weight.

Pharmaceutically acceptable liquid diluents are known in the art and include but are not limited to sterile water, saline solutions, aqueous dextrose, glycerol, glycerol solutions, and the like. Other examples of suitable liquid diluents are disclosed by Nairn, "Solutions, Emulsions, Suspensions and Extracts," pp. 721-752 in *Remington: The Science and Practice of Pharmacy,* 20th Ed. (Lippincott Williams & Wilkins, Baltimore, Md., 2000).

In one embodiment, the kit further comprises instructions for using the compound or pharmaceutical composition. The instructions can be in any appropriate form, such as written or electronic form. In another embodiment, the instructions can be written instructions. In another embodiment, the instructions are contained in an electronic storage medium (e.g., magnetic diskette or optical disk). In another embodiment, the instructions include information as to the compound or pharmaceutical composition and the manner of administering the compound or pharmaceutical composition to a patient. In another embodiment, the instructions relate to a method of use disclosed herein (e.g., treating, preventing and/or delaying onset and/or development of a condition selected from cardiovascular diseases, ischemia/reperfusion injury, pulmonary hypertension and other conditions responsive to nitroxyl therapy).

In another embodiment, the kit further comprises suitable packaging. Where the kit comprises more than one compound or pharmaceutical composition, the compounds or pharmaceutical compositions can be packaged patiently in separate containers, or combined in one container when cross-reactivity and shelf life permit.

Should there be doubt over the agreement of a depicted chemical structure and a chemical name, the chemical name governs.

4. EXAMPLES

The following examples are presented for illustrative purposes and should not serve to limit the scope of the disclosed subject matter.

4.1 Synthesis of N-Hydroxylsulfonamide Derivative Compounds

General Method 1

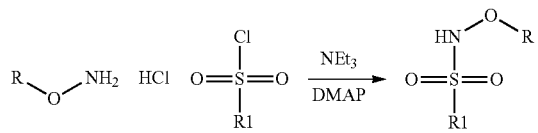

To a solution of an O-substituted hydroxylamine (1 equiv.) in DCM (20 vol.) was added trimethylamine (2 equiv.) and the reaction mixture was stirred at room temperature for 15 minutes. To the reaction mixture was added dimethyl aminopyridine (0.1 equiv.) and a sulfonyl chloride (1 equiv.) and stirring was continued for a further 30 minutes (or until complete reaction was observed by LC-MS or tlc). The reaction was quenched by addition of water and the organics dried over sodium sulfate, filtered and concentrated under reduced pressure to yield the crude product which was purified by a standard method(s) including silica gel column chromatography or reverse phase HPLC.

Table 2 provides compounds synthesized according to General Method 1.

TABLE 2

| No. | $^1$H NMR | % Purity | LC-MS (min) | Mass ion observed | Mass |
|---|---|---|---|---|---|
| 2 | $^1$H NMR (500 MHz, CHLOROFORM-d) d ppm 8.95 (1H, s), 8.27-8.42 (2H, m), 7.76-7.95 (2H, m), 3.81 (3H, s), 3.42 (3H, s) | 100 | 1.67 | [M + Na]$^+$ | 288 |
| 7 | $^1$H NMR (500 MHz, CHLOROFORM-d) d ppm 8.93 (1H, s), 8.36-8.39 (1H, m), 8.32-8.36 (1H, m), 7.85-7.91 (2H, m), 7.61 (2H, | 100 | 2.19 | [M − H]$^-$ | 408 |

TABLE 2-continued

| No. | ¹H NMR | % Purity | LC-MS (min) | Mass ion observed | Mass |
|---|---|---|---|---|---|
|  | m, J = 8.0 Hz), 7.44 (2H, m, J = 8.0 Hz), 5.06 (2 H, s), 3.42 (3H, s) |  |  |  |  |
| 8 | ¹H NMR (500 MHz, CHLOROFORM-d) d ppm 8.84 (1H, s), 8.28-8.42 (2H, m), 7.81-7.91 (2H, m), 7.31 (2H, dd, J = 8.5, 5.4 Hz), 7.03 (2H, t, J = 8.7 Hz), 4.97 (2H, s), 3.42 (3 H, s) | 97 | 2.05 | [M + H]⁺ | 360 |
| 9 | ¹H NMR (500 MHz, CHLOROFORM-d) d ppm 7.32-7.42 (5H, m), 7.07 (1H, s), 4.93 (2H, s), 3.38-3.51 (4H, m), 2.43-2.51 (4H, m), 2.32 (3H, s) | 100 | 1.17 | [M + H]⁺ | 286 |
| 13 | ¹H NMR (500 MHz, CHLOROFORM-d) d ppm 8.84 (1H, s), 8.38 (1H, dd, 5.8, 3.4 Hz), 8.31 (1H, dd, 5.8, 3.3 Hz), 7.84 (2H, dd, 5.8, 3.4 Hz), 7.19-7.25 (2H, m), 7.15 (2H, d, 7.9 Hz), 4.97 (2H, s), 3.41 (3H, s), 2.34 (3H, s) | 100 | 2.14 | [M + H]⁺ | 356 |
| 17 | ¹H NMR (500 MHz, CHLOROFORM-d) d ppm 8.79 (1H, s), 8.35-8.41 (1H, m), 8.27-8.33 (1H, m), 7.80-7.87 (2H, m), 7.30 (2H, d, J = 7.4 Hz), 6.92 (1H, t, J = 7.5 Hz), 6.86 (1 H, d, J = 8.4 Hz), 5.09 (2H, s), 3.82 (3H, s), 3.41 (3H, s) | 95 | 2.04 | [M + H]⁺ | 372 |
| 18 | ¹H NMR (500 MHz, CHLOROFORM-d) d ppm 8.89 (1H, s), 8.35-8.42 (1H, m), 8.28-8.35 (1H, m), 7.80-7.89 (2H, m), 7.22-7.26 (1H, m), 6.82-6.93 (3H, m), 4.99 (2H, s), 3.80 (3H, s), 3.42 (3 H s) | 97 | 2.03 | [M + H]⁺ | 372 |
| 19 | ¹H NMR (500 MHz, CHLOROFORM-d) d ppm 8.83 (1H, s), 8.38 (1H, dd, J = 5.8, 3.4 Hz), 8.28-8.35 (1H, m), 7.81-7.89 (2H, m), 7.24-7.31(2H, m), 6.87 (2H, d, J = 8.7 Hz), 4.96 (2H, s), 3.81 (3H, s), 3.42 (3H, s) | 98 | 2.02 | [M + Na]⁺ | 394 |
| 31 | ¹H NMR (500 MHz, CHLOROFORM-d) d ppm 8.50 (1H, s), 8.18-8.30 (2H, m), 7.81 (1H, t, J = 7.8 Hz), 7.29 (1H, s), 3.86 (3H, s), 3.13 (3H, s) | 100 | 1.29 | [M − H]⁻ | 264 |
| 42 | ¹H NMR (500 MHz, CHLOROFORM-d) d ppm 8.61 (1H, s), 8.27-8.41 (2H, m), 7.80-7.93 (2H, m), 4.30 (1H, spt, J = 6.2 Hz), 3.44 (3H, s), 1.17 (6H, d, J = 6.1 Hz) | 100 | 1.96 | [M + Na]⁺ | 316 |
| 43 | ¹H NMR (500 MHz, CHLOROFORM-d) d ppm 8.80 (1H, s), 8.29-8.39 (2H, m), 7.80-7.94 (2H, m), 4.07 (2H, q, J = 7.0 Hz), 3.43 (3 H, s), 1.18 (3H, t, J = 7.0 Hz) | 100 | 1.82 | [M + Na]⁺ | 302 |
| 44 | ¹H NMR (500 MHz, CHLOROFORM-d) d ppm 8.40 (1H, s), 8.32-8.36 (1H, m), 8.28-8.32 (1H, m), 7.82-7.88 (2H, m), 3.44 (3H, s), 1.23 (9H, s) | 99 | 2.04 | [M + Na]⁺ | 330 |
| 50 | ¹H NMR (500 MHz, CHLOROFORM-d) d ppm 8.08-8.16 (4H, m), 7.33-7.41 (5H, m), 7.03 (1H, br. s.), 5.03 (2H, s), 3.10 (3H, s) | 100 | 1.85 | [M − H]⁻ | 340 |

General Method 2

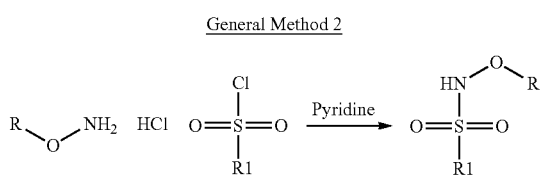

To a solution of an O-substituted hydroxylamine (1 equiv.) in DCM (20 vol.) was added pyridine (2 equiv.) and the reaction mixture was stirred at room temperature for 15 minutes. To the reaction mixture was added a sulfonyl chloride (1 equiv.) and stirring was continued for a further 30 minutes (or until complete reaction was observed by LC-MS or tlc). The reaction was quenched by addition of water and the organics dried over sodium sulfate, filtered and concentrated under reduced pressure to yield the crude product which was purified by a standard method(s) including silica gel column chromatography or reverse phase HPLC.

Table 3 provides compounds synthesized according to General Method 2.

TABLE 3

| No. | ¹H NMR | % Purity | LC-MS (min) | Mass ion observed | Mass |
|---|---|---|---|---|---|
| 52 | ¹H NMR (500 MHz, CHLOROFORM-d) d ppm 7.63 (1H, d, J = 3.9 Hz), 7.35-7.42 (5H, m), 7.24 (1H, d, J = 3.9 Hz), 7.01 (1H, s), 5.06 (2H, s), 3.73 (8H, s) | 96 | 1.81 | [M + H]⁺ | 383 |
| 53 | ¹H NMR (500 MHz, CHLOROFORM-d) d ppm 7.64 (1H, d, J = 3.9 Hz), 7.23-7.26 (2H, m), 3.88 (3H, s), 3.75 (8H, s) | 95 | 1.41 | [M + H]⁺ | 307 |
| 57 | ¹H NMR (CDCl3, 500 MHz) d 7.64 (1H, d, J = 5.3 Hz), 7.41 (1H, s), 7.38-7.32 (5H, m), 7.07 (1H, d, J = 5.3 Hz), 5.02 (2H, s) | 100 | 2.00 | [M − H]⁻ | 302 |
| 58 | ¹H NMR (CDCl3, 500 MHz) d 7.66 (1H, d, J = 5.3 Hz), 7.54 (1H, s), 7.10 (1H, d, J = 5.3 Hz), 3.84 (3H, s) | 100 | 1.61 | [M − H]⁻ | 226 |
| 68 | ¹H NMR (CDCl3, 500 MHz) d 8.61 (1H, s), 8.35-8.28 (2H, m), 7.90-7.81 (2H, m), 4.68-4.62 (1H, m), 3.42 (3H, s), 1.79-1.63 (4H, m), 1.61-1.45 (4H, m) | 100 | 2.13 | [M + Na]⁺ | 342 |
| 69 | ¹H NMR (CDCl3, 500 MHz) d 7.73 (1H, d, J = 7.9 Hz), 7.61-7.55 (2H, m), 7.53-7.48 (1H, m), 7.40-7.35 (1H, m), 7.19 (1H, s), 4.69-4.63 (1H, m), 1.84-1.67 (4H, m), 1.64-1.47 (4H, m) | 100 | 2.12 | [M − H]⁻ | 280 |
| 70 | ¹H NMR (CDCl3, 500 MHz) d 8.48 (1H, d, J = 1.6 Hz), 8.21 (2H, dd, J = 15.2, 7.9 Hz), 7.80 (1H, t, J = 7.8 Hz), 6.90 (1H, s), 4.70-4.62 (1H, m), 3.12 (3H, s), 1.85-1.68 (4H, m), 1.66-1.47 (4H, m) | 100 | 1.85 | [M − H]⁻ | 318 |
| 71 | ¹H NMR (CDCl3, 500 MHz) d 8.25 (1H, dd, J = 7.8, 1.7 Hz), 7.89 (1H, s), 7.74 (1H, dd, J = 7.8, 1.1 Hz), 7.53 (1H, td, J = 7.7, 1.2 Hz), 7.48 (1H, td, J = 7.7, 1.8 Hz), 7.37-7.30 (5H, m), 4.99 (2H, s) | 100 | 2.06 | [M − H]⁻ | 340/342 |
| 74 | ¹H NMR (500 MHz, DMSO-d6) d ppm 10.71 (1H, s), 8.18 (1H, d, 7.9 Hz), 8.11-8.16 (2H, m), 7.91 (1H, t, 8.0 Hz), 7.30-7.42 (5H, m), 4.92 (2H, s) | 95 | 2.31 | [M − H]⁻ | 330 |
| 75 | ¹H NMR (500 MHz, DMSO-d6) d ppm 10.99 (1H, s), 8.66-8.92 (1H, m), 8.11-8.19 (1H, m), 8.03-8.11 (1H, m), 7.73 (1H, ddd, 7.5, 4.7, 1.0 Hz), 7.21-7.46 (5H, m), 4.87 (2H, s) | 100 | 1.94 | [M + H]⁺ | 265 |
| 76 | ¹H NMR (CDCl3, 500 MHz) d 8.17 (1H, d, J = 1.2 Hz), 7.66 (1H, d, J = 1.2 Hz), 7.18 (1H, s), 5.91 (1H, d, J = 7.0 Hz), 4.25 (1H, dq, J = 13.3, 6.6 Hz), 3.85 (3H, s), 1.27 (6H, d, J = 6.6 Hz) | 100 | 1.55 | [M + H]⁺ | 279 |
| 77 | ¹H NMR (CDCl3, 500 MHz) d 8.14 (1H, d, J = 1.3 Hz), 7.61 (1H, d, J = 1.3 Hz), 7.40-7.32 (5H, m), 7.11 (1H, s), 5.88 (1H, d, J = 7.6 Hz), 5.00 (2H, s), 4.28-4.14 (1H, m), 1.25 (6H, d, J = 6.6 Hz) | 99 | 1.93 | [M + H]⁺ | 355 |
| 79 | ¹H NMR (DMSO, 500 MHz) d 10.77 (1H, s), 8.61 (1H, d, J = 7.6 Hz), 7.83 (1H, d, J = 4.0 Hz), 7.68 (1H, dd, J = 4.0, 2.1 Hz), 4.04 (1H, dq, J = 13.3, 6.6 Hz), 3.70 (3H, s), 1.16 (6H, d, J = 6.6 Hz) | 99 | 1.61 | [M + H]⁺ | 279 |
| 80 | ¹H NMR (CDCl3, 500 MHz) d 7.62 (1H, d, J = 4.0 Hz), 7.40-7.33 (6H, m), 7.14 (1H, s), 5.82 (1H, d, J = 7.5 Hz), 5.03 (2H, s), 4.29-4.17 (1H, m), 1.26 (6H, d, J = 6.6 Hz) | 100 | 2.1 | [M + H]⁺ | 355 |
| 85 | ¹H NMR (300 MHz, DMSO-d6) d ppm 10.83 (1H, s), 8.36 (1H, s), 8.29 (1H, d, 7.9 Hz), 8.21 (1H, d, 8.0 Hz), 7.89-8.00 (1H, m), 7.32-7.54 (4H, m), 5.05 (2H, s), 3.34 (3H, s) | 100 | 2.79 | [M − H]⁻ | 374 |
| 86 | ¹H NMR (300 MHz, DMSO-d6) d ppm 10.77 (1H, s), 8.57 (2H, br. s.), 8.34 (1H, s), 8.30 (1H, d, 7.9 Hz), 8.21 (1H, d, 7.9 Hz), 7.91-8.00 (1H, m), 7.78 (1H, d, 7.7 Hz), 7.42 (1H, dd, 7.4, 4.9 Hz), 4.98 (2H, s), 3.32 (3H, s) | 100 | 1.51 | [M + H]⁺ | 343 |
| 87 | ¹H NMR (300 MHz, DMSO-d6) d ppm 11.36 (1H, s), 7.81-7.90 (2H, m), 7.77 (1H, d, 8.4 Hz), 7.53-7.64 (1H, m), 7.38-7.50 (1H, m), 6.26 (1H, s), 4.94 (2H, s), 2.38 (3H, s) | 100 | 2.71 | [M + H]⁺ | 309 |
| 88 | ¹H NMR (300 MHz, CHLOROFORM-d) d ppm 7.52-7.62 (2H, m), 7.39 (1H, s), 7.00 (1H, dd, 8.7, 2.2 Hz), 3.89 (3H, s), 3.85 (3H, s) | 100 | 2.57 | [M + Na]⁺ | 280 |

TABLE 3-continued

| No. | $^1$H NMR | % Purity | LC-MS (min) | Mass ion observed | Mass |
|---|---|---|---|---|---|
| 89 | $^1$H NMR (300 MHz, DMSO-d6) d ppm 11.08 (1H, s), 7.56-7.81 (2H, m), 7.22-7.47 (6H, m), 7.03 (1H, dd, 8.7, 1.8 Hz), 4.91 (2H, s), 3.84 (3H, s) | 100 | 3.08 | [M + H]$^+$ | 334 |
| 90 | $^1$H NMR (300 MHz, CHLOROFORM-d) d ppm 7.63 (1H, d, 8.5 Hz), 7.57 (2H, s), 7.29-7.42 (6H, m), 5.02 (2H, s) | 100 | 3.32 | [M − H]$^−$ | 336 |
| 91 | $^1$H NMR (300 MHz, CHLOROFORM-d) d ppm 7.65 (1H, d, 8.5 Hz), 7.53-7.61 (2H, m), 7.48 (1H, s), 7.37 (1H, dd, 8.5, 1.7 Hz), 3.86 (3H, s) | 93 | 1.94 | | |
| 94 | $^1$H NMR (300 MHz, DMSO-d6) d ppm 11.23 (1H, s), 8.50-8.59 (2H, m), 7.71-7.90 (4H, m), 7.51-7.63 (1H, m), 7.36-7.50 (2H, m), 4.98 (2H, s) | 97 | 2.00 | | |

General Method 3: Phthalimide protected hydroxylamines

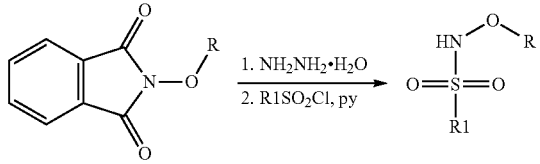

To a solution of an N-alkoxyphthalimide (1 equiv.) in THF (10 vol.) was added hydrazine hydrate (1.1 equiv.) and the resulting solution was stirred until precipitation was observed (c.a. 30 minutes). To the resulting suspension was added a sulfonyl chloride (1 equiv.) and pyridine (1 equiv.) and the reaction mixture was stirred until complete consumption of the sulfonyl chloride was observed by LC-MS. The reaction was quenched by the addition of water (5 vol.) and extracted into DCM (10-30 vol.). The insoluble phthalazine was removed by filtration and the resulting filtrate washed with water (5 vol.) and brine (5 vol.) before being dried over sodium sulfate, filtered and evaporated to dryness. The crude product was purified by a standard method(s) including silica gel column chromatography or reverse phase HPLC.

Phthalimide protected hydroxylamines were synthesized according to the method detailed in *J. Org. Chem.*, 1997, 26, 9177-9181. Table 4 provides phthalimide protected hydroxylamines used in General Method 3 and Table 5 provides compounds of the disclosure synthesized according to General Method 3.

TABLE 4

| Example No. | Name | $^1$H NMR |
|---|---|---|
| 3, 4 | 4-{[(1,3-Dioxo-2,3-dihydro-1H-isoindol-2-yl)oxy]methyl}phenyl acetate | $^1$H NMR (250 MHz, DMSO-d6) δ ppm 7.80-7.93 (4H, m), 7.48-7.62 (2H, m), 7.07-7.23 (2H, m), 5.17 (2H, s), 2.27 (3H, s) |
| 5 | 2-[(5-Methyl-2-oxo-2H-1,3-dioxol-4-yl)methoxy]-2,3-dihydro-1H-isoindole-1,3-dione | $^1$H NMR (500 MHz, DMSO-d6) δ ppm 7.89 (4H, d, 2.4Hlz), 5.08 (2H, s), 2.05 (3H, s) |
| 6 | 2-[(1,3-Dioxo-2,3-dihydro-1H-isoindol-2-yl)oxy]ethyl acetate | $^1$H NMR (250 MHz, CHLOROFORM-d) δ ppm 7.81-7.88 (2H, m), 7.72-7.81 (2H, m), 4.43 (4H, s), 1.19 (9H, s) |
| 20 | 2-{[4-(Morpholine-4-sulfonyl)phenyl]methoxy}-2,3-dihydro-1H-isoindole-1,3-dione | $^1$H NMR (500 MHz, DMSO-D6) δ ppm 7.83-7.89 (4H, m), 7.75-7.83 (4H, m), 5.30 (2H, s), 3.60-3.65 (4H, m), 2.81-2.87 (4H, m) |
| 35 | 2-[(4-Methanesulfonylphenyl)methoxy]-2,3-dihydro-1H-isoindole-1,3-dione | $^1$H NMR (500 MHz, CDCl$_3$) δ ppm 7.98 (d, J = 8.3 Hz, 2H), 7.87-7.80 (m, 2H), 7.80-7.74 (m, 4H), 5.31 (s, 2H), 3.06 (s, 3H). |
| 41 | 2-{[2-(Trifluoromethoxy)phenyl]methoxy}-2,3-dihydro-1H-isoindole-1,3-dione | $^1$H NMR (500 MHz, CDCl$_3$) δ ppm 7.85-7.78 (m, 2H), 7.78-7.70 (m, 3H), 7.42 (td, J = 8.0, 1.7 Hz, 1H), 7.34 (td, J = 7.5, 0.9 Hz, 1H), 7.32-7.24 (m, 1H), 5.31 (s, 2H). |
| 48, 95 | 4-{[(1,3-Dioxo-2,3-dihydro-1H-isoindol-2-yl)oxy]methyl}-N,N-bis(2-methoxyethyl)benzamide | Synthesized from 4-(chloromethyl)-N,N-bis(2-methoxyethyl)benzamide ($^1$H NMR (500 MHz, CHLOROFORM-d) δ ppm 7.43 (4 H, s), 4.61 (2H, s), 3.15-3.88 (14H, m)) $^1$H NMR (500 MHz, CHLOROFORM-d) δ ppm 7.80-7.87 (2H, m), 7.71-7.79 (2H, m), 7.59 (2H, d, J = 8.0 Hz), 7.39-7.48 (2H, m), 5.24 (2H, s), 3.18-3.86 (14H, m) |
| 51 | 2-[(2-Phenylpropan-2-yl)oxy]-2,3-dihydro-1H-isoindole-1,3-dione | $^1$H NMR (500 MHz, CHLOROFORM-d) δ ppm 7.83 (2H, dd, J = 5.4, 3.1 Hz), 7.65-7.79 (4H, m), 7.37-7.43 (2H, m), 7.31-7.37 (1 H, m), 1.80 (6H, s) |

TABLE 4-continued

| Example No. | Name | ¹H NMR |
|---|---|---|
| 54 | 2-[(3,5-dibromo-2-hydroxyphenyl)methoxy]-2,3-dihydro-1H-isoindole-1,3-dione | ¹H NMR (500 MHz, DMSO-d6) δ ppm 9.81 (1H, s), 7.86 (4H, s), 7.75 (1H, d, 2.4 Hz), 7.62 (1H, d, 2.5 Hz), 5.22 (2H, s) |
| 61 | 2-{[4-(1H-pyrazol-1-yl)phenyl]methoxy}-2,3-dihydro-1H-isoindole-1,3-dione | ¹H NMR (500 MHz, DMSO-d6) δ ppm 8.53 (1H, d, J = 2.4 Hz), 7.88 (2H, d, J = 8.5 Hz), 7.83 (4H, s), 7.76 (1H, d, J = 1.6 Hz), 7.63 (2H, d, J = 8.5 Hz), 6.56 (1H, t, J = 2.0 Hz), 5.19 (2H, s) |
| 82 | N-(4-{[(1,3-dioxo-2,3-dihydro-1H-isoindol-2-yl)oxy]methyl}phenyl)acetamide | ¹H NMR (400 MHz, DMSO-d6): δ ppm 10.01 (1H, s), 7.83 (4H, m), 7.57 (2H, dd, 2.6, 9.5 Hz), 7.39 (2H, dd, 2.1, 9.0 Hz), 5.07 (2H, s), 2.02 (3H, s). |
| 67 | 2-{[5-(trifluoromethyl)furan-2-yl]methoxy}-2,3-dihydro-1H-isoindole-1,3-dione | ¹H NMR (CDCl₃, 500 MHz) δ ppm 7.87-7.80 (2H, m), 7.79-7.72 (2H, m), 6.77 (1H, dd, J = 3.3, 0.9 Hz), 6.61 (1H, d, J = 3.3 Hz), 5.18 (2H, s) |

TABLE 5

| No. | ¹H NMR | % Purity | LC-MS (min) | Mass ion observed | Mass |
|---|---|---|---|---|---|
| 3 | ¹H NMR (500 MHz, DMSO-d6) d ppm 9.97 (1H, s), 8.15-8.34 (2H, m), 7.93-8.08 (2H, m), 7.38 (2H, d, 8.5 Hz), 6.99-7.20 (2H, m), 4.94 (2H, s), 3.48 (3H, s), 2.26 (3H, s) | 100 | 1.97 | [M + Na]⁺ | 422 |
| 4 | ¹H NMR (500 MHz, DMSO-d6) d ppm 9.76 (1H, br. s.), 9.56 (1H, s), 8.16-8.32 (2H, m), 7.93-8.06 (2H, m), 7.13 (2H, d, 8.5 Hz), 6.71 (2H, d, 8.5 Hz), 4.80 (2H, s), 3.48 (3H, s) | 96 | 1.96 | [M + Na]⁺ | 379 |
| 5 | ¹H NMR (500 MHz, DMSO-d6) 10.07 (1H, s), 8.21-8.33 (1H, m), 8.11-8.20 (1H, m), 7.96-8.09 (2H, m), 4.73 (2H, s), 3.46 (3H, s), 2.15 (3H, s) | 100 | 1.74 | [M − H]⁻ | 362 |
| 6 | ¹H NMR (500 MHz, CHLOROFORM-d) d ppm 8.93 (1H, s), 8.27-8.44 (2H, m), 7.74-7.97 (2H, m), 4.14-4.33 (4H, m), 3.43 (3H, s), 1.18 (9H, s) | 100 | 2.03 | [M + H]⁺ | 380 |
| 10 | ¹H NMR (500 MHz, CHLOROFORM-d) d ppm 8.91 (1H, s), 8.37-8.43 (1H, m), 8.29-8.35 (1H, m), 7.82-7.90 (2H, m), 7.37 (2H, dt, J = 7.4, 1.8 Hz), 7.21-7.30 (2H, m), 5.16 (2H, s), 3.42 (3H, s) | 99 | 2.1 | [M + Na]⁺ | 398 |
| 11 | ¹H NMR (500 MHz, CHLOROFORM-d) d ppm 8.90 (1H, s), 8.36-8.41 (1H, m), 8.30-8.36 (1H, m), 7.88 (2H, dd, 5.7, 3.5 Hz), 7.25-7.33 (3H, m), 7.20 (1H, d, 7.1 Hz), 4.98 (2H, s), 3.42 (3H, s) | 100 | 2.13 | [M + H]⁺ | 376 |
| 12 | ¹H NMR (500 MHz, CHLOROFORM-d) d ppm 8.87 (1H, s), 8.27-8.41 (2H, m), 7.81-7.92 (2H, m), 7.29-7.34 (2H, m), 7.24-7.28 (2H, m), 4.97 (2H, s), 3.42 (3H, s) | 100 | 2.13 | [M + H]⁺ | 376 |
| 14 | ¹H NMR (500 MHz, CHLOROFORM-d) d ppm 8.86 (1H, s), 8.19-8.50 (2H, m), 7.70-7.93 (2H, m), 7.22 (1H, d, J = 7.9 Hz), 7.09-7.16 (3H, m), 4.98 (2H, s), 3.42 (3H, s), 2.34 (3H, s) | 100 | 2.11 | [M + H]⁺ | 356 |
| 15 | ¹H NMR (500 MHz, CHLOROFORM-d) d ppm 9.00 (1H, s), 8.55-8.61 (1H, m), 8.37-8.43 (1H, m), 8.30-8.37 (1H, m), 7.83-7.91 (2H, m), 7.69 (1H, d, J = 1.7 Hz), 7.33 (1H, d, J = 7.9 Hz), 7.19-7.26 (1H, m), 5.14 (2H, s), 3.42 (3H, s) | 98 | 1.44 | [M + H]⁺ | 343 |
| 16 | ¹H NMR (500 MHz, CHLOROFORM-d) d ppm 8.92 (1H, s), 8.56-8.60 (2H, m), 8.35-8.39 (1H, m), 8.30-8.35 (1H, m), 7.82-7.91 (2H, m), 7.66 (1H, d, J = 7.7 Hz), 7.27-7.30 (1H, m), 5.04 (2H, s), 3.42 (3H, s) | 98 | 1.22 | [M + H]⁺ | 343 |
| 20 | ¹H NMR (500 MHz, DMSO-d6) d ppm 10.07 (1H, br. s.), 8.25 (2H, ddd, 17.7, 5.6, 3.5 Hz), 8.03 (2H, dd, 5.6, 3.4 Hz), 7.73 (2H, d, 8.1 Hz), 7.62 (2H, d, 8.1 Hz), 5.07 (2H, s), 3.56-3.69 (4H, m), 3.48 (3H, s), 2.76-2.90 (4H, m). | 100 | 1.89 | [M + H]⁺ | 491 |

TABLE 5-continued

| No. | ¹H NMR | % Purity | LC-MS (min) | Mass ion observed | Mass |
|---|---|---|---|---|---|
| 21 | ¹H NMR (500 MHz, CHLOROFORM-d) d ppm 8.97 (1H, s), 8.36-8.41 (1H, m), 8.30-8.36 (1H, m), 7.83-7.91 (2H, m), 7.66 (1H, d, J = 7.9 Hz), 7.50-7.57 (2H, m), 7.43 (1H, s), 5.22 (2H, s), 3.42 (3H, s) | 95 | 2.13 | [M + H]⁺ | 410 |
| 22 | ¹H NMR (250 MHz, CHLOROFORM-d) d ppm 8.89 (1H, s), 8.28-8.42 (2H, m), 7.81-7.93 (2H, m), 7.31-7.41 (2H, m), 7.19 (2H, d, J = 7.9 Hz), 5.01 (2H, s), 3.42 (3H, s) | 100 | 2.2 | [M + H]⁺ | 426 |
| 24 | ¹H NMR (500 MHz, CHLOROFORM-d) d ppm 8.81 (1H, s), 8.31 (1H, dd, J = 7.7, 1.1 Hz), 8.03 (1H, dd, J = 7.9, 1.1 Hz), 7.80-7.86 (1H, m), 7.70-7.78 (1H, m), 7.20-7.31 (3 H, m), 7.15 (2H, d, J = 6.9 Hz), 4.27 (2H, t, J = 6.9 Hz), 3.42 (3H, s), 2.88 (2H, t, J = 6.9 Hz) | 92 | 2.06 | [M + H]⁺ | 356 |
| 25 | ¹H NMR (500 MHz, CHLOROFORM-d) d ppm 8.61 (1H, s), 8.31-8.38 (2H, m), 7.80-7.91 (2H, m), 7.28-7.37 (5H, m), 5.19 (1H, d, J = 6.6 Hz), 3.40 (3H, s), 1.46 (3H, d, J = 6.6 Hz) | 100 | 2.08 | [M + Na]⁺ | 378 |
| 26 | ¹H NMR (500 MHz, CHLOROFORM-d) d ppm 8.50 (1H, t, J = 1.6 Hz), 8.14-8.27 (2H, m), 7.78 (1H, t, J = 7.9 Hz), 7.31-7.39 (2H, m), 7.13 (1H, s), 7.02-7.10 (2H, m), 4.99 (2 H, s), 3.07 (3H, s) | 99 | 1.83 | [M − H]⁻ | 358 |
| 27 | ¹H NMR (500 MHz, DMSO-d6) d ppm 10.87 (1H, s) 8.23-8.39 (2H, m) 8.14 (1H, d, J = 7.9 Hz) 7.88-7.99 (1H, m) 4.72 (2H, s) 2.15 (3H, s) | 100 | 1.54 | [M + H]⁺ | 364 |
| 28 | ¹H NMR (500 MHz, CHLOROFORM-d) d ppm 8.50 (1H, t, J = 1.6 Hz), 8.20 (2H, dt, J = 7.8, 2.0 Hz), 7.77 (1H, t, J = 7.9 Hz), 7.32-7.47 (5H, m), 7.19 (1H, s), 5.03 (2H, s), 3.03 (3H, s) | 100 | 1.79 | [M + Na]⁺ | 364 |
| 29 | ¹H NMR (500 MHz, CHLOROFORM-d) d ppm 7.72 (1H, d, J = 7.9 Hz), 7.60 (1H, d, J = 0.8 Hz), 7.54-7.58 (1H, m), 7.51 (1H, td, J = 7.8, 1.3 Hz), 7.31-7.40 (4H, m), 7.00-7.06 (2H, m), 4.99 (2H, s), 19F NMR (235 MHz, CHLOROFORM-d) d ppm −112.54 | 96 | 2.02 | [M − H]⁻ | 320 |
| 30 | ¹H NMR (500 MHz, CHLOROFORM-d) d ppm 7.75 (1H, d, J = 7.9 Hz), 7.63 (1H, d, J = 0.6 Hz), 7.57-7.61 (1H, m), 7.51-7.57 (1 H, m), 7.49 (1H, s), 7.37-7.42 (1H, m), 4.75 (2H, s), 2.22 (3H, s) | 96 | 1.92 | [M + Na]⁺ | 348 |
| 32 | ¹H NMR (500 MHz, CDCl3) d 8.92 (s, 1H), 8.40-8.26 (m, 2H), 7.91-7.81 (m, 2H), 7.36 (t, J = 8.1 Hz, 1H), 7.24 (d, J = 7.6 Hz, 1H), 7.17 (d, J = 7.6 Hz, 2H), 5.02 (s, 2H), 3.41 (s, 3H). | 100 | 2.17 | [M + Na]⁺ | 448 |
| 33 | ¹H NMR (500 MHz, CDCl3) d 8.93 (s, 1H), 8.40-8.30 (m, 2H), 7.90-7.78 (m, 2H), 7.62-7.55 (m, 2H), 7.53-7.42 (m, 2H), 5.06 (s, 2H), 3.41 (s, 3H). | 100 | 2.13 | [M + Na]⁺ | 432 |
| 34 | ¹H NMR (500 MHz, CDCl3) d 8.82 (s, 1H), 8.40-8.28 (m, 2H), 7.89-7.81 (m, 2H), 6.80 (dd, J = 6.0, 1.6 Hz, 2H), 6.78-6.73 (m, 1H), 5.95 (s, 2H), 4.89 (s, 2H), 3.40 (s, 3H). | 97 | 2.05 | [M + Na]⁺ | 408 |
| 35 | ¹H NMR (500 MHz, CDCl3) d 8.94 (s, 1H), 8.40-8.31 (m, 2H), 7.92 (d, J = 8.3 Hz, 2H), 7.90-7.85 (m, 2H), 7.51 (d, J = 8.3 Hz, 2H), 5.08 (s, 2H), 3.41 (s, 3H), 3.05 (s, 3H). | 97 | 1.84 | [M + Na]⁺ | 442 |
| 36 | ¹H NMR (500 MHz, CDCl3) d 8.92 (s, 1H), 8.39-8.27 (m, 2H), 7.91-7.75 (m, 2H), 7.26-7.19 (m, 2H), 7.19-7.09 (m, 2H), 5.06 (s, 2H), 3.41 (s, 3H), 2.36 (s, 3H). | 100 | 2.05 | [M + Na]⁺ | 378 |
| 38 | ¹H NMR (400 MHz, DMSO-d6) d ppm 10.73 (1H, s), 8.33 (1H, t, 1.5 Hz), 8.28 (1H, d, 7.8 Hz), 8.18 (1H, d, 7.8 Hz), 7.93 (1H, t, 7.8 Hz), 7.35-7.43 (4H, m), 4.90 (2H, s), 3.30 (3H, s) | 100 | 2.84 | [M + Na]⁺ | 397 |

TABLE 5-continued

| No. | $^1$H NMR | % Purity | LC-MS (min) | Mass ion observed | Mass |
|---|---|---|---|---|---|
| 39 | $^1$H NMR (400 MHz, DMSO-d6) d ppm 10.65 (1H, s), 8.32 (1H, t, 1.5 Hz), 8.26 (1H, d, 7.8 Hz), 8.17 (1H, d, 7.8 Hz), 7.91 (1H, t, 7.8 Hz), 7.26 (2H, d, 8.6 Hz), 6.90 (2H, d, 8.6 Hz), 4.83 (2H, s), 3.73 (3H, s), 3.29 (3H, s) | 94 | 2.67 | [M − H]$^-$ | 370 |
| 40 | $^1$H NMR (500 MHz, CHLOROFORM-d) d ppm 8.91 (1H, s), 8.36-8.41 (1H, m), 8.31-8.36 (1H, m), 7.81-7.93 (2H, m), 7.28-7.34 (1H, m), 7.10 (1H, d, J = 7.6 Hz), 6.99-7.05 (2H, m), 5.00 (2H, s), 3.42 (3H, s) | 97 | 2.1 | [M + Na]$^+$ | 382 |
| 41 | $^1$H NMR (500 MHz, CHLOROFORM-d) d ppm 8.91 (1H, s), 8.36-8.42 (1H, m), 8.29-8.35 (1H, m), 7.83-7.90 (2H, m), 7.40-7.45 (1H, m), 7.34-7.40 (1H, m), 7.23-7.30 (2H, m), 5.11 (2H, s), 3.42 (3H, s) | 100 | 2.24 | [M + Na]$^+$ | 448 |
| 45 | $^1$H NMR (300 MHz, DMSO-d6) d ppm 11.19 (1H, s), 7.83 (1H, d, 7.8 Hz), 7.80 (1H, m), 7.75 (1H, d, 8.4 Hz), 7.57 (1H, ddd, 7.7, 7.2, 1.0 Hz), 7.43-7.34 (5H, m), 4.90 (2H, s). | 100 | 3.22 | [M − H]$^-$ | 336 |
| 46 | $^1$H NMR (400 MHz, DMSO-d6) d ppm 11.13 (1H, s), 7.82-7.88 (1H, m), 7.79 (1H, d, 0.8 Hz), 7.75 (1H, dd, 8.5, 0.8 Hz), 7.56 (1H, ddd, 8.5, 7.3, 1.3 Hz), 7.37-7.46 (1H, m), 7.23-7.32 (2H, m), 6.87-6.95 (2H, m), 4.84 (2H, s) | 100 | 3.03 | [M − H]$^-$ | 332 |
| 47 | $^1$H NMR (400 MHz, DMSO-d6) d ppm 11.27 (1H, s), 7.84 (1H, d, 7.8 Hz), 7.80 (1H, d, 0.8 Hz), 7.75 (1H, d, 8.4 Hz), 7.56 (1H, ddd, 8.4, 7.2, 1.2 Hz), 7.41-7.47 (3H, m), 7.33-7.36 (2H, m), 5.02 (2H, s) | 99 | 3.19 | [M + H]$^+$ | 338 |
| 48 | $^1$H NMR (500 MHz, CHLOROFORM-d) d ppm 8.89 (1H, s), 8.35-8.39 (1H, m), 8.31-8.35 (1H, m), 7.84-7.89 (2H, m), 7.38-7.41 (2H, m), 7.33-7.35 (2H, m), 5.02 (2H, s), 3.61-3.83 (4H, m), 3.21-3.55 (13H, m) | 99 | 1.87 | [M + H]$^+$ | 501 |
| 49 | $^1$H NMR (500 MHz, CHLOROFORM-d) d ppm 8.86 (1H, s), 8.37-8.42 (1H, m), 8.29-8.34 (1H, m), 7.81-7.89 (2H, m), 7.29-7.38 (2H, m), 7.12 (1H, td, J = 7.5, 0.9 Hz), 7.05 (1H, t, J = 9.1 Hz), 5.09 (2H, s), 3.42 (3H, s) | 98 | 2.12 | [M + Na]$^+$ | 382 |
| 51 | $^1$H NMR (500 MHz, CHLOROFORM-d) d ppm 8.44 (1H, s), 8.33-8.40 (2H, m), 7.83-7.91 (2H, m), 7.31-7.35 (4H, m), 7.23-7.27 (1H, m), 3.41 (3H, s), 1.62 (6H, s) | 100 | 2.24 | [M + Na]$^+$ | 392 |
| 54 | $^1$H NMR (500 MHz, DMSO-d6) d ppm 9.96 (1H, br. s.), 9.73 (1H, br. s.), 8.23-8.31 (1H, m), 8.16-8.23 (1H, m), 7.94-8.09 (2H, m), 7.71 (1H, d, J = 2.5 Hz), 7.38 (1H, d, J = 2.4 Hz), 4.97 (2H, s), 3.47 (3H, s) | 99 | 2.27 | [M + Na]$^+$ | 538 |
| 59 | $^1$H NMR (300 MHz, CHLOROFORM-d) d ppm 8.44-8.60 (1H, m), 8.10-8.29 (2H, m), 7.75 (1H, t, 7.8 Hz), 7.37 (2H, d, 1.8 Hz), 7.07 (1H, s), 6.83-7.02 (2H, m), 5.11 (2H, s), 3.86 (3H, s), 3.00 (3H, s) | 97 | 2.17 | [M + Na]$^+$ | 394 |
| 60 | $^1$H NMR (400 MHz, DMSO-d6) d ppm 11.30 (1H, s), 8.52 (1H, m), 7.75-7.85 (4H, m), 7.57 (1H, ddd, 1.3, 7.2, 7.8 Hz), 7.40-7.44 (2H, m), 7.30-7.34 (1H, m), 4.99 (2H, s) | 97 | 1.38 | [M + H]$^+$ | 305 |
| 61 | $^1$H NMR (500 MHz, DMSO-d6) d ppm 10.75 (1H, s), 8.51 (1H, d, 2.4 Hz), 8.36 (1H, s), 8.29 (1H, d, 7.9 Hz), 8.21 (1H, d, 7.9 Hz), 7.95 (1H, t, 7.9 Hz), 7.84 (2H, d, 8.5 Hz), 7.75 (1H, d, 1.1 Hz), 7.47 (2H, d, 8.5 Hz), 6.55 (1H, t, 2.0 Hz), 4.96 (2H, s), 3.31 (3H, s) | 98 | 1.83 | [M + H]$^+$ | 408 |
| 62 | $^1$H NMR (400 MHz, DMSO-d6) d ppm 10.85 (1H, s), 8.50-8.60 (1H, m), 8.37 (1H, t, 1.6 Hz), 8.28-8.34 (1H, m), 8.18-8.27 (1H, m), 7.96 (1H, t, 7.9 Hz), 7.82 (1H, td, 7.7, 1.8 Hz), 7.40 (1H, d, 7.8 Hz), 7.35 (1H, ddd, 7.7, 4.9, 1.0 Hz), 5.01 (2H, s), 3.33 (3H, s) | 100 | 1.73 | [M − H]$^-$ | 341 |
| 63 | $^1$H NMR (400 MHz, DMSO-d6) d ppm 10.72 (1H, s), 8.36 (1H, t, 1.6 Hz), 8.26-8.32 (1H, m), 8.16-8.24 (1H, m), 7.94 (1H, t, 7.9 Hz), 7.19-7.34 (4H, m), 4.88 (2H, s), 3.31 (3H, s), 2.88 (1H, spt, 6.9 Hz), 1.19 (6H, d, 6.9 Hz) | 56 | 3.13 | [M − H]$^-$ | 382 |

TABLE 5-continued

| No. | $^1$H NMR | % Purity | LC-MS (min) | Mass ion observed | Mass |
|---|---|---|---|---|---|
| 64 | $^1$H NMR (300 MHz, DMSO-d6) d ppm 11.15 (1H, s), 7.85 (1H, d, 7.9 Hz), 7.70-7.80 (2H, m), 7.50-7.63 (1H, m), 7.37-7.48 (1H, m), 7.22-7.36 (2H, m), 6.85-7.05 (2H, m), 4.92 (2H, s), 3.33 (3H, s) | 100 | 3.17 | [M − H]$^−$ | 332 |
| 65 | $^1$H NMR (400 MHz, CHLOROFORM-d) d ppm 7.67-7.76 (1H, m), 7.61 (1H, d, J = 1.0 Hz), 7.54-7.59 (1H, m), 7.49-7.54 (1H, m), 7.48 (1H, s), 7.36 (1H, ddd, 8.0, 7.1, 1.0 Hz), 7.17-7.31 (4H, m), 4.99 (2H, s), 2.90 (1H, spt, 6.9 Hz), 1.24 (6H, d, 7.0 Hz) | 100 | 3.5 | [M − H]$^−$ | 344 |
| 66 | $^1$H NMR (400 MHz, CHLOROFORM-d) d ppm 8.50 (1H, t, 1.6 Hz), 8.21 (2H, dd, 8.0, 1.8 Hz), 7.78 (1H, t, 7.9 Hz), 7.28-7.33 (1H, m), 7.11 (1H, s), 6.94 (1H, d, 7.8 Hz), 6.91 (1H, dd, 2.6, 0.9 Hz), 6.86-6.89 (1H, m), 5.00 (2H, s), 3.82 (3H, s), 3.05 (3H, s) | 100 | 2.7 | [M + H]$^+$ | 372 |
| 67 | $^1$H NMR (500 MHz, CDCl3) d 8.48 (t, J = 1.6 Hz, 1H), 8.25-8.20 (m, 2H), 7.80 (t, J = 7.9 Hz, 1H), 7.19 (s, 1H), 6.79-6.75 (m, 1H), 6.56 (d, J = 3.4 Hz, 1H), 5.00 (s, 2H), 3.10 (s, 3H). | 97 | 1.92 | [M − H]$^−$ | 398 |
| 72 | $^1$H NMR (400 MHz, CHLOROFORM-d) d ppm 8.48-8.49 (1H, m), 8.17-8.21 (2H, m), 7.75 (1H, t, 7.8 Hz), 7.37-3.40 (2H, m), 7.27-7.30 (2H, m), 7.09 (1H, s), 4.99 (2H, s), 3.01 (3H, s), 1.31 (9H, s) | 100 | 3.2 | [M − H]$^−$ | 396 |
| 73 | $^1$H NMR (400 MHz, CHLOROFORM-d) d ppm 7.70 (1H, d, 7.8 Hz), 7.60 (1H, d, 0.8 Hz), 7.55 (1H, dd, 8.4 Hz, 0.8 Hz), 7.47-7.51 (1H, m), 7.33-7.37 (2H, m), 7.23-7.27 (2H, m), 4.98 (2H, s), 3.79 (3H, s) | 98 | 3.08 | [M − H]$^−$ | 332 |
| 81 | $^1$H NMR (300 MHz, CHLOROFORM-d) d ppm 8.46 (1H, s), 8.20 (2H, dd, J = 13.0, 7.8 Hz), 7.80 (1H, t, J = 7.9 Hz), 7.36-7.49 (1H, m), 4.82 (2H, s), 3.11 (3H, s), 2.44 (3H, s), 2.24 (3H, s) | 100 | 2.29 | [M + H]$^+$ | 361 |
| 82 | $^1$H NMR (300 MHz, DMSO-d6) d ppm 10.67 (1H, s), 9.97 (1H, s), 8.33 (1H, m), 8.26 (1H, d, 7.9 Hz), 8.18 (1H, d, 8.2 Hz), 7.92 (1H, t, 7.8 Hz), 7.53 (2H, d, 8.4 Hz), 7.24 (2H, d, 8.4 Hz), 4.83 (2H, s), 3.29 (3H, s), 2.02 (3H, s) | 100 | 2.22 | [M + H]$^+$ | 399 |
| 83 | $^1$H NMR (300 MHz, CHLOROFORM-d) d ppm 7.72 (1H, d, 8.0 Hz), 7.55-7.57 (2H, m), 7.51 (1H, dt, 1.2, 6.8, 7.7 Hz), 7.37 (1H, dt, 1.2, 6.8, 7.7 Hz), 7.32 (1H, s), 4.81 (2H, s), 2.41 (3H, s), 2.26 (3H, s) | 100 | 2.75 | [M + H]$^+$ | 323 |
| 84 | $^1$H NMR (500 MHz, DMSO-d6) d ppm 10.93 (1H, s), 8.37 (1H, t, 1.6 Hz), 8.31 (1H, dt, 7.9, 1.3 Hz), 8.21-8.27 (1H, m), 8.06 (1H, dd, 9.2, 0.7 Hz), 7.93-8.00 (2H, m), 5.09 (2H, s), 3.31 (3H, s) | 100 | 1.81 | [M − H]$^−$ | 382 |
| 95 | $^1$H NMR (CDCl3, 500 MHz) d 8.50 (1H, t, J = 1.5 Hz), 8.25-8.16 (2H, m), 7.85-7.75 (3H, m), 7.46 (2H, d, J = 8.3 Hz), 7.29 (1H, s), 5.08 (2H, s), 3.52 (4H, t, J = 5.8 Hz), 3.39 (4H, t, J = 5.8 Hz), 3.28 (6H, s), 3.09 (3H, s) | 100 | 1.91 | [M + H]$^+$ | 537 |

General Method 4

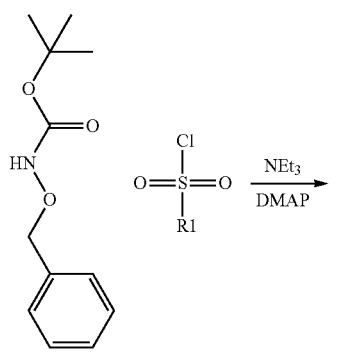

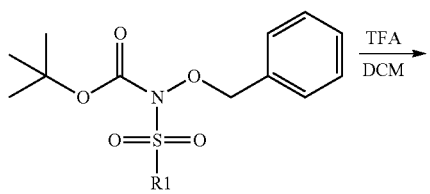

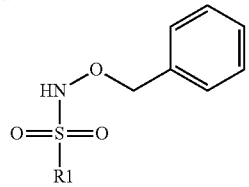

To a solution of tert-butyl N-(benzyloxy)carbamate (1 equiv.) in DCM (20 vol.) was added triethylamine (1 equiv.) and the reaction mixture was stirred at room temperature for 10 minutes. To this solution was added the sulfonyl chloride (1 equiv.) and dimethylaminopyridine (0.1 equiv.) and stirring was continued until complete consumption of the starting material was observed by LCMS. The reaction was quenched by addition of water (5 vol.) and the organics extracted into DCM (10 vol.), dried over sodium sulfate, filtered and concentrated in vacuo. The crude product was purified by silica gel chromatography eluting with heptane:ethyl acetate (10%-60% gradient).

To a solution of the BOC protected sulfonamide (1 equiv.) in DCM (10 vol.) was added TFA (20-40% solution in DCM) and stirring was continued until complete consumption of the starting material was observed by LC-MS. The reaction mixture was concentrated in vacuo and purified by silica gel chromatography eluting with heptane:ethyl acetate (10%-60% gradient).

Table 6 provides compounds of the disclosure synthesized according to General Method 4.

TABLE 6

| No. | $^1$H NMR | % Purity | LC-MS (min) | Mass ion observed | Mass |
|---|---|---|---|---|---|
| 1 | $^1$H NMR (500 MHz, CHLOROFORM-d) d ppm 8.87 (1H, s), 8.36-8.41 (1H, m), 8.28-8.35 (1H, m), 7.81-7.90 (2H, m), 7.29-7.38 (5H, m), 5.02 (2H, s) | 95 | 2.05 | $[M + H]^+$ | 342 |
| 23 | $^1$H NMR (500 MHz, CHLOROFORM-d) d ppm 7.72 (1H, d, J = 7.9 Hz), 7.60-7.63 (1H, m), 7.54-7.58 (1H, m), 7.50 (1H, td, J = 7.8, 1.1 Hz), 7.31-7.40 (7H, m), 5.03 (2H, s) | 94 | 2.18 | $[M + Na]^+$ | 326 |

The compounds in Table 7 were synthesized from the corresponding pyridine analogue via the following method.

The pyridine analogue synthesized using General method 1, 2, or 3 was heated to 65° C. in 40% peracetic acid until complete consumption of the starting material was observed by LC-MS. The peracetic acid was removed in vacuo and the crude product was taken up in DCM and neutralized with sodium bicarbonate solution. The organics were washed with brine and dried over sodium sulfate, filtered and concentrated in vacuo. The desired product was isolated by trituration from heptane:ethyl acetate mixtures to give the desired pyridine N-oxide

TABLE 7

| No. | $^1$H NMR | % Purity | LC-MS (min) | Mass ion observed | Mass |
|---|---|---|---|---|---|
| 78 | $^1$H NMR (500 MHz, DMSO-d6) d ppm 10.65 (1H, s), 8.49 (1H, d, 6.5 Hz), 8.15 (1H, dd, 8.0, 1.7 Hz), 7.75 (1H, td, 7.1, 2.0 Hz), 7.56-7.64 (1H, m), 7.26-7.38 (5H, m), 4.89 (2H, s) | 100 | 1.87 | $[M + H]^+$ | 281 |
| 92 | $^1$H NMR (CDCl3, 500 MHz) d 8.75 (1H, s), 8.31 (2H, d, J = 6.9 Hz), 7.82 (1H, d, J = 8.0 Hz), 7.43 (1H, dd, J = 7.8, 6.7 Hz), 7.40-7.31 (5H, m), 5.02 (2H, s) | 100 | 1.52 | $[M + H]^+$ | 281 |

TABLE 7-continued

| No. | $^1$H NMR | % Purity | LC-MS (min) | Mass ion observed | Mass |
|---|---|---|---|---|---|
| 93 | $^1$H NMR (DMSO, 500 MHz) d 10.93 (1H, s), 8.51 (1H, dt, J = 5.8, 1.5 Hz), 8.46 (1H, s), 7.73-7.64 (2H, m), 3.71 (3H, s) | 99 | 0.83 | [M + H]$^+$ | 205 |

Synthesis of Example 37

To a solution of O-(oxan-2-yl)hydroxylamine (1.01 g, 8.64 mmol) in water (3 mL) cooled to 0° C. was added a solution of potassium carbonate (1.19 g, 8.64 mmol) in water (1 mL) maintaining a temperature <10° C. To this solution was added a solution of 2-methanesulfonylbenzene-1-sulfonyl chloride (1.1 g, 4.32 mmol) in THF; methanol (8 mL: 2 mL) and the reaction mixture was allowed to warm to room temperature over 1 hour. The reaction mixture was diluted with diethyl ether (20 ml) and waster (5 mL) and the organics dried over sodium sulfate, filtered and concentrated in vacuo. The resulting solid was triturated with diethyl ether to yield the desired compound as a white solid (1.15 g, 75% yield). LC-MS tR=1.84 min, [M+Na]$^+$=358, $^1$H NMR (500 MHz, CHLOROFORM-d) δ ppm 8.86 (1H, s), 8.28-8.42 (2H, m), 7.80-7.96 (2H, m), 5.19 (1H, t, 3.4 Hz), 3.76-3.87 (1H, m), 3.59-3.67 (1H, m), 3.44 (3H, s), 1.66-1.78 (1H, m), 1.44-1.65 (5H, m)

Synthesis of Example 55

5-[(Benzyloxy)sulfamoyl]-4-chloro-2-fluorobenzoic acid was synthesized from 4-chloro-5-(chlorosulfonyl)-2-fluorobenzoic acid according to General Method 2 and was purified by silica gel chromatography eluting with heptane:ethyl acetate (20-60%) to yield the desired compound as a white solid (1.2 g, 32% yield). $^1$H NMR (500 MHz, CHLOROFORM-d) δ ppm 8.86 (1H, d, J=7.3 Hz), 8.79 (1H, d, J=4.7 Hz), 7.96 (1H, s), 7.55 (1H, dd, J=7.6, 6.0 Hz), 7.33 (5H, s), 4.98 (2H, s)

To a solution of 5-[(benzyloxy)sulfamoyl]-4-chloro-2-fluorobenzoic acid (100 mg, 0.29 mmol) in DMF (1 mL) was added furfurylamine (131.14 µl, 1.47 mmol). The reaction mixture was heated to 95° C. for 2 hours after which time the reaction mixture was poured into water (2 mL) and acidified to pH 4 with glacial acetic acid and the product was purified by reverse phase neutral HPLC (43 mg, 33% yield). LC-MS tR=2.04 min, [M−H]$^−$=435, $^1$H NMR (500 MHz, DMSO-d6) δ ppm 10.33 (1H, s), 8.82 (1H, br. s.), 8.45 (1H, s), 7.61 (1H, s), 7.23-7.38 (5H, m), 7.07 (1H, s), 6.39 (2H, d, J=16.6 Hz), 4.82 (2H, s), 4.59 (2H, d, J=5.4 Hz).

Synthesis of Example 56

N-(benzyloxy)-5-[(benzyloxy)sulfamoyl]-4-chloro-2-fluorobenzamide was synthesized from 4-chloro-5-(chlorosulfonyl)-2-fluorobenzoic acid according to General Method 2 and was purified by silica gel chromatography eluting with heptane:ethyl acetate (20-60%) to yield the desired compound as a white solid (1.7 g, 21% yield). $^1$H NMR (500 MHz, CHLOROFORM-d) δ ppm 8.84-8.94 (1H, m), 7.59 (1H, s), 7.29-7.50 (11H, m), 5.08 (2H, br. s.), 4.99 (2H, s)

To a solution of N-(benzyloxy)-5-[(benzyloxy)sulfamoyl]-4-chloro-2-fluorobenzamide (365 mg, 0.79 mmol) in DMF (1 mL) was added furfurylamine (349.76 µl, 3.93 mmol). The reaction mixture was heated to 95° C. for 2 hours after which time the reaction mixture was poured into water (2 mL) and acidified to pH 4 with glacial acetic acid and the product was purified by reverse phase neutral HPLC (80 mg, 19% yield). LC-MS tR=2.30 min, [M+H]$^+$=542, $^1$H NMR (500 MHz, DMSO-d6) δ ppm 10.19 (1H, br. s.), 8.45 (1H, br. s.), 8.05 (1H, br. s.), 7.62 (1H, s), 7.19-7.50 (11H, m), 6.99 (1H, s), 6.42 (1H, dd, J=3.2, 1.9 Hz), 6.35 (1H, d, J=2.4 Hz), 4.93 (2H, br. s.), 4.80 (2H, s), 4.51 (2H, d, J=5.2 Hz).

Synthesis of Example 96

To solution of [(tert-butoxy)carbonyl]amino pyrazine-2-carboxylate (1 g, 4.18 mmol) in DCM (20 mL) was added triethylamine (582.63 µl, 4.18 mmol) and the reaction mixture was stirred at room temperature for 3 hours, after which time 2-methanesulfonylbenzene-1-sulfonyl chloride (1.06 g, 4.18 mmol) and dimethylaminopyridine (0.05 g, 0.42 mmol) were added and stirring continued for 1 hour. The reaction mixture was quenched by the addition of water (10 mL) and the organics separated. The aqueous was re-extracted with DCM (10 mL) and combined, dried over sodium sulfate, filtered and concentrated in vacuo. The resulting solid was washed with diethyl ether and pentane and dried in vacuo to yield the title compound as an off white solid (1.0 g, 52% yield). LC-MS $t_R$=2.72 min, [M+H]$^+$=458, $^1$H NMR (500 MHz, DMSO-d6) δ 9.06 (s, 1H), 8.96 (d, J=1.5 Hz, 1H), 8.95 (d, J=1.5 Hz, 1H), 8.36-8.30 (m, 2H), 8.14-8.11 (m, 2H), 3.47 (s, 3H), 1.30 (s, 9H).

2-Methanesulfonylbenzenesulfonamido pyrazine-2-carboxylate

N-[(tert-butoxy)carbonyl](2-methanesulfonylbenzene)sulfonamido pyrazine-2-carboxylate (0.4 g, 0.87 mmol) in was taken up in 4N HCl in 1,4-dioxane (1.54 g, 17.49 mmol) and the resulting reaction mixture was stirred for 2 days at room temperature. A solid precipitated from the solution and was collected by filtration under argon, washed with diethyl ether and dried in vacuo, (0.12 g, 38% yield). LC-MS $t_R$=0.49 min, [M+H]$^+$=358, $^1$H NMR (400 MHz, DMSO) δ 11.11 (s, 1H), 9.09 (d, 1.4 Hz, 1H), 8.93 (d, 2.4 Hz, 1H), 8.80 (dd, 2.4, 1.5 Hz, 1H), 8.28 (ddd, 16.0, 7.7, 1.5 Hz, 2H), 8.11-7.98 (m, 2H), 3.47 (s, 3H).

4.2 Nitroxyl Production from Compound s of the Disclosure as Determined Via $N_2O$ Quantification in the Headspace Protocol Nitrous oxide ($N_2O$) is produced via the dimerization and dehydration of HNO, and is the most common marker for nitroxyl production (Fukuto et al., *Chem. Res. Toxicol.* 18:790-801 (2005)). Nitroxyl, however, can also be partially quenched by oxygen to provide a product that does not produce $N_2O$ (see Mincione et al., *J. Enzyme Inhibition* 13:267-284 (1998); and Scozzafava et al., *J. Med. Chem.* 43:3677-3687 (2000)). Using either nitrous oxide gas or Angeli's salt ("AS") as a standard, the relative amounts of $N_2O$ released from compounds of the disclosure is examined via gas chromatography ("GC") headspace analysis.

A procedure for determining the relative amounts of $N_2O$ released from compounds of the disclosure is as follows. GC is performed on an Agilent gas chromatograph equipped with a split injector (10:1 splitting), microelectron capture detector, and a HP-MOLSIV 30 m×0.32 mm×25 μm molecular sieve capillary column. Helium is used as the carrier (4 mL/min) gas and nitrogen is used as the make-up (20 mL/min) gas. The injector oven and the detector oven are kept at 200° C. and 325° C., respectively. All nitrous oxide analyses are performed with the column oven held at a constant temperature of 200° C.

All gas injections are made using an automated headspace analyzer. Vial pressurization is 15 psi. The analyzer's sample oven, sampling valve, and transfer line are kept at 40° C., 45° C., and 50° C., respectively. The oven stabilization, vial pressurization, loop fill, loop equilibration, and sample injection times are 1.00 min., 0.20 min., 0.20 min., 0.05 min., and 1.00 min., respectively.

All determinations use a batch of nominal 20 mL headspace vials with volumes pre-measured for sample uniformity (actual vial volume varied by ≤2.0% relative standard deviation (n=6)). The average vial volume for the batch is determined from six randomly-selected vials by calculating the weight difference between the capped and sealed empty (i.e., air-filled) vial and the capped and sealed deionized water-filled vial using the known density of deionized water, then averaging. Blanks are prepared by sealing and capping 2 vials then purging each for 20 seconds with a gentle argon stream. Nitroxyl standards are prepared by sealing and capping four vials then purging each for 1 minute with a gentle stream, from a gas cylinder, of a 3000 ppm nitroxyl standard.

"Standards" are prepared by, in duplicate, accurately weighing 10±0.5 mg of a compound of formula (I), (II), or (III) or a compound from Table 1 and adding it to each 4 mL vial. Using an auto pipette, 1 mL of argon-purged anhydrous DMF (Sigma-Aldrich) is added to each 4 mL vial to form a stock solution for each sample and the vials are capped and shaken and/or sonicated to insure complete dissolution upon visual observation. Using an auto pipette, 20 mL vials are charged with 5 mL of PBS (purged for at least 30 min. with argon prior to use), purged with argon for at least 20 sec., and sealed with a rubber septum. Using a 50 μL syringe, 50 μL of the stock solution is injected into each 20 mL vial containing the PBS.

Samples are prepared as follows. In duplicate, 18±1 mg of each sample is accurately weighed into each 4 mL vial. Using an auto pipette, 1 mL of argon-purged anhydrous DMF is added to each 4 mL vial to form a sample stock solution for each sample and the vials are capped and shaken and/or sonicated to insure complete sample dissolution upon visual observation. Using an auto pipette, 20 mL vials are charged with 5 mL of PBS (purged for at least 30 min. with argon prior to use), purged with argon for at least 20 sec., and sealed with a rubber septum. The vials are equilibrated for at least 10 min. at 37° C. in a dry block heater. Thereafter, using a 50 μL syringe, 50 μL of a sample stock solution is injected into each 20 mL vial containing the PBS. The vials are then held at 37° C. in the dry block heater for a time period such that the sum of the time spent in the dry block heater plus the time spent in the automated headspace analyzer oven before sample injection equals the desired incubation time.

Another procedure for determining the relative amounts of $N_2O$ released from compounds of the disclosure is as follows. GC is performed on a Varian CP-3800 instrument equipped with a 1041 manual injector, electron capture detector, and a 25 m 5 Å molecular sieve capillary column. Grade 5.0 nitrogen is used as both the carrier (8 mL/min) and the make-up (22 mL/min) gas. The injector oven and the detector oven are kept at 200° C. and 300° C., respectively. All nitrous oxide analyses are performed with the column oven held at a constant temperature of 150° C. All gas injections are made using a 100 μL gas-tight syringe with a sample-lock. Samples are prepared in 15 mL amber headspace vials with volumes pre-measured for sample uniformity (actual vial volume ranges from 15.19 to 15.20 mL). Vials are charged with 5 mL of PBS containing diethylenetriamine pentaacetic anhydride ("DTPAN"), purged with argon, and sealed with a rubber septum. The vials are equilibrated for at least 10 minutes at 37° C. in a dry block heater. A 10 mM stock solution of AS is prepared in 10 mM sodium hydroxide, and solutions of the nitroxyl donors are prepared in either acetonitrile or methanol and used immediately after preparation. From these stock solutions, 50 μL is introduced into individual thermally-equilibrated headspace vials using a 100 μL gas-tight syringe with a sample-lock to provide final substrate concentrations of 0.1 mM. Substrates are then incubated for 90 minutes or 360 minutes. The headspace (60 μL) is then sampled and injected five successive times into the GC apparatus using the gas-tight syringe with a sample lock. This procedure is repeated for 2 or more vials per donor.

4.3 In Vitro Plasma Stability of Compounds of the Disclosure in Plasma

A procedure for determining in vitro plasma stability of compounds of the disclosure is as follows. The assay system comprises plasma from rat, dog or human (at least 3 donors, male, pooled) at pH 7.4, and (ii) an anticoagulant (sodium heparin or sodium citrate). Each test compound (5 μM) is incubated in plasma at 37° C. on a THERMOMIXER® with shaking. Three samples (n=3) are taken at each of seven sampling time points: 0, 10, 30, 60, 90, 180 and 360 minutes. The samples are immediately combined with 3 volumes (i.e., 3 times the volume of plasma) of acetonitrile containing 1% formic acid and an internal standard to terminate the reaction. AB SCIEX API 3000 LC-MS/MS analysis of the test compounds is performed without a standard curve. Plasma half-lives ($T_{1/2}$) of the test compounds are determined from graphs of the percent remaining values using the peak area response ratio.

4.4 Pharmacodynamic Activity of Compounds of the Disclosure in Dogs

The effect of compounds of the disclosure on blood pressure in freely moving telemetered normal beagle dogs (n=3) after single oral doses is evaluated. The animals are surgically implanted with a pressure transducer equipped telemetry transmitter. The transmitter assembly is secured internally and a fluid-filled catheter is placed into the abdominal aorta to allow for collection of cardiovascular data. To evaluate cardiovascular effects, 3 dogs are given single oral doses of a test compound (100% PEG300 in gelatin capsules) at a concentration of 100 mg/mL and at doses of 30 mg/kg. Systemic blood pressure and heart rate are evaluated continuously for 2 hr before and for 24 hr after dosing. To compare the pharmacodynamic activity for all tested compounds, the mean systolic blood pressure (SBP) decrease during the first 2 hr post-dose is determined relative to the baseline SBP (30-120 min pre-dose).

While the invention has been disclosed in some detail by way of illustration and example for purposes of clarity of understanding, it is apparent to those in the art that various changes may be made and equivalents may be substituted without departing from the true spirit and scope of the invention. Therefore, the description and examples should not be construed as limiting the scope of the invention.

All references, publications, patents, and patent applications disclosed herein are hereby incorporated by reference in their entirety.

What is claimed is:

1. A compound, wherein the compound is:

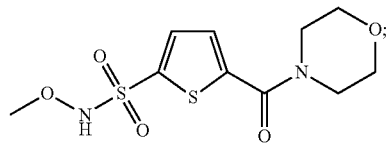 [SMILES: CONS(=O)(=O)c1ccc(C(=O)N2CCOCC2)s1]

or a pharmaceutically acceptable salt thereof.

2. A pharmaceutical composition comprising the compound of claim 1, and at least one pharmaceutically acceptable excipient.

3. A kit for treating a disease or condition responsive to nitroxyl therapy comprising a compound of claim 1; and instructions for use of the kit.

4. A method of treating a cardiovascular disease responsive to nitroxyl therapy, comprising administering an effective amount of the compound of claim 1, to a patient in need thereof.

\* \* \* \* \*